US012806088B2

(12) United States Patent
Remus

(10) Patent No.: US 12,806,088 B2
(45) Date of Patent: Nov. 24, 2026

(54) ABSORBENT ARTICLE PACKAGES

(71) Applicant: The Procter & Gamble Company, Cincinnati, OH (US)

(72) Inventor: Michael Remus, Heidelberg (DE)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 0 days.

(21) Appl. No.: 18/792,670

(22) Filed: Aug. 2, 2024

(65) Prior Publication Data

US 2025/0041134 A1 Feb. 6, 2025

(30) Foreign Application Priority Data

Aug. 4, 2023 (EP) .................................... 23189692

(51) Int. Cl.
*A61F 13/551* (2006.01)

(52) U.S. Cl.
CPC .... *A61F 13/5511* (2013.01); *A61F 13/55145* (2013.01)

(58) Field of Classification Search
USPC .................................................. 206/440, 494
See application file for complete search history.

(56) References Cited

U.S. PATENT DOCUMENTS

| | | | | |
|---|---|---|---|---|
| 5,655,843 | A | 8/1997 | Conrad et al. | |
| 6,454,095 | B1 | 9/2002 | Brisebois | |
| 6,708,823 | B2 * | 3/2004 | Cottingham | A61F 13/55165 206/440 |
| 7,172,073 | B2 | 2/2007 | Hanson | |
| 7,178,671 | B2 * | 2/2007 | Nichols | A61F 13/55165 206/440 |
| 8,261,914 | B2 | 9/2012 | Hooyman et al. | |
| 8,281,926 | B2 | 10/2012 | Messerschmidt et al. | |
| 8,479,920 | B2 | 7/2013 | Biber | |
| 8,622,618 | B2 * | 1/2014 | Moehlenbrock | B65D 33/16 383/203 |
| 8,662,301 | B2 | 3/2014 | Duval et al. | |
| 10,786,404 | B2 | 9/2020 | Cheng et al. | |
| 11,794,976 | B2 | 10/2023 | Remus | |
| 12,076,221 | B2 * | 9/2024 | Remus | B65D 75/12 |
| 12,178,692 | B2 * | 12/2024 | Remus | B65D 75/5816 |
| 2003/0115837 | A1 * | 6/2003 | Zimmer | B65D 33/1691 53/399 |
| 2003/0118255 | A1 | 6/2003 | Miller | |
| 2010/0055407 | A1 | 3/2010 | Belelie et al. | |

(Continued)

FOREIGN PATENT DOCUMENTS

| | | | |
|---|---|---|---|
| JP | 2011184076 | A | 9/2011 |
| WO | 2022026783 | A1 | 2/2022 |

OTHER PUBLICATIONS

All Office Actions; U.S. Appl. No. 18/794,095, filed Aug. 5, 2024.

(Continued)

*Primary Examiner* — Bryon P Gehman
(74) *Attorney, Agent, or Firm* — Amanda Herman Berghauer

(57) ABSTRACT

A package comprising one or more absorbent articles with a tactile indicium is disclosed. The package encloses one or more absorbent articles. The package comprises a plurality of panels forming an outer surface. The outer surface comprises a tactile indicium.

19 Claims, 26 Drawing Sheets

(56) References Cited

U.S. PATENT DOCUMENTS

| | | | | |
|---|---|---|---|---|
| 2013/0098793 | A1 | 4/2013 | Noguchi et al. | |
| 2013/0308883 | A1* | 11/2013 | Wehrmann ............. | B65D 65/14 383/210 |
| 2017/0057721 | A1 | 3/2017 | Lee et al. | |
| 2022/0402674 | A1 | 12/2022 | Cheng et al. | |
| 2025/0058961 | A1 | 2/2025 | Weisman et al. | |

OTHER PUBLICATIONS

CM05610FQ EPO Search Report and Opinion for Application No. 23189692.9; dated Apr. 30, 2024, 14 pages.
Unpublished U.S. Appl. No. 18/794,095, filed Aug. 5, 2024, Paul Thomas Weisman et al.
PCT Search report and Written opinion for PCT/US2024/040655 dated Jan. 9, 2025, 20 pages.

* cited by examiner

ABSORBENT ARTICLE PACKAGES

FIELD

The present disclosure is directed to absorbent article packages, more particularly to absorbent article packages comprising a primary seal and a secondary closing element.

BACKGROUND

There is an ever pressing need to reduce the environmental impact of products and packaging materials. Accordingly, consumer demand for products made at least partially from renewable resources has increased significantly over the past decade, and has become a driver of innovation for new and improved consumer goods and packaging materials. As such, there is an increased focus on products and packaging materials comprising renewable resources. For example, there is a strong desire in the marketplace for consumer products that comprise natural and bio-sourced materials, recyclable materials, recycled materials, and/or biodegradable materials.

Non-fragile, compressible consumer products such as disposable absorbent articles (e.g., diapers and training pants, disposable adult incontinence pants and feminine hygiene pads) are often packaged and sold at retail in soft packages formed of plastic polymer film. Plastic is preferred as the primary package of consumer goods because plastic may withstand the rigors of a packaging process, given plastic's ability to flex and stretch. Plastic packages, however, tend not to retain their shape, and may collapse upon removal of articles. Packages comprising renewable resources, such as natural fibers (e.g., carton board, cardboard, and paper), may be prone to creasing, cracking, and tearing under packaging processes and opening strain.

The environmental impact can be further reduced by reducing the overall packaging material. On the one hand, disposable absorbent articles are typically sold in multi-packs comprising a plurality of absorbent articles. On the other hand, consumer normally use one disposable absorbent article at a time. Absorbent articles are thus removed from the opened pack multiple times, often at different locations of use. Hence, the remaining articles in the multi-pack are exposed to environmental insults, such as humidity, dust etc., and thus potential contamination after first opening. As a consequence, disposable absorbent articles often are individually packed in addition to the multi-pack packaging. Therefore, there is need for packages providing protection from such environmental insults after first opening.

SUMMARY

It has surprisingly been found that by providing package materials comprising natural fibers, the packages of the present disclosure are able to retain their shape after opening such that the package can be reclosed via a secondary closing element. As a consequence, the environmental impact of the package can be reduced due to incorporation of materials from renewable sources and by protecting the articles from contamination after first opening.

A package comprising one or more absorbent articles is provided. The package comprises a package material comprising natural fibers. The package material forms a front panel, a back panel opposite the front panel, a first side panel, a second side panel opposite the first side panel, a top panel, and a bottom panel opposite the top panel. The panels define an interior compartment of the package. One or more absorbent articles are disposed in the interior compartment. The package comprises a primary seal and the package is sealed by the primary seal such that the one or more absorbent articles are enclosed within the interior compartment. The package comprises a secondary closing element and the secondary closing element is reclosable.

Further a bag to form a package comprising one or more absorbent articles is provided. The bag comprises a first surface, a second surface, a third surface, a fourth surface and a fifth surface, an open end opposing the first surface. One surface selected from the group consisting of second surface, the third surface, the fourth surface and the fifth surface comprises a secondary closing element. The secondary closing element is reclosable. Two or more surfaces selected from the group consisting of second surface, the third surface, the fourth surface and the fifth surface comprise a primary scaling area to form a primary seal.

BRIEF DESCRIPTION OF THE DRAWINGS

The above-mentioned and other features and advantages of the present disclosure, and the manner of attaining them, will become more apparent and the disclosure itself will be better understood by reference to the following description of example forms of the disclosure taken in conjunction with the accompanying drawings, wherein.

DETAILED DESCRIPTION

Figure 1A:
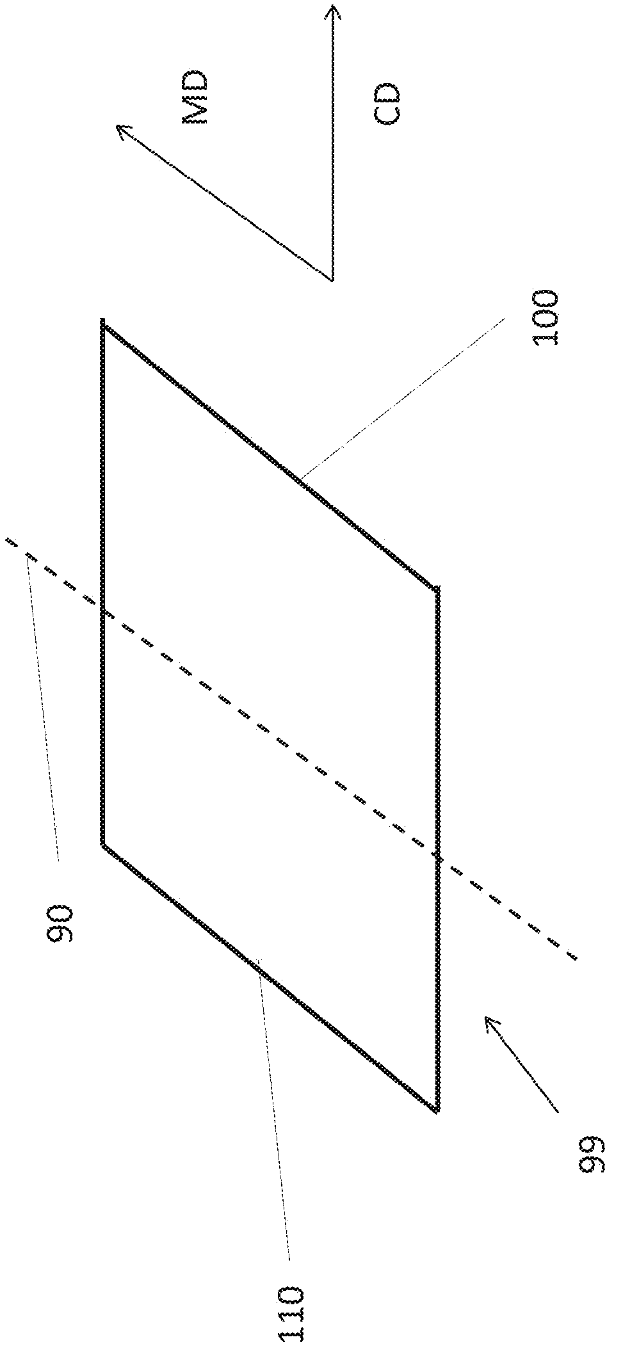
FIG. 1A is a schematic representation of a package material sheet.

The term "absorbent article", as used herein, refers to devices which absorb and contain exudates, and, more specifically, refers to devices which are placed against or in proximity to the body of the wearer to absorb and contain the various exudates discharged from the body. Absorbent articles of the present disclosure include, but are not limited to, diapers, adult incontinence briefs, training pants, diaper holders, menstrual pads, incontinence pads, liners, absorbent inserts, pantiliners, tampons, and the like.

The term "machine direction" or "MD", as used herein, refers to a path that material, such as a package material, follows through a manufacturing process.

The term "cross-machine direction" or "CD", as used herein, refers to a path that is perpendicular to the machine direction in the plane of the material.

The term "natural fibers" as used herein, refers to fibers which comprise cellulose-based fibers, bamboo fibers, and the like. Natural fibers also refers to: nonwoody fibers, such as cotton, abaca, kenaf, sabai grass, flax, esparto grass, straw, jute, hemp, bagasse, milkweed floss fibers, and pineapple leaf fibers; and woody fibers, such as wood or pulp fibers such as those obtained from deciduous and coniferous trees, including softwood fibers, such as northern and southern softwood kraft fibers, hardwood fibers, such as eucalyptus, maple, birch, and aspen. Pulp fibers may be prepared in high-yield or low-yield forms and may be pulped in any known method, including kraft, sulfite, high-yield pulping methods and other known pulping methods. The natural fibers of the present disclosure may be recycled natural fibers, virgin natural fibers or mixes thereof. Additionally, for good mechanical properties in natural fibers, it may be desirable that the natural fibers be relatively undamaged and largely unrefined or only lightly refined. The fibers may have a Canadian Standard Freeness of at least 200, more specifically at least 300, more specifically still at least 400, and most specifically at least 500.

The term "cellulose-based fibers," as used herein, may include regenerated cellulose fiber such rayon or cuprammonium rayon, and high pulping yield fibers, unless specified differently. The term "cellulose-based fibers" also includes chemically treated natural fibers, such as mercerized pulps, chemically stiffened or crosslinked fibers, or sulfonated fibers. Also included are mercerized natural fibers, regenerated natural cellulosic fibers, cellulose produced by microbes, the rayon process, cellulose dissolution and coagulation spinning processes, and other cellulosic material or cellulosic derivatives. Other cellulose-based fibers included are paper broke or recycled fibers and high yield pulp fibers. High yield pulp fibers are those fibers produced by pulping processes providing a yield of about 65% or greater, more specifically about 75% or greater, and still more specifically about 75% to about 95%. Yield is the resulting amount of processed fibers expressed as a percentage of the initial wood mass. Such pulping processes include bleached chemithermomechanical pulp (BCTMP), chemithermomechanical pulp (CTMP), pressure/pressure thermomechanical pulp (PTMP), thermomechanical pulp (TMP), thermomechanical chemical pulp (TMCP), high yield sulfite pulps, and high yield Kraft pulps, all of which leave the resulting fibers with high levels of lignin but are still considered to be natural fibers. High yield fibers are well known for their stiffness in both dry and wet states relative to typical chemically pulped fibers.

Package Configurations

The package materials of the present disclosure may be arranged as a package in a myriad of configurations to contain absorbent articles. The package comprises a plurality of panels which define an interior compartment and enclose one or more than one absorbent article. When in a scaled state, such as during transport and on display on a store shelf, the package completely encloses the one or more than one absorbent article. Each of the panels comprises an inner surface—facing inward toward the packaged absorbent article—and an outer surface—facing outward toward the consumer. The outer surface and/or inner surface of one or more panels may comprise inks or dyes which create branding on the package, package information, and/or background color. The branding and/or package information associated with the absorbent articles within the package may be provided on an outer surface of at least one panel. Branding may include logos, trade names, trademarks, icons, and the like, associated with the absorbent articles within the package. Branding may be utilized to inform a consumer of the brand of the absorbent articles within the package. As an example, branding for a package of feminine hygiene pads may comprise the brand name Always®. Package information may include the size of the absorbent articles, the number of absorbent articles within the package, an exemplary image of the absorbent articles contained within the package, recyclability logos, and the like. As an example, package information for a package of feminine hygiene pads may comprise a size indicator, e.g., "Size 1."

The package materials of the present disclosure may be supplied by a manufacturer of package materials to an absorbent article manufacturer. The package materials may be pre-formed to some extent into a finished package shape, or the manufacturer of package materials may simply provide rolls of the package materials to the absorbent article manufacturer. The package material may be unitary, meaning that a package is formed from a single piece of package material. For example, multiple folds and seams may be utilized to form the plurality of panels of the package from a single piece of package material. In such examples, the absorbent article manufacturer may create the folds and seams as described herein to form a package for absorbent articles. The packages of the present disclosure may comprise package material which comprises a plurality of discrete portions. Such configurations are described in additional detail herein.

Figure 1B:
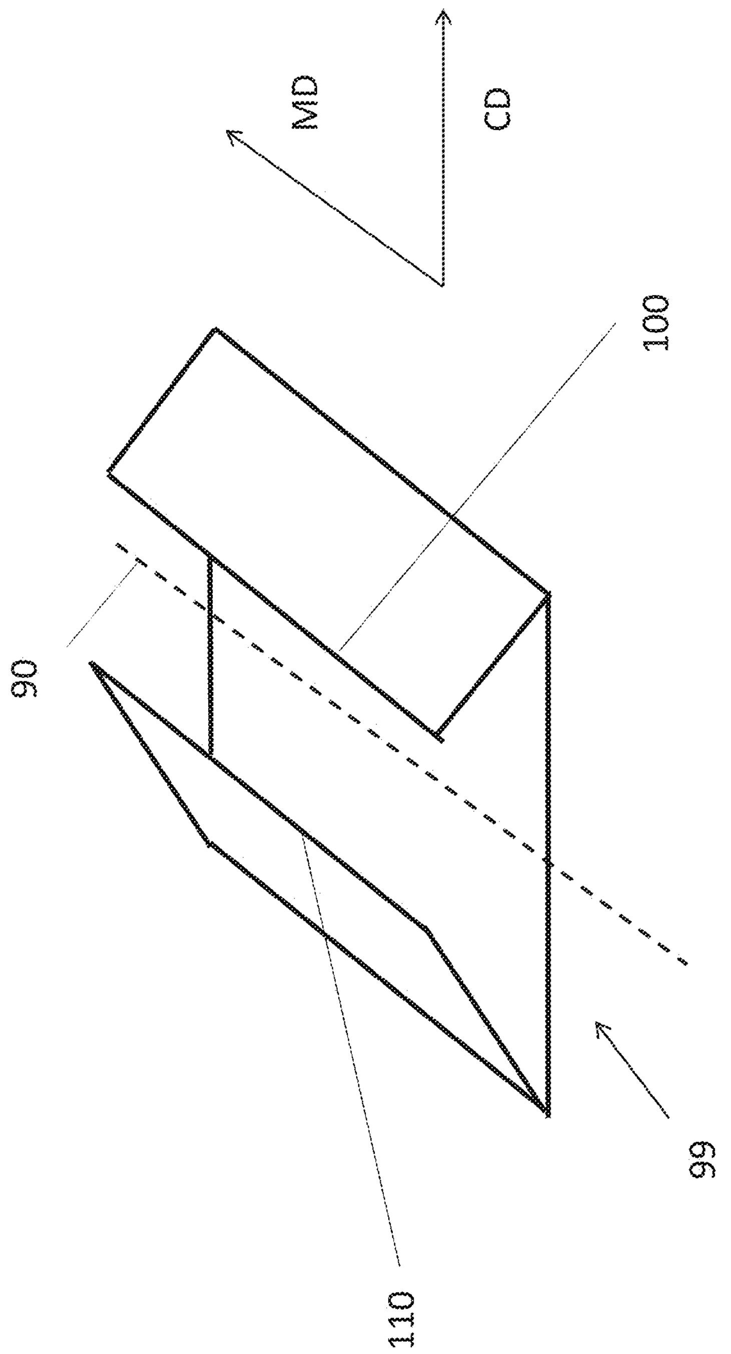
FIG. 1B is a schematic representation showing the package material sheet of FIG. 1A in a partially folded configuration.

Regardless of whether the package material is on rolls or pre-formed to some extent, the packages of the present disclosure begin with paper stock. Referring to FIGS. 1A-1B, edge portions 100 and 110 of a paper stock sheet 99 may be folded towards each other and subsequently sealed to form a seam. For example, side portions 100 and 110 of the sheet 99 may be brought inward towards a longitudinal centerline 90 of the sheet 99 to form a hoop seam 95 (see FIG. 1C). These edge portions may be overlapped with one another and sealed together to form an overlap scam. Alternatively, the edge portions 100 and 110 may be joined together on their respective inner surfaces to form a butt seam. Butt seams tend to not lay as flat as an overlap seam. Therefore, where the scam is located, at least in part, on a bottom panel upon which the package may rest, an overlap scam may be desirable such that the package may sit on a flatter bottom panel.

Figure 1C:
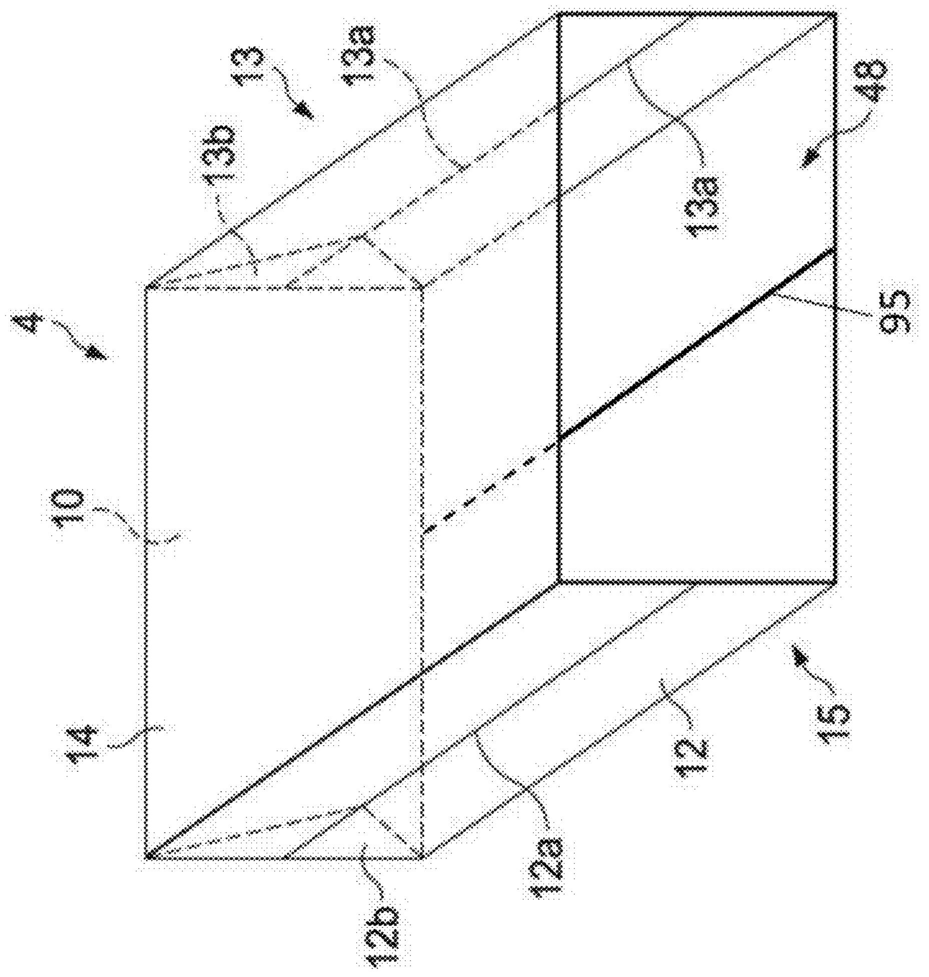
FIG. 1C is a schematic representation of a bag with an open end.
Figure 1D:
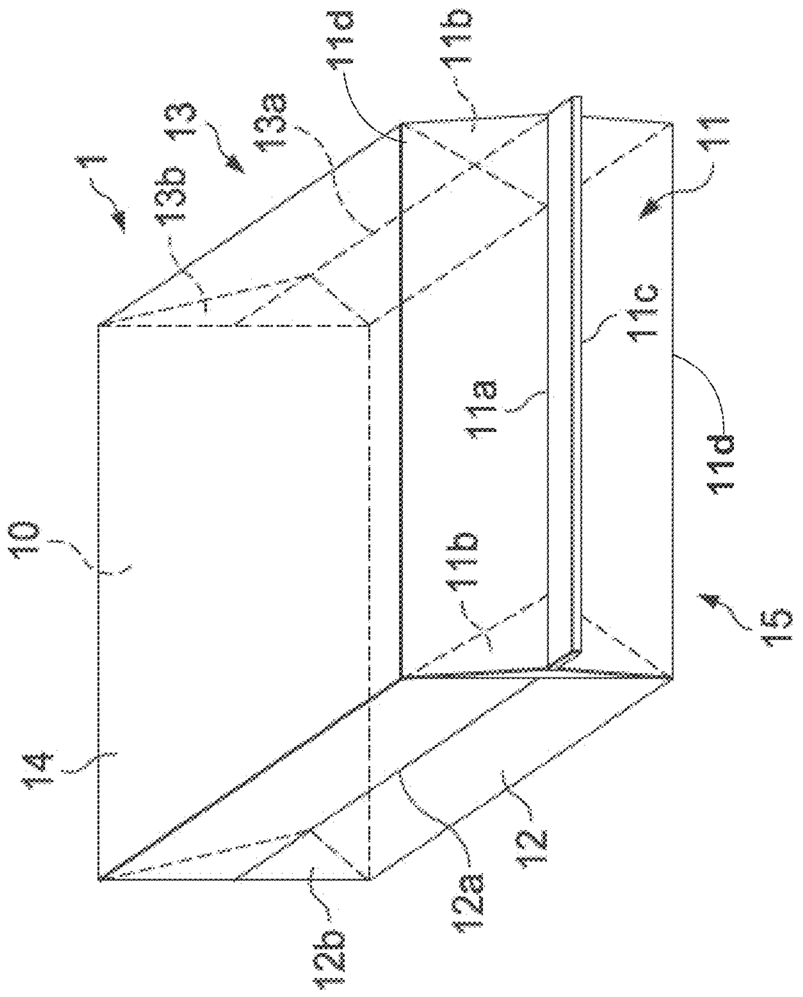
FIG. 1D is a schematic representation of the package formed from the bag of FIG. 1C in a closed state.
Figure 1E:
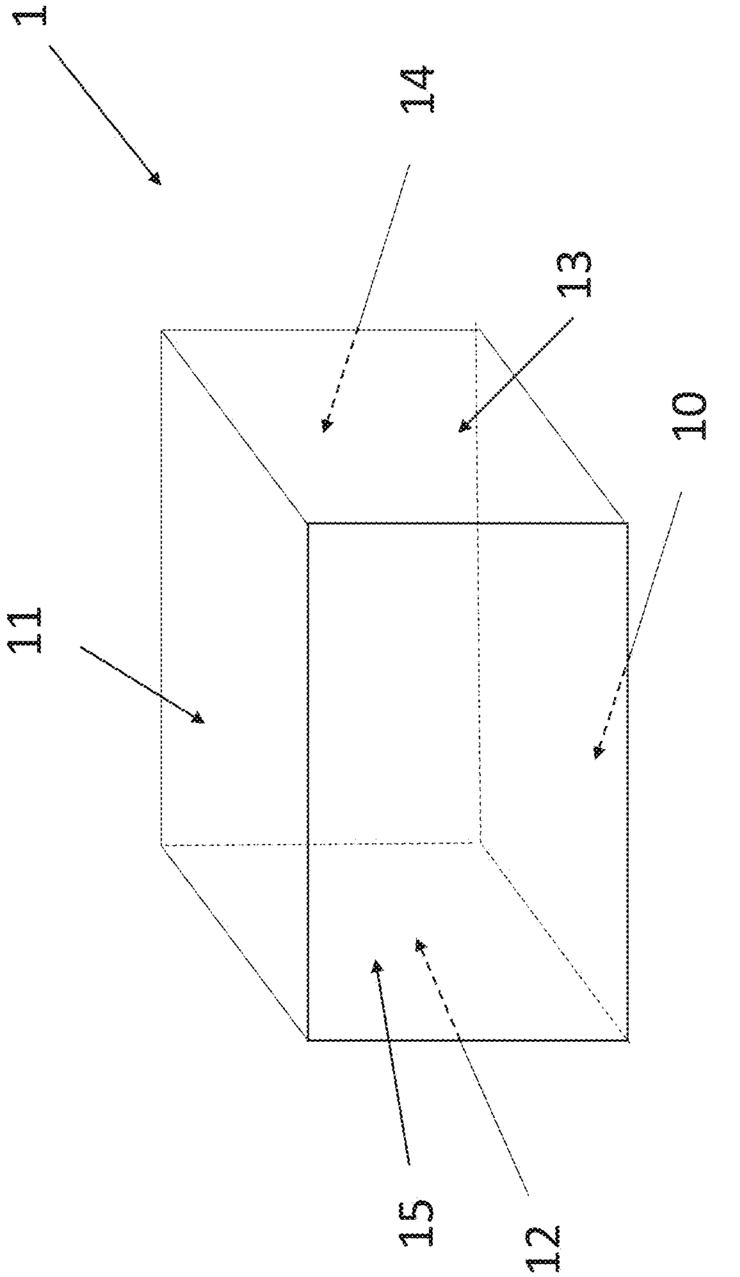
FIG. 1E is a schematic representation of another package of the present disclosure shown in a closed state.

Referring to FIG. 1C-1E, the sheet of packaging material may be suitably folded to form bag side creases 12*b* and 13*b* and two side folds 12*a* and 13*a* on opposite sides, to form the bag structure 4 having a first surface 10, a second and third surface 12, 13, respectively, and a fourth and a fifth surface 14, 15. An open end 48 opposes the first surface 10. Each side crease 12*b*, 13*b* may be located at the respective second or third surface 12, 13. It is worth noting that in FIGS. 1C and 1D, the crease and folds shown are for a package having a block configuration or block bottom configuration. Gussets and fold lines for a pinch bottom bag are discussed in additional detail with regard to FIG. 2B.

The bag 4 may be filled by inserting articles, such as a plurality of absorbent articles, through the open end 48. When the bag 4 is filled with a plurality of articles, e.g., by loading articles from the open end 48, the device used to introduce the articles inside the bag 4 together with the articles may exert some tension on each of the second and third surfaces 12, 13 of the bag 4. For example, the articles may be compressed before being inserted into the bag 4 so that the articles may slightly expand after they are introduced in the bag 4, and thus exert some tension on the second and third surfaces 12, 13 as well as the fourth surface 14 and the fifth surface 15. The tension may be exerted on each of the creases 12*b*, 13*b* at the respective second and third surfaces 12, 13, particularly along the first and second side folds 12*a*, 13*a* by which the package may maintain a substantially parallelepiped shape.

As may be appreciated from FIG. 1D, the open end 48 opposite the first surface 10 may then be closed to form a sixth surface 11. Any suitable style of closing may be utilized. In a form, the sixth surface may comprise closing gussets 11*b*, wherein portions of the outer surface of the package material at the closing gussets 11*b* are brought to form a closing seam 11*a* and a closing seam fin 11*c* extending from the closing seam 11*a*, and sixth surface 11. At least a portion of the closing seam fin 11*c* may be attached to at least a portion of the sixth surface 11. Tacking down the closing seam fin 11*c* to at least a portion of the sixth surface may reduce the risk of unintentional opening of the package, provide for increased stackability, as well provide a cleaner look on-shelf look. Instead of forming closing gussets and a closing fin, the sixth surface may comprise seams which are joined together in a block style configuration or cross style configuration, discussed further herein.

Figure 2A:
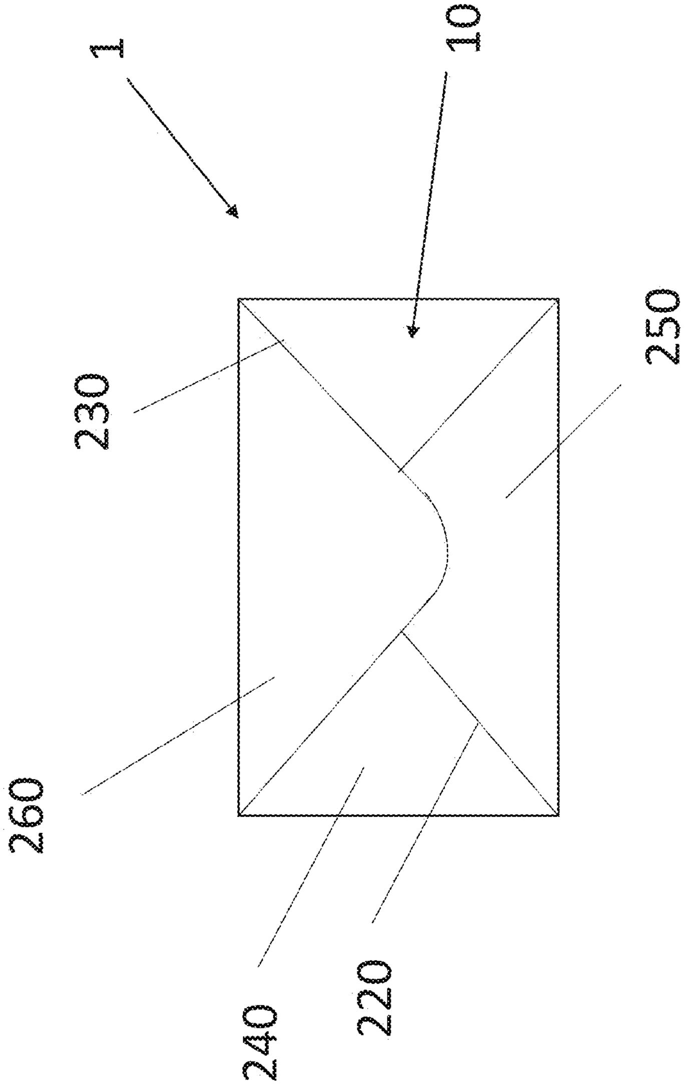
FIG. 2A is a schematic representation showing a panel of a package of the present disclosure, wherein the panel comprises seals in a block bottom configuration.

An example of a block style configuration is shown in FIG. 2A. As shown, the first surface 10 may comprise block style seams 220 and 230. The first surface 10 may comprise a base portion 240. A first flap of package material 250 may be folded onto the base portion 240. First seams 220 may be provided to attach the first flap of package material 250 to the base portion 240. A second flap of package material 260 may be folded onto the base portion 240 and on top of the first flap of package material 250. Second seams 230 may be provided to attach the second flap of package material 260 to the base portion 240 and to the first flap of package material 250. A similar execution may be utilized regarding the sixth surface 11 to form a closure.

Figure 2B:
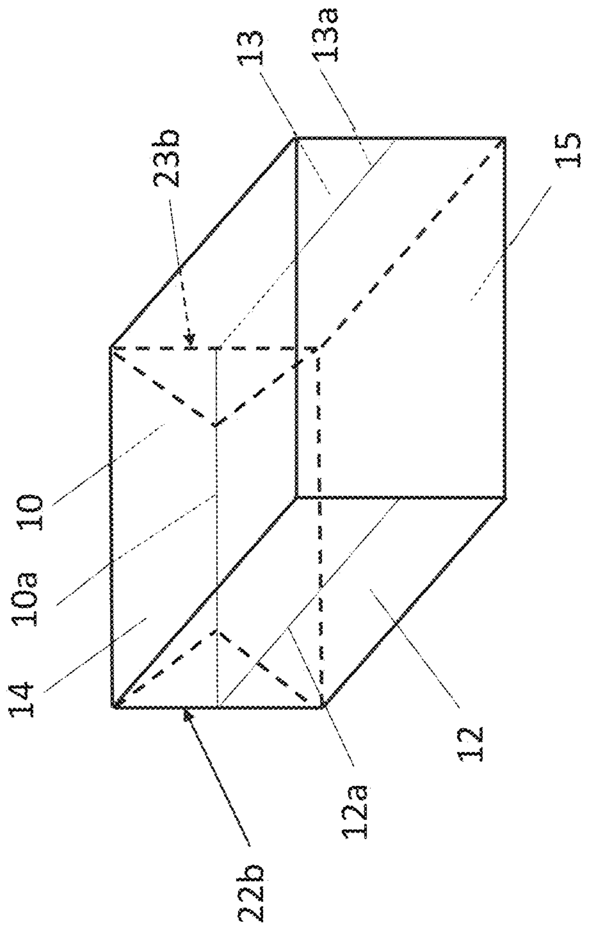
FIG. 2B is a schematic representation showing a panel of a package of the present disclosure, wherein the panel comprises seals in a pinch bottom configuration.

Another example of a panel sealing style which may be utilized with the packages of the present disclosure is the pinch style configuration or the pinch bottom style. An example of a pinch style configuration is shown in FIG. 2B. As shown, one of the key differences between the block bottom and the pinch bottom configuration is the configuration of the creases 12*b* and 13*b*. Instead of creases on the sides 12 and 13, a pinch style configuration comprises gussets 22*b* and 23*b* on the first surface 10. Additionally, in the pinch bottom configuration, the first surface 10 comprises a fold line 10*a* which may be absent in the block style configuration. A similar pinch style configuration may be utilized regarding the sixth surface 11 to form a closure.

Figure 2C:
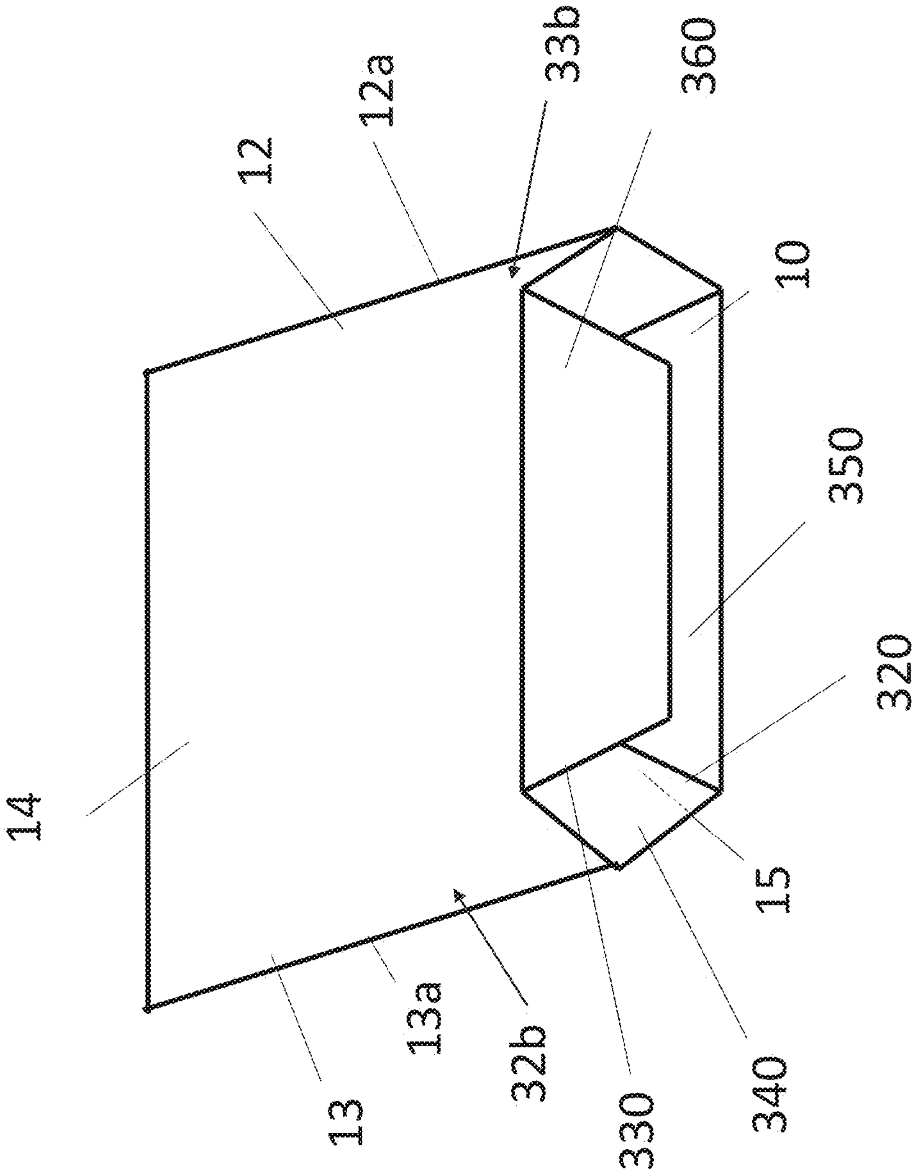
FIG. 2C is a schematic representation showing a panel of a package of the present disclosure, wherein the panel comprises seals in a cross bottom configuration.

Cross style or cross bottom style configurations are also acceptable for sealing portions of the package materials of the present disclosure. An example of a cross style configuration is shown in FIG. 2C. As shown, one of the key differences between the cross style configuration and the block style configuration is that gussets 32*b* and 33*b* and fold lines 12*a* and 13*a* are oriented outward of the interior of the package. In a block-style configuration (FIG. 1C), on the other hand, fold lines 12*a* and 13*a* on the second surface 12 and the third surface 13, respectively, are oriented inward prior to filling the package. Due to the orientation of the gussets 32*b* and 33*b* in the cross style configuration, filling the package with absorbent articles may require less energy to expand the package for filling. As an example, creases oriented inward, e.g., block style configuration, would require displacement outward of the creases prior to filling the package. Additionally, the equipment utilized in guiding the product into the package may have a reduced likelihood of interfering with the gussets, given their orientation outward. This may reduce the likelihood of packaging mishaps or manufacturing process stoppages due to quality issues.

Referring again to FIG. 2C, similar to the block style configuration, the first surface 10 of the cross style configuration comprises seams 320 and 330. The first surface comprises a base portion 340. A first flap of package material 350 may be folded onto the base portion 340. First seams 320 may be provided to attach the first flap of package material 350 to the base portion 340. A second flap of package material 360 may be folded onto the base portion 340 and on top of the first flap of package material 350. Second seams 330 may be provided to attach the second flap of package material 360 to the base portion 340 and/or to the first flap of package material 350. A similar execution may be utilized to form the closure on the sixth surface (formed once the package is sealed after the placement of absorbent articles therein).

For less bulky items, where standability of the package is desired, the block bottom or cross bottom may be desirable, as these configurations form a flat base. However, for bulky items, the pinch style configuration bags may be beneficial as the bulky absorbent articles therein may form a steady base for the package to stand. The inventors have surprisingly found that diapers may be suited for pinch bottom bags due their bulky nature. In contrast, feminine hygiene articles, particularly menstrual pads, may be suited for block bottom configured packages.

Additionally, it is worth noting that block style and cross style configured packages tend to be themselves bulkier than their pinch style counterparts. For the purposes of packaging absorbent articles, unfilled packages may arrive pre-formed in stacks to an absorbent article manufacturer. Typically, stacks of pre-formed block style and cross style configuration packages will take up more space—due to their bulkiness—as compared to pre-formed pinch style packages. The bulkiness of the block and cross style configurations may make the stacks more difficult to manipulate during the filling process, particularly where a large number of filled packages are created per minute. In such instances, the bulkiness of these configurations may mean an increased frequency of replenishment of the stacks.

Referring back to FIGS. 1C-ID, the first surface 10 may form at least a portion of the top panel of the package 1. In another embodiment, the first surface 10 may form at least a portion of the bottom panel of the package 1. It is worth noting that if the first surface 10 comprises scams, it may be desirable that the first surface 10 forms at least a portion of the bottom panel. In this way the seams may be hidden from view on the store shelf. The second and third surfaces 12 and 13, as they may comprise gussets 12*b* and 13*b*, respectively, may form at least a portion of a first side panel and opposite second side panel, respectively, or vice versa. The fourth and fifth surfaces 14, 15 may form at least a portion of a front panel and an opposite back panel, respectively, or vice versa. At least one of the fourth and/or fifth surface 14, 15, may comprise branding, product information and/or background color as described herein, as the front panel is generally the consumer-facing panel. However, product information and/or background color may not be limited to the consumer-facing panel. Any combination of the panels of the packages of the present disclosure may comprise branding, product information, and/or background color. The sixth surface 11 may form at least a portion of the top panel or at least a portion of the bottom panel of the package 1. Where the sixth surface 11 comprises closing gussets 11*b*, closing seam 11*a*, and a closing seam fin 11*c* extending from the closing seam 11*a*, it may be desirable that the sixth surface 11 forms at least a portion of the top panel. In this way the closing gussets 11*b* and closing scam fin 11*c* do not introduce bulk and instability to the base of the package. Where the sixth surface 11 forms at least a portion of the top panel, a top edge region 11*d* is formed at the transition from the top panel to the front, back, and first and second side panels. The top edge region 11*d* may be formed by portions of the top, front, back, first side, and second side panels that are adjacent to a fold in the package material designating a transition from the top panel to another panel.

Figure 7:
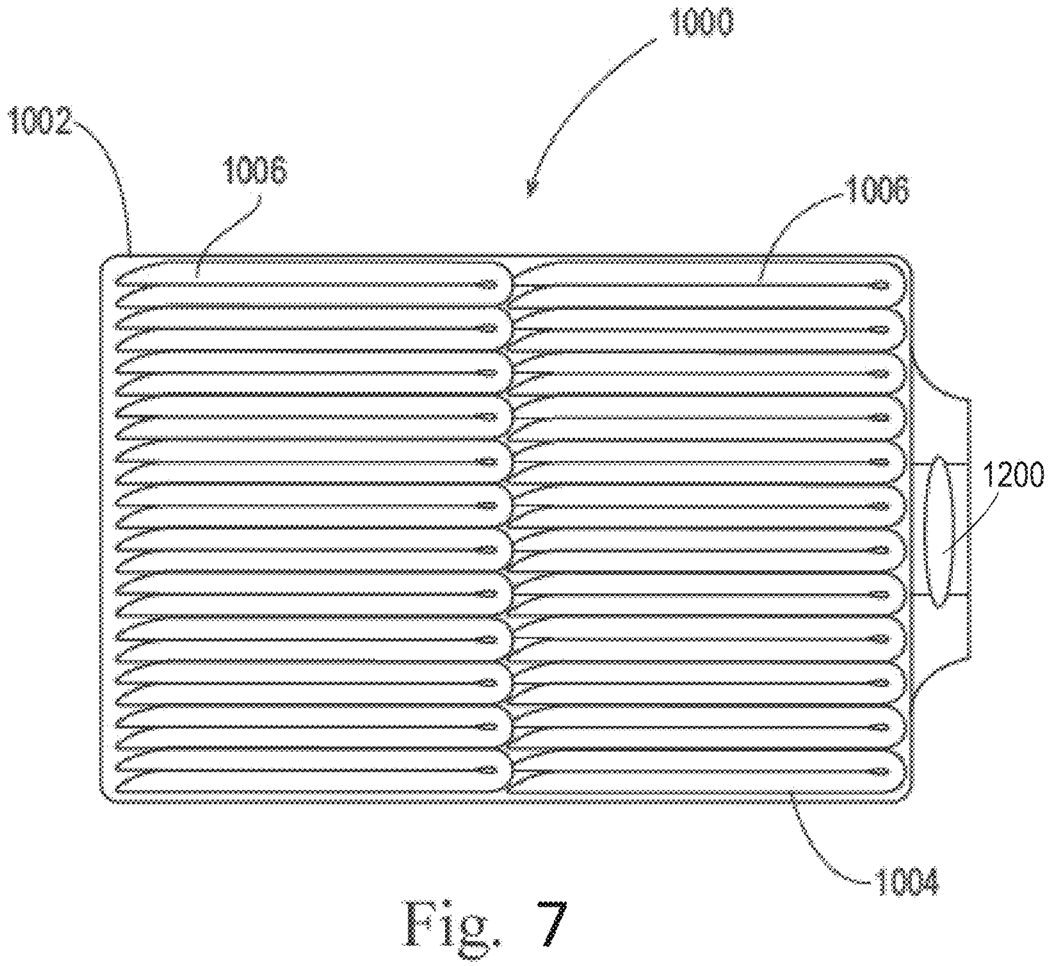
FIG. 7 is a front view of a multiple stacks of a plurality of absorbent articles disposed within a package of the present disclosure.
Figure 9A:
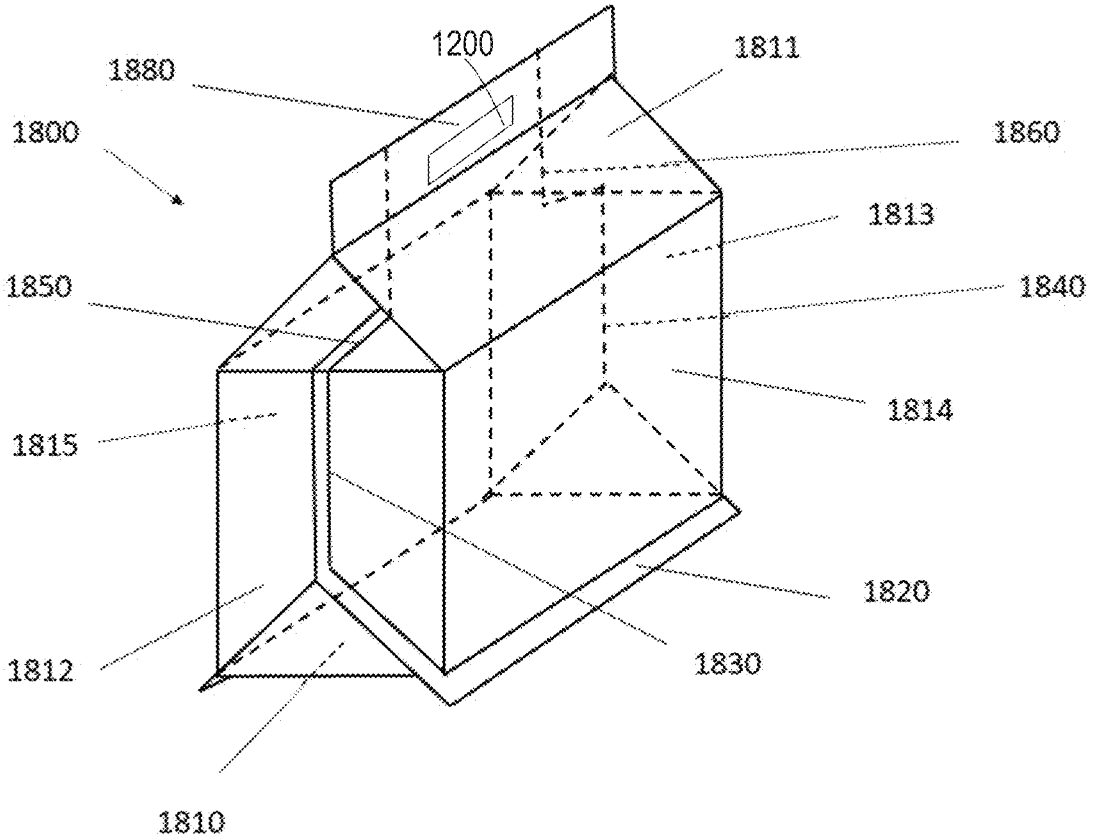
FIG. 9A is a schematic representation of a package configuration in accordance with the present disclosure constructed in accordance with the present disclosure.

The closing seam fin 11*c* may comprise a carrying handle 1200, as shown in FIGS. 7, 9A- and 9B. The carrying handle 1200 may be formed by a portion of the closing seam fin 11*c* that is devoid of packaging material. In a form, as least a portion of the packaging material forming the closing seam fin 11*c* may be excised to define the carrying handle 1200. The carrying handle 1200 may be configured to allow a user to engage the carrying handle 1200 without needing to grasp the handle with the user's hands. For example, the carrying handle 1200 may be sized to allow a user to slip their entire hand through the carrying handle 1200, and hook the carrying handle 1200 around the user's wrist, thus keeping the user's hand free. As such, the area defining the carrying handle 1200 may measure at least 100 $cm^2$, at least 150 $cm^2$, at least 200 $cm^2$, or at least 250 $cm^2$.

Figure 8:
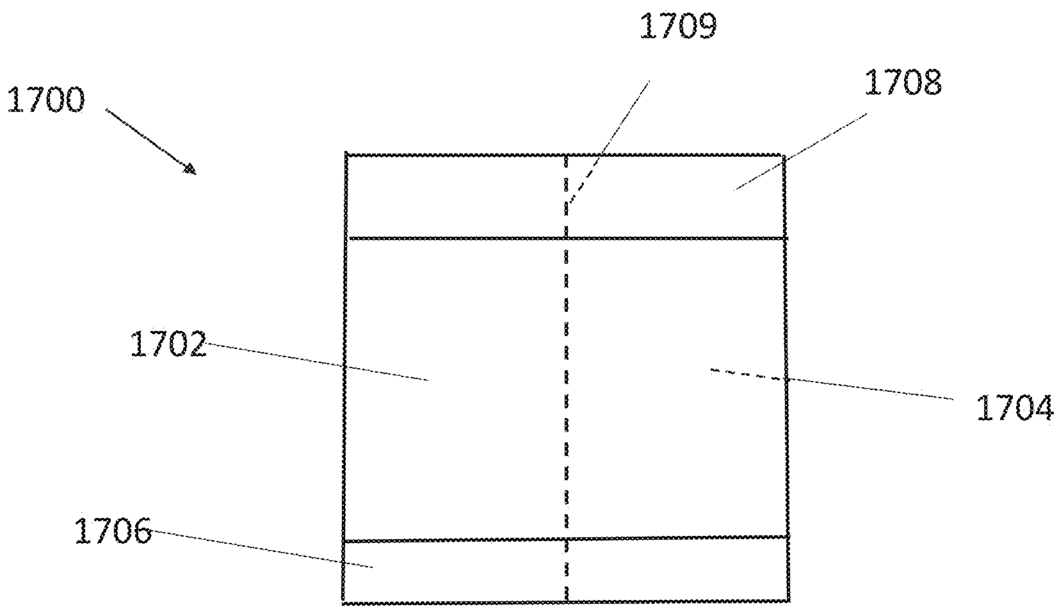
FIG. 8 is a schematic plan view of a package of the present disclosure constructed with a flow wrap process.

Other package shapes are contemplated. Examples of such packages include flow wrap or horizontal form fill-and-seal wrap. Such packages may comprise a generally cuboid shape also configured as described above. However, in some instances, such as shown in FIG. 8, a flow wrap package 1700 may comprise a first surface 1702 and an opposing second surface 1704. Rounded edges may be provided as a transition between the first surface 1702 and the second surface 1704. In another form, one or more fold lines may be provided between the first surface 1702 and the second surface 1704. The flow wrap package 1700 may further comprise end seals 1706 and 1708, and a hoop seam 1709 which may be disposed on the second surface 1704. In such packages, the first surface 1702 may comprise the consumer-facing panel. Flow wrap packages may be useful, particularly where a low number of absorbent articles are included within a package.

Figure 9B:
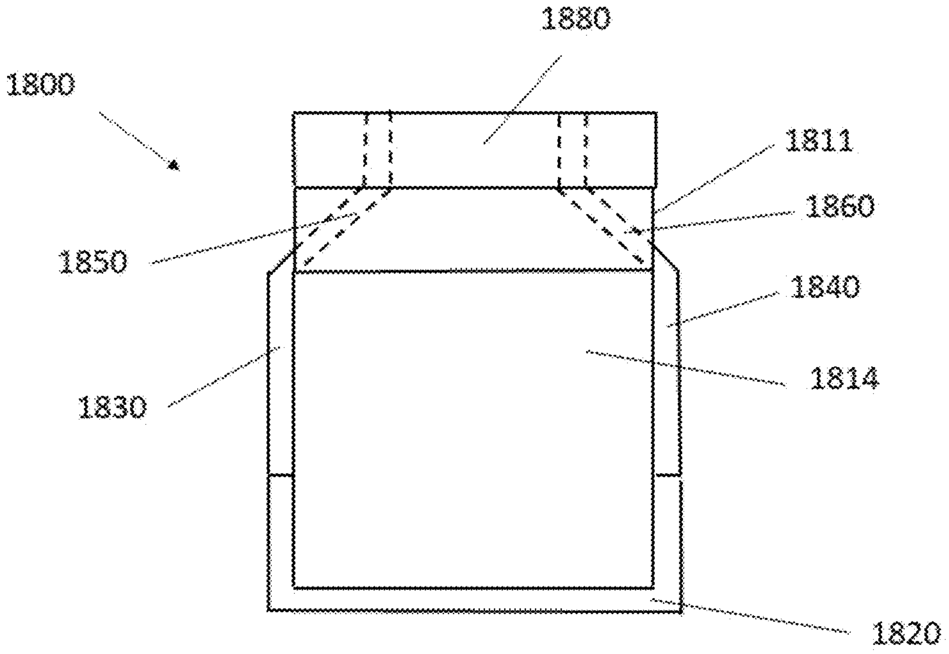
FIG. 9B is a schematic representation of a front view of the package configuration of FIG. 9A.

Another package form in accordance with the present disclosure may comprise seams/seals which are move overt than those packages comprising a block bottom, pinch bottom, and/or cross bottom. Referring to FIGS. 9A and 9B, a package 1800 is shown. The package 1800 may be configured in generally a cuboid shape. The package 1800 may comprise a first panel 1811, opposing second and third panels 1812 and 1813, opposing fourth and fifth panels 1814 and 1815, and a sixth panel 1810 opposing the first panel 1811. As shown, between the fourth panel 1814 and the sixth panel 1810, a first seam 1820 extends outward. The first seam 1820 is not to be confused with the primary seal 2. The first seam 1820 may form a sort of foot for the package 1800. A second seam (not shown) may extend outward between the fifth panel 1815 and the sixth panel 1810 in a similar fashion to the first seam 1820.

The first seam 1820 can extend such that a portion of the first seam 1820 is on the second panel 1812 and another portion of the first seam 1820 is disposed on the third panel 1813. Similarly, a portion of the second seam may be disposed on the second panel 1812 and another portion may be disposed on the third panel 1813. The first seal 1820 and the second seam may be provided where the sixth panel 1810 is formed from a discrete piece of material which is subsequently joined to the fourth panel 1814 and fifth panel 1815. Of course, forms where the sixth panel 1810 is unitary with the fourth panel 1814 and fifth panel 1815 are also contemplated.

A third seam 1830 and a fourth seam 1840 may extend outward from the second panel 1812 and the third panel 1813, respectively. It is worth noting that the first seam 1820, second seam, third scam 1830, and fourth seam 1840 collectively may comprise the hoop seal discussed herein. Thus, one, all, or any combination, of these seals may exhibit the tensile strength for the hoop seal as described herein.

As shown, the package 1800 may further comprise a fifth seam 1850 and a sixth scam 1860 which are disposed on the sixth panel 1811. The fifth seam 1850 and sixth seam 1860 can extend into a seal fin 1880. It is worth noting that the package 1800 and the seams associated therewith, may be assembled as described herein regarding adhesives, barrier films, and/or combinations of barrier films and adhesives. However, the construction of the package 1800 is particularly well suited for the creation of seams via barrier film coating on an inner surface of the package material. In such configurations, the film may form a barrier that reduces the likelihood or at least the amount of moisture vapor through the package material to the absorbent articles therein.

Figure 10A:
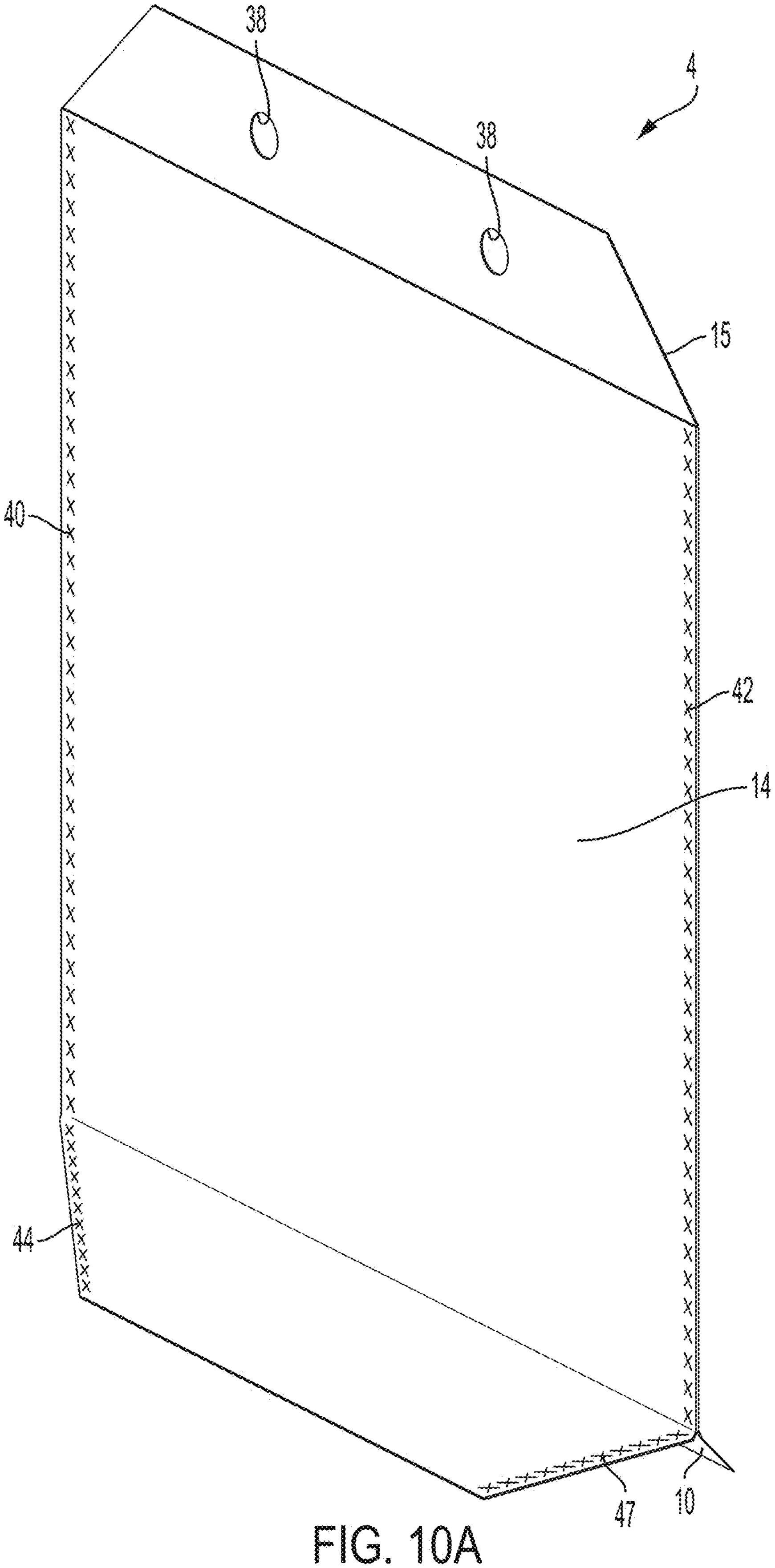
FIG. 10A is a perspective view of a bag of the present disclosure in a partially flattened configuration and without one or more absorbent articles within the bag.
Figure 10B:
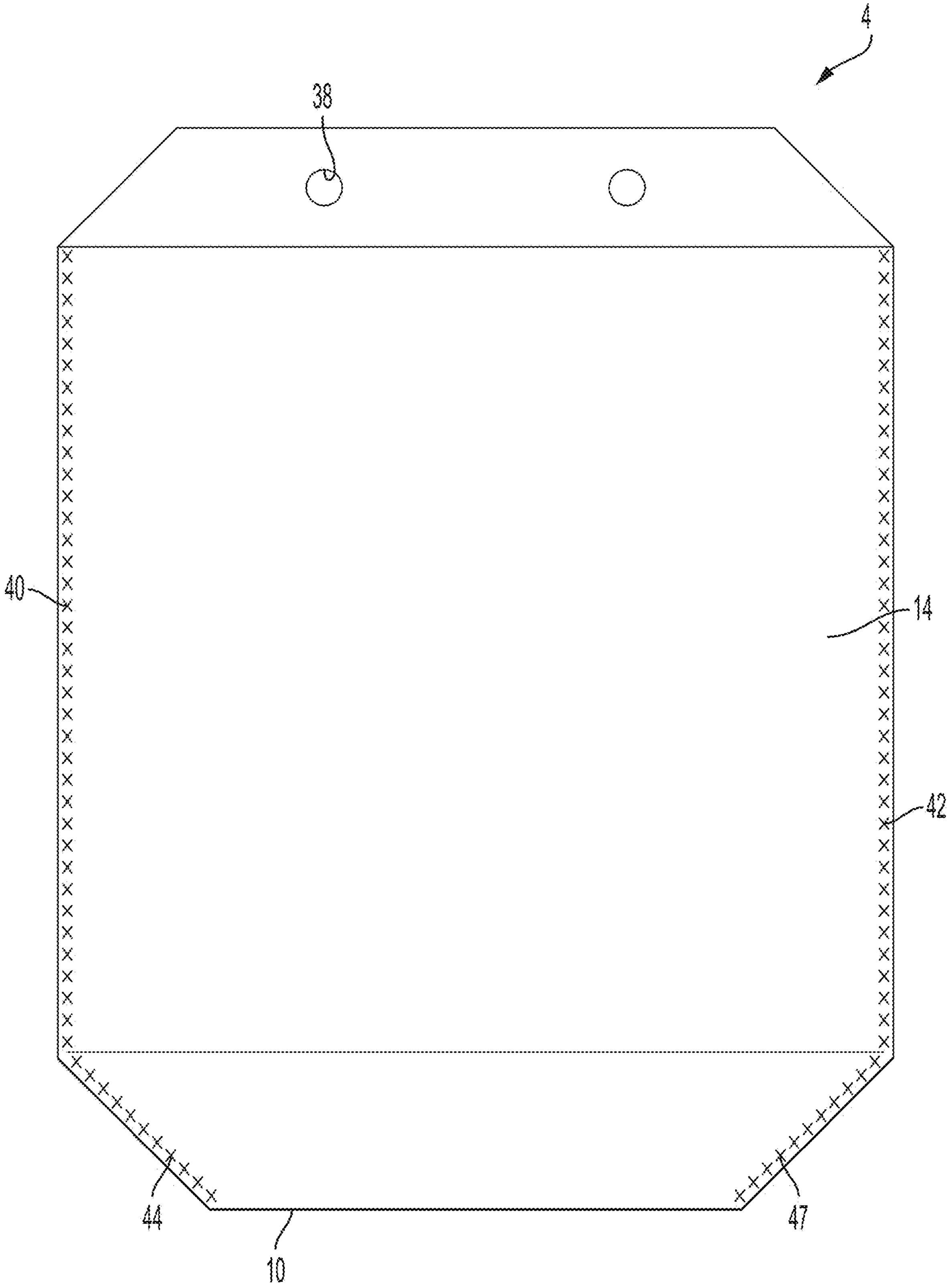
FIG. 10B is a front view of the bag of FIG. 10A.
Figure 10C:
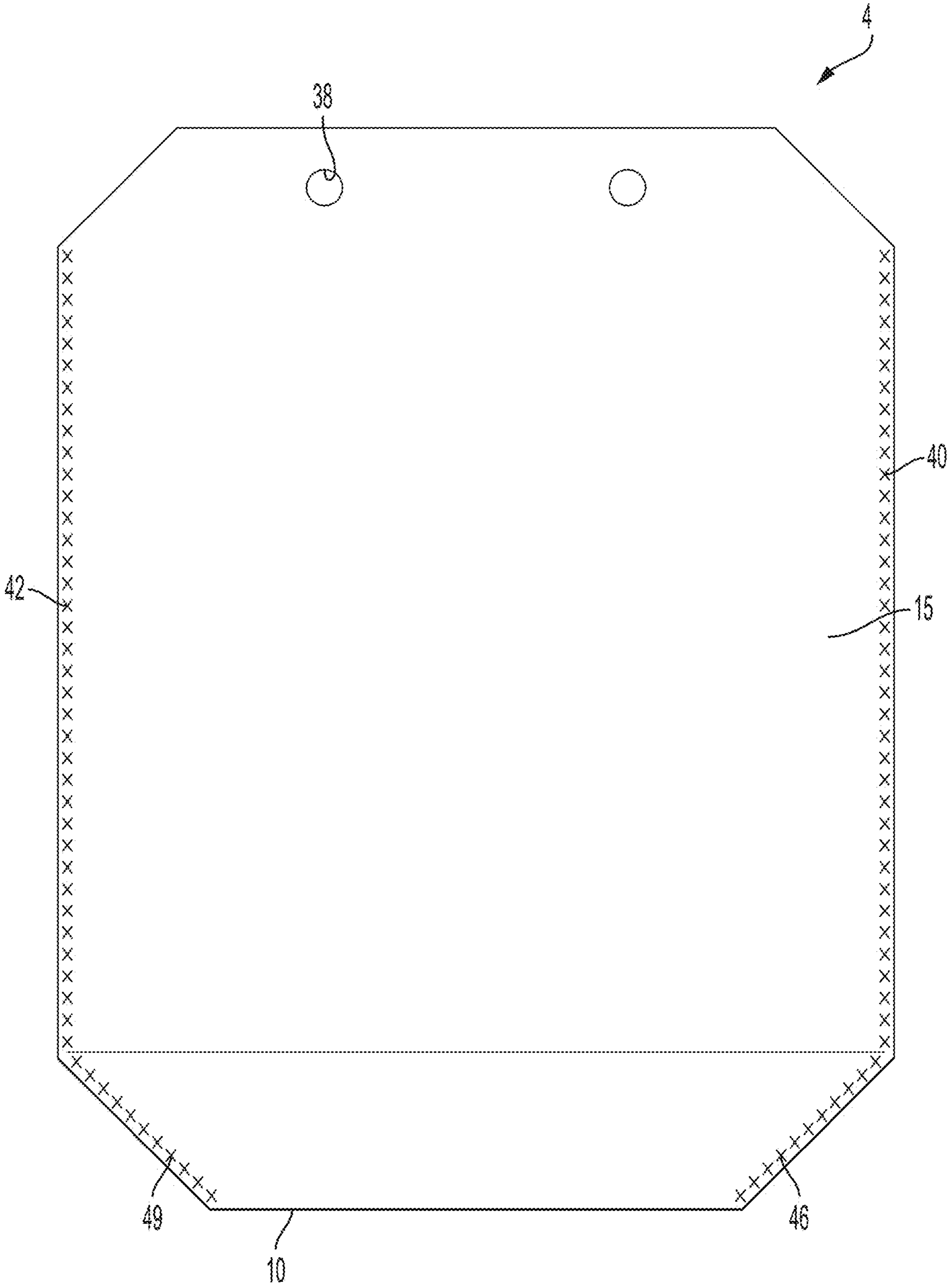
FIG. 10C is a back view of the bag of FIG. 10A.
Figure 10D:
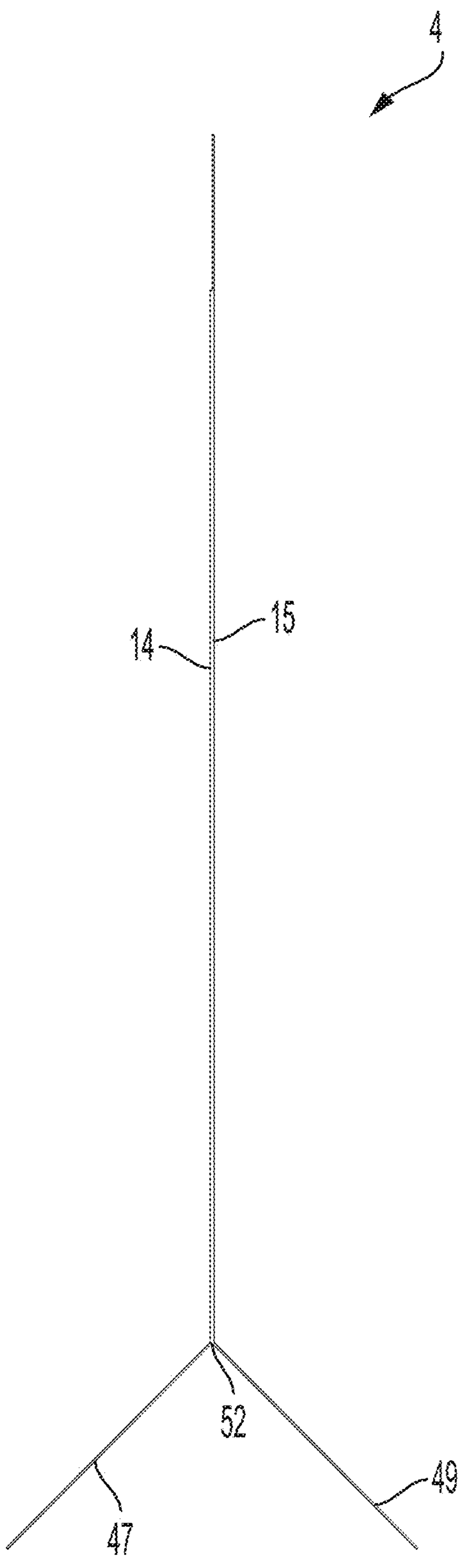
FIG. 10D is right side view of the bag of FIG. 10A, with the left side view being identical.
Figure 10E:
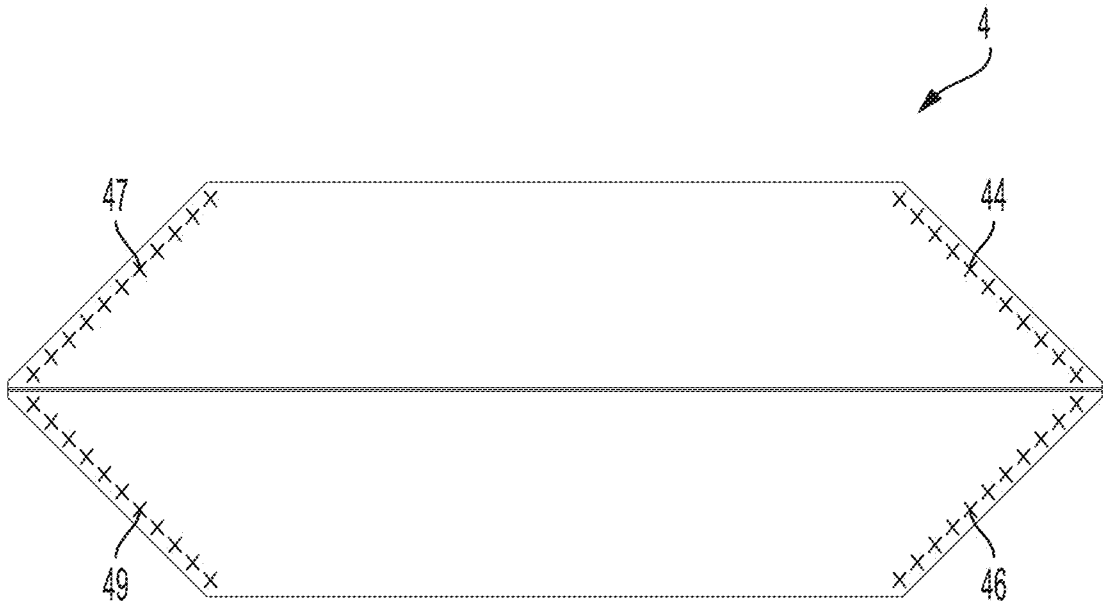
FIG. 10E is a top view of the bag of FIG. 10A.
Figure 10F:
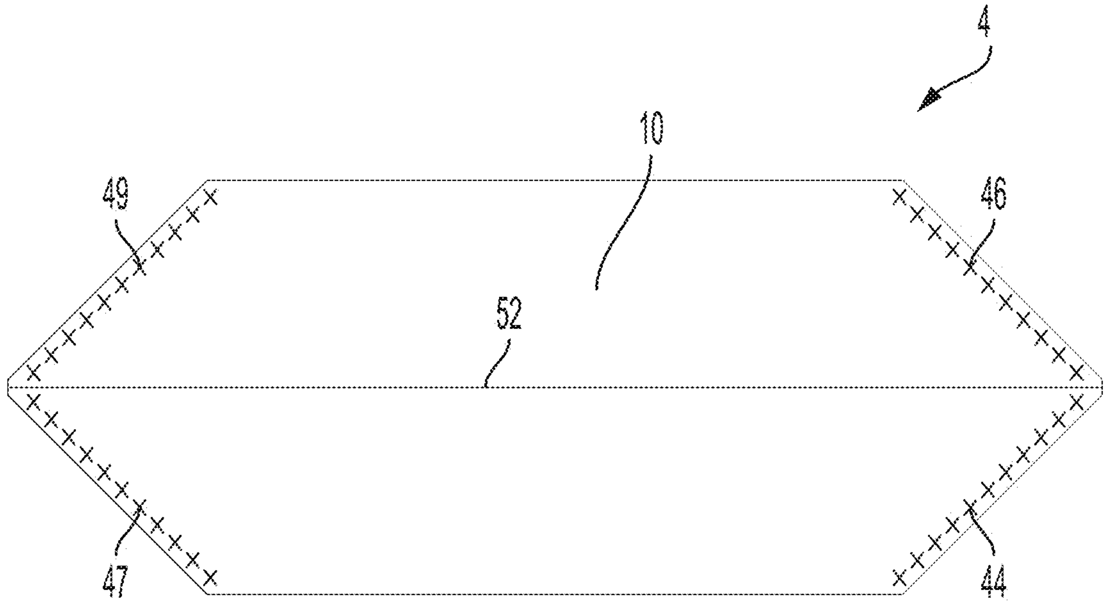
FIG. 10F is a bottom view of the bag of FIG. 10A.
Figure 10G:
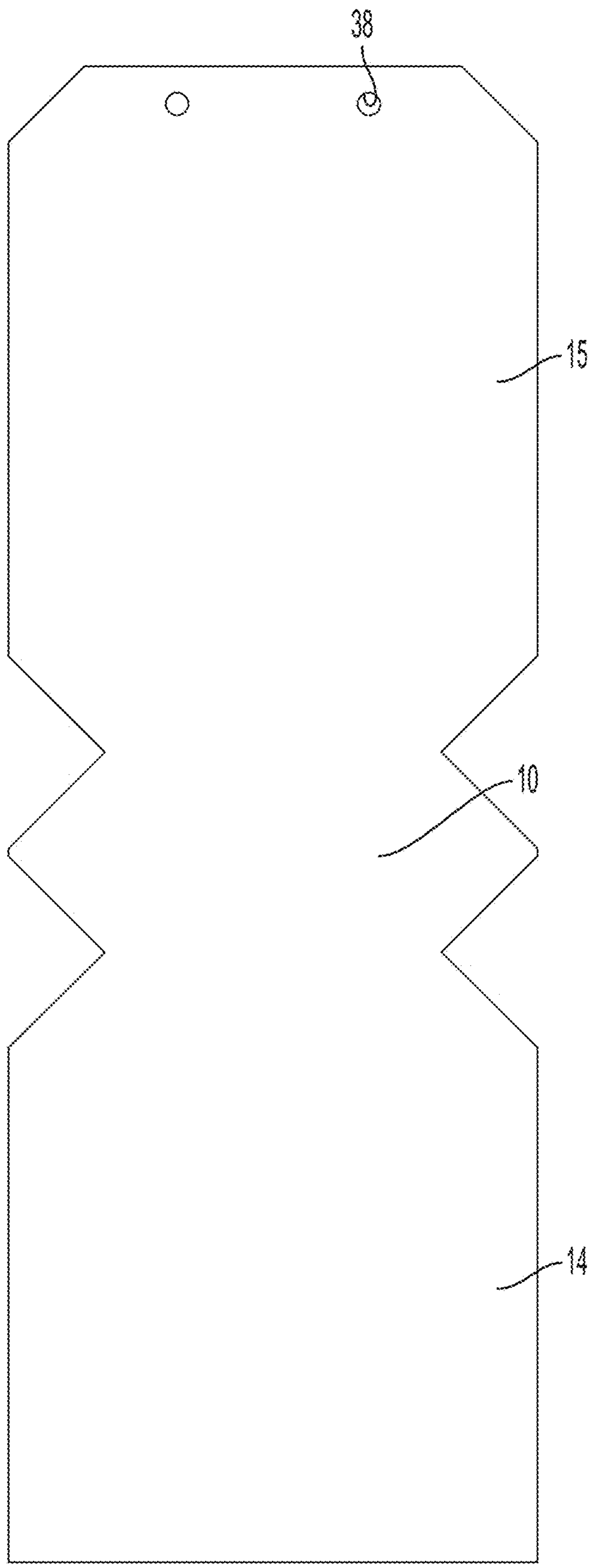
FIG. 10G is a view of a shape of the packaging material used to produce the bag of FIG. 10A.

An example flattened bag 4—prior to adding one or more absorbent articles and forming the primary seal 2—of the present disclosure is disclosed. The bag 4 may have the configuration illustrated in FIGS. 10A-10F. FIG. 10A is a perspective view of a bag 4 of the present disclosure in a partially flattened configuration and without one or more absorbent articles within the package. FIG. 10B is a front view of the bag of FIG. 10A. FIG. 10C is a back view of the bag 4 of FIG. 10A. FIG. 10D is right side view of the bag of FIG. 10A, with the left side view being identical. FIG. 10E is a top view of the bag of FIG. 10A. FIG. 10F is a bottom view of the bag of FIG. 10A. FIG. 10G is a view of a shape of the packaging material used to produce the bag 4 of FIG. 10A, the package 1 respectively. Referring to FIGS. 10A-10F, the bag may comprise a fourth surface 14, a fifth surface 15, a left side panel 12 and a right side panel 13 (that are only formed when absorbent articles are within the bag 4, package 1 respectively), a bottom panel 10, and a first and a second part of the top panel 11 (that are formed when absorbent articles are within the package 1 and the package 1 is scaled via the primary seal). Portions of the fourth surface 14 and the fifth surface 15 will eventually form the left 12 and right side panels 13 and the top panel 11 when the package is filled with absorbent articles.

The bag 4 may be designed to have two wicket holes 38. At times, there may be one wicket hole or more than two wicket holes. In an instance, a single wicket hole may form an elongated hole. The portion of the bag 4 having the wicket holes 38 may be cutaway when the package 1 is sealed. As such, consumers will not see the wicket holes 38. In other instances, the bag 4 may be wicketless (i.e., not have one or more wicket holes). Front panel 14, the bottom panel 10, the back panel 15, and the top panel 11 may be formed of a continuous material.

Figure 10H:
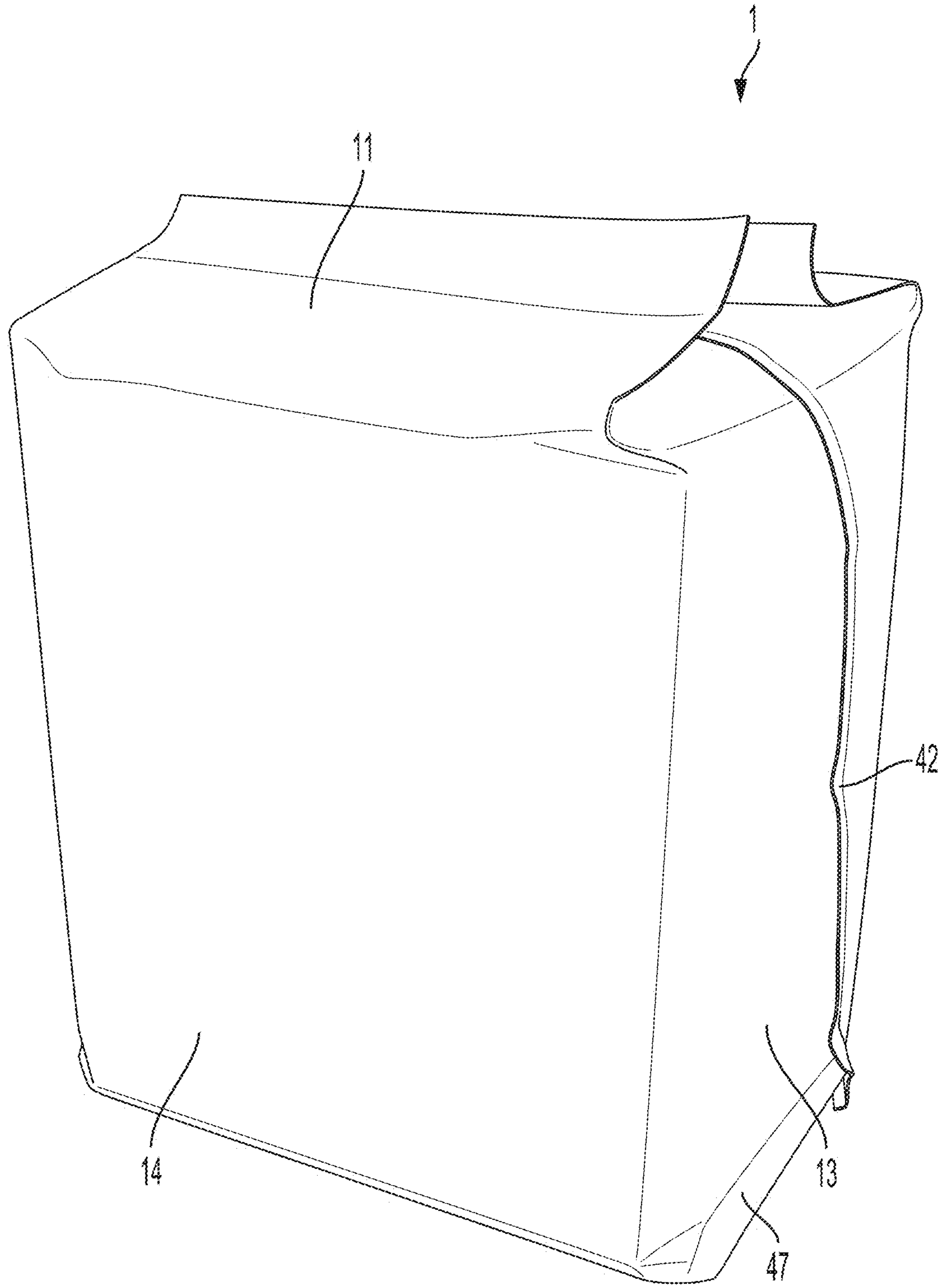
FIG. 10H is a front right side perspective view of an example package with a plurality of absorbent articles positioned therein of the present disclosure.

A vertical left side seam 40 may be formed at the location shown in FIGS. 10A-10C. The vertical left side seam 40, although illustrated in FIGS. 10A-10C as on the fourth surface 14, which forms the front panel 14 of the package 1, and the fifth surface 15, which forms the back panel 15 of the package 1, will be on the left side panel 12 when one or more absorbent articles are added to the bag 4. A vertical right side seam 42 may be formed at the location shown in FIGS. 10A-10C. The vertical right side seam 42, although illustrated in FIGS. 10A-10C as on the fourth surface 14, which forms the front panel 14 of the package 1, and the fifth surface 15, which forms the back panel 15 of the package 1, will be on the right side panel 13 when one or more absorbent articles are added to the bag 4. A first left side angled seam 44 may be formed between portions of the fourth surface 14, the front panel 14 respectively, and portions of the first surface 10, bottom panel 10 respectively. A second left side angled seam 46 may be formed between portions of the fifth surface 15, the back panel 15 respectively, and portions of the first surface 10, bottom panel 10 respectively. A first right side angled seam 47 may be formed between portions of the fourth surface 14, the front panel 14 respectively, and portions of the first surface 10, bottom panel 10 respectively. A second right side angled seam 49 may be formed between portions of the fifth surface 15, the back panel 15 respectively, and portions of the first surface 10, bottom panel 10 respectively. When the bag 4 is filled with one or more absorbent articles, the angled scams 44 and 46 may be formed on the left side panel 12 and the angled scams 48 and 50 may be formed on the right side Panel 13. Any of the seals or scams may form overlap seams and/or butt scams as described herein. The bag 4, package 1 respectively, may also comprise a fold line 52 in first surface 10, bottom panel 10 respectively. FIG. 10H shows an example package 1 of the present disclosure formed from a bag 4 shown in FIGS. 10A-10F.

Package shapes are also contemplated where the package comprises less than six panels. Packages having a circular or semi-circular shape when viewed from a bottom panel are contemplated. Additionally, packages having a triangular shape when viewed from the bottom panel are contemplated. Regardless of the number of panels comprised by the packages of the present disclosure, the package comprises a consumer-facing panel.

Primary Seal

The package 1 comprises a primary seal 2 and the package 1 is scaled by the primary seal such that the one or more absorbent articles 1004 are enclosed within the interior compartment. In particular, the top panel 11 may comprise the primary seal 2. More specifically only the top panel 11 may comprise the primary seal 2. The primary seal 2 may not be reclosable.

A bag 4 for forming a package 1 comprising one or more absorbent articles 1004 is provided. The bag comprises a first surface 10, a second surface 12, a third surface 13, a fourth surface 14 and a fifth surface 15, an open end 48 opposing the first surface 10; wherein one surface selected from the group consisting of the second surface 12, the third surface 13, the fourth surface 14 and the fifth surface 15 comprises a secondary closing element 3, wherein the secondary closing element 3 is reclosable, and two or more surfaces selected from the group consisting of second surface 12, the third surface 13, the fourth surface 14 and the fifth surface 15 comprise a primary scaling area to form a primary seal 2. In particular, the bag 4 may be filled by inserting articles, such as a plurality of absorbent articles, through the open end 48 and the open end 48 is then closed by the primary seal 2 to form a sixth surface 11. Hence, by creating the primary seal 2 and thus closing the bag 4, a package comprising a front panel 14, a back panel 15 opposite the front panel 14, a first side panel 12, a second side panel 13 opposite the first side panel 12, a top panel 11, and a bottom panel 10 opposite the top panel 11 is formed. The panels define an interior compartment of the package 1 and one or more absorbent articles 1004 are disposed in the interior compartment. The package 1 comprises a secondary closing element 3 and the secondary closing element 3 is reclosable.

In a form, the sixth surface 11, top panel 11 respectively, may comprise closing gussets 11*b*, wherein portions of the outer surface of the package material at the closing gussets 11*b* are brought together to form a closing seam 11*a* and a closing seam fin 11*c* extending from the closing scam 11*a*, and sixth surface 11. At least a portion of the closing seam fin 11*c* may be attached to at least a portion of the sixth surface 11. Tacking down the closing seam fin 11*c* to at least a portion of the sixth surface may reduce the risk of unintentional opening of the package, provide for increased stackability, as well provide a cleaner look on-shelf look. The primary seal 2 may be configured to completely close the distance between the two gussets 11*b* of the top panel 11. In other words, the primary seal 2 may be configured to close 100% of the distance between the two gussets 11*b* of the top panel 11. The primary seal 2 may correspond to the closing seam 11*a*.

The primary seal 22 may comprise an adhesive. The type of adhesives utilized for the seals including the primary seal 2 of the packages of the present disclosure may impact the recyclability of the package as well. As an example, adhesives that can dissolve in water during the re-pulping step or the disintegration step of the paper recycling process may be particularly suitable for the packages of the present disclosure. Such adhesives include starch based adhesives, polyvinyl acetate based adhesives, and polyethylene oxide based adhesives. A suitable example of a starch based adhesive is available from LD Davis located in Monroe, North Carolina, under the trade name AP0420CR. A suitable example of a polyvinyl acetate based adhesive is available from Sekisui Chemical Company, located in Osaka, Japan, under the trade name Selvol 205. A suitable example of a polyethylene oxide based adhesive is available from Dow Chemicals Co. located in Midland, Michigan, under the trade name WSR N-80.

Water-dispersible adhesives may similarly be utilized. Suitable examples of water dispersible adhesives include thermoplastic elastomer based adhesives and polyvinyl acetate based adhesives. A suitable example of a thermoplastic elastomer based adhesive is available from Actega located in Blue Ash, Ohio, under the trade name Yunico 491. A suitable example of a polyvinyl acetate based adhesive is available from Bostik located in Milwaukee, Wisconsin, under the trade name Aquagrip 4419U01. Another suitable example of a polyvinyl acetate based adhesive is available from HB Fuller under the trade name PD-0330.

Without wishing to be bound by theory, it is believed that packages of the present disclosure which utilize adhesives dissolvable in water may comprise a higher weight percentage of such adhesives than adhesive which are only water dispersible. For example, packages comprising water dissolvable adhesives may comprise a first weight percentage of adhesive while packages comprising water dispersible adhesives may comprise a second weight percentage of adhesive. The first weight percentage may be greater than the second weight percentage for the purposes of recycling the package material.

The primary sealing area of the bag 4 in general is the area in which the primary seal 2 is formed and thereby the package 1 is formed. In particular, the primary sealing area may comprise means, in particular adhesive to form the primary seal 2. Two or more surfaces selected from the group consisting of the second surface 12, the third surface 13, the fourth surface 14 and the fifth surface 15 comprise a primary sealing area to form a primary seal 2, in particular the second surface 12, the third surface 13, the fourth surface 14 and the fifth surface 15 may each comprise a primary sealing area to form a primary seal 2.

Figure 3A:
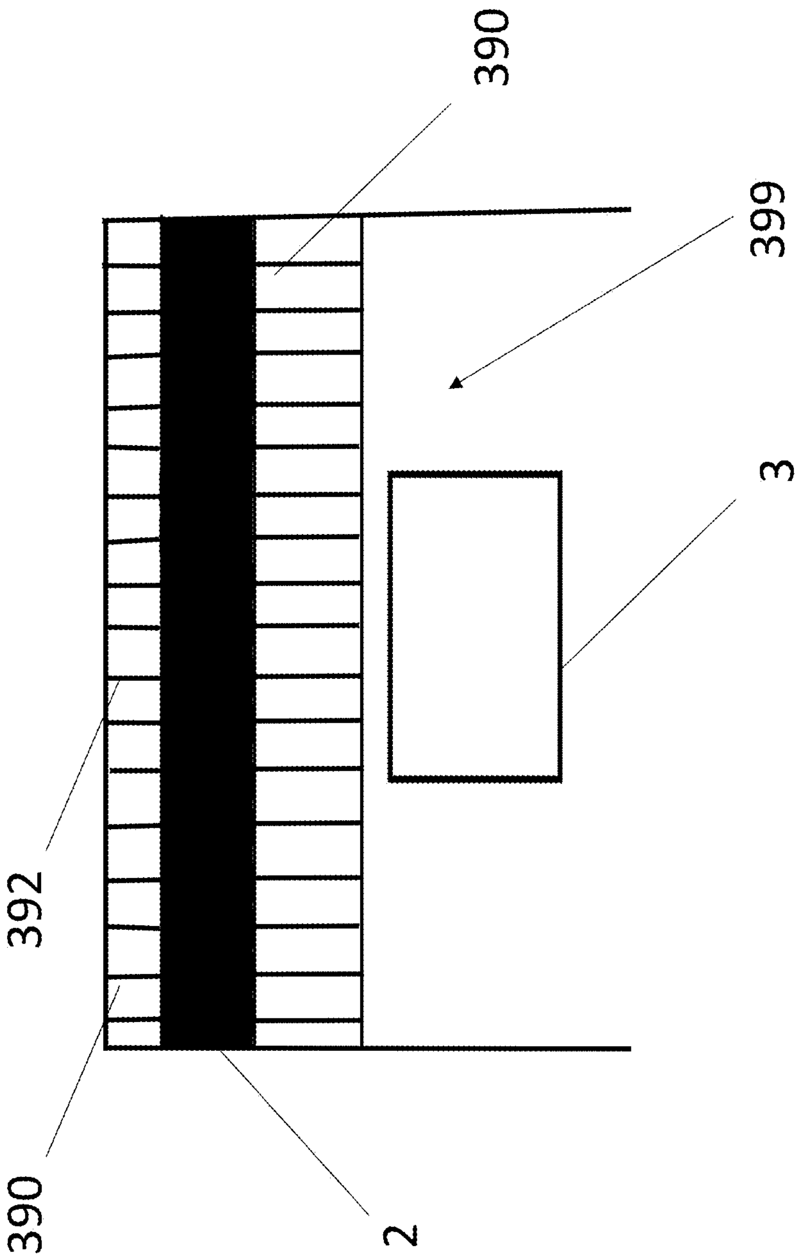
FIG. 3A is a schematic representation showing a panel of a package of the present disclosure, wherein the inner surface of the panel comprises a primary seal and a secondary closing element with an adhesive area and hidden edges identified.

Regarding FIG. 3A, an inner surface 399 with the primary seal 2 and a rectangular secondary closing element 3 of the packages 1 of the present disclosure is shown. The primary seal 2 may exemplarily be formed in an adhesive area 390. The secondary closing element 3 may overlap with the adhesive area 390 or may be separate to the adhesive area. The adhesive area 390 may correspond to the primary sealing area of the bag 4. As discussed previously, the adhesive provided for the primary sealing area of the bag 4, the adhesive area 390 respectively, may be provided in a pattern or a full coat. The adhesive area 390 as shown, comprises an upper portion and a lower portion which flank the primary seal 2. Adhesive 392 is shown applied in stripes in the adhesive area 390. Prior to the formation of the primary seal 2, the adhesive stripes 392 are configured similarly in the seal area 380 as they are in the adhesive area 390.

Figure 3B:
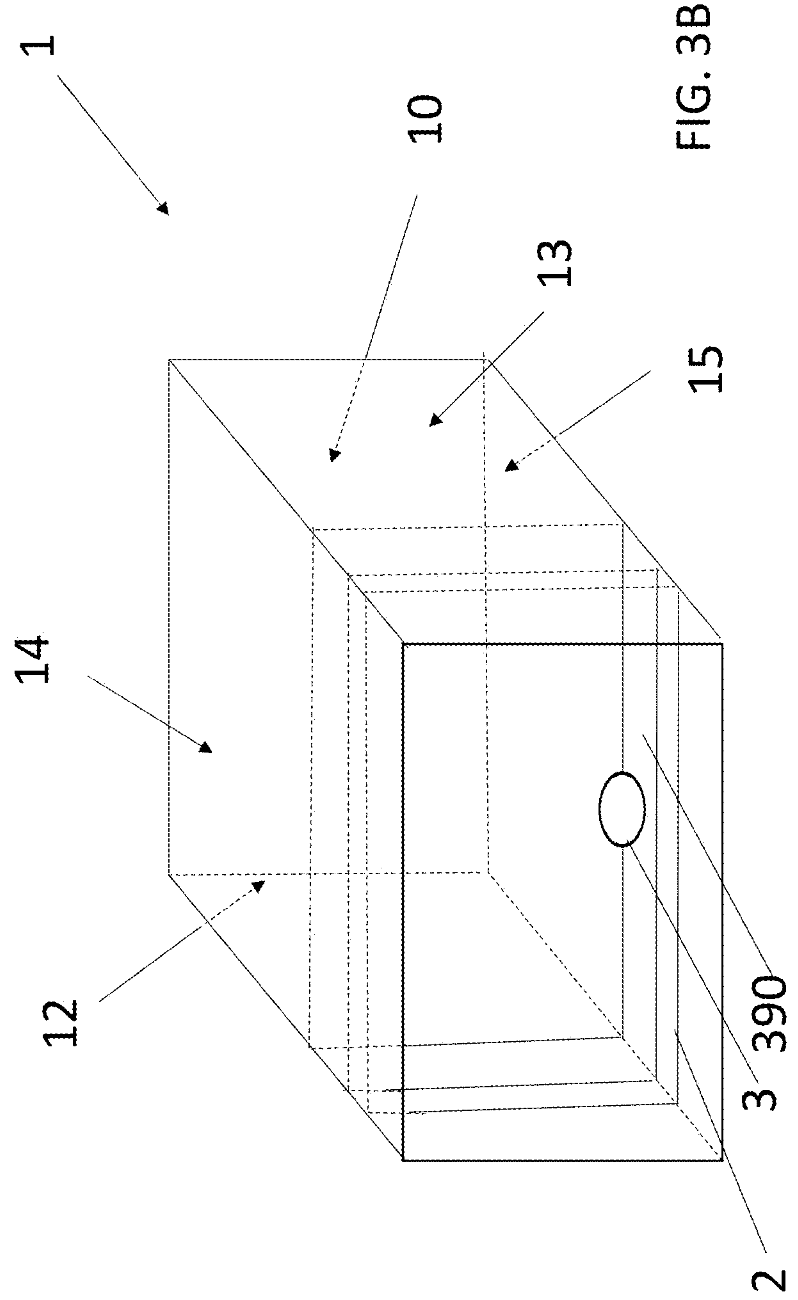
FIG. 3B is a schematic representation showing a package of the present disclosure with a primary seal, a secondary closing element and an adhesive area seal.

In FIG. 3B a package 1 of the present disclosure with the primary seal 2 and an oval secondary closing element 3 overlapping with the adhesive area 390 is shown. The primary scaling area in the bag 4 and thus the adhesive area 390 and the primary seal 2 in the package 1 may be provided on the inner surface of the package 1 completely around the periphery. The full coverage, i.e. 360 degrees is not necessarily required, but it may be provided as shown. Note that adjacent the sides 12 and 13, gaps in the adhesive may be provided to ensure that when compressed an excess amount of adhesive is not present in the primary seal 2 being formed. Such gaps in the adhesive can reduce the likelihood of the adhesive spilling out of the package and/or contaminating the packaging equipment.

Figure 3C:
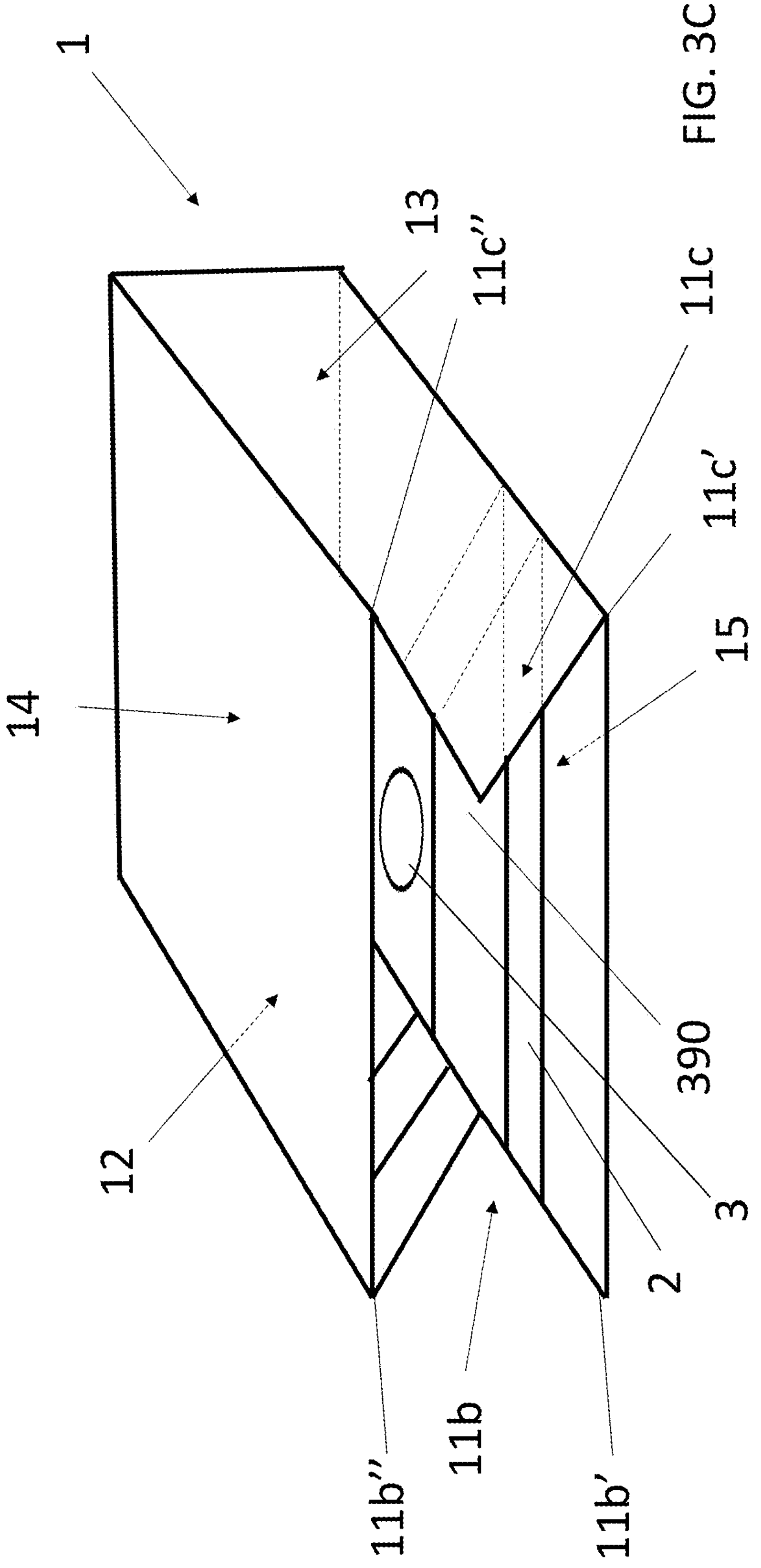
FIG. 3C is a schematic representation showing a package similar to the package of FIG. 3B except for the secondary closing element location.

In FIG. 3C a package 1 of the present disclosure with the primary seal 2 and an oval secondary closing element 3 not overlapping with the adhesive area 390 is shown. Upon formation of the primary seal 2, the seal may be formed between the fourth and fifth surfaces 14 and 15, a gusset may be created in the second surface 12 and the third surface 13. See gussets 11*b* and 11*c* of FIG. 1D. The adhesive provided on the inner surface of the package 1, would be sufficient to seal the one or more absorbent articles therein. However, if desired, additional adhesive may be provided on the outer surface adjacent the gussets 11*b* and 11*c* in the second surface 12 and the third surface 13. The adhesive on the outer surface can allow for gusset fins 11*b*' and 11*b*" as well as 11*c*' and 11*c*" to be joined together. Such configuration can allow for a more finished look of the packages of the present disclosure. However, the adhesive on the outer surface to join the gusset fins together is optional.

The primary seal 2 may exhibit a Normalized Average Peel Force at first peel of at least 50 mN/mm, preferably at least 60 mN/mm, more preferably at least 80 mN/mm, even more preferably at least 90 mN/mm or even at least 100 mN/mm according to the Seal Strength Test Method disclosed herein. The primary seal 2 may exhibit a Normalized Average Peel Force of between 50 mN/mm and 600 mN/mm, preferably between 60 mN/mm and 500 mN/mm, more preferably between 80 mN/mm and 400 mN/mm, even more preferably between 90 mN/mm and 300 mN/mm or even between 100 mN/mm and 250 mN/mm according to the Seal Strength Test Method disclosed herein.

The primary seal 2 may exhibit a Normalized Peak Load at first peel of at least 100 mN/mm, preferably at least 150 mN/mm, more preferably at least 200 mN/mm, even more preferably at least 250 mN/mm or even at least 300 mN/mm according to the Seal Strength Test Method disclosed herein. The primary seal 2 may exhibit a Normalized Peak Load of between 100 mN/mm and 1000 mN/mm, preferably between 150 mN/mm and 800 mN/mm, more preferably between 200 mN/mm and 600 mN/mm, even more preferably between 250 mN/mm and 500 mN/mm or even between 300 mN/mm and 400 mN/mm according to the Seal Strength Test Method disclosed herein.

The primary seal 2 may exhibit a Normalized Peel Energy of at least 500 mN/mm, preferably at least 700 mN/mm, more preferably at least 800 mN/mm, even more preferably at least 900 mN/mm or even at least 1000 mN/mm according to the Seal Strength Test Method disclosed herein. The primary seal 2 may exhibit a Normalized Peel Energy of between 500 mN/mm and 2000 mN/mm, preferably between 700 mN/mm and 1800 mN/mm, more preferably between 800 mN/mm and 1600 mN/mm, even more preferably between 900 mN/mm and 1500 mN/mm or even between 1000 mN/mm and 1300 mN/mm according to the Seal Strength Test Method disclosed herein.

The primary seal 2 may exhibit one or more property selected from the group consisting of:

a) a Normalized Average Peel Force of between 50 mN/mm and 600 mN/mm, preferably between 60 mN/mm and 500 mN/mm, more preferably between 80 mN/mm and 400 mN/mm, even more preferably between 90 mN/mm and 300 mN/mm or even between 100 mN/mm and 250 mN/mm;

b) a Normalized Peak Load of between 100 mN/mm and 1000 mN/mm, preferably between 150 mN/mm and 800 mN/mm, more preferably between 200 mN/mm and 600 mN/mm, even more preferably between 250 mN/mm and 500 mN/mm or even between 300 mN/mm and 400 mN/mm according to the Seal Strength Test Method disclosed herein; and c) a Normalized Peel Energy of between 500 mN/mm and 2000 mN/mm, preferably between 700 mN/mm and 1800 mN/mm, more preferably between 800 mN/mm and 1600 mN/mm, even more preferably between 900 mN/mm and 1500 mN/mm or even between 1000 mN/mm and 1300 mN/mm according to the Seal Strength Test Method disclosed herein.

By such a Normalized Average Peel Force, Normalized Peak Load and/or Normalized Peel Energy it is assured that the primary seal 2 is strong enough to not unintentionally be opened during transport, storage etc. while still being readily openable by the user without damaging the package material.

Secondary Closing Element

The package 1 comprises a secondary closing element 3. The secondary closing element 3 is reclosable. The secondary closing element 3 may comprise a reclosing means selected from the group consisting of an adhesive, a cohesive, and a mechanical fastener. Exemplary mechanical fasteners may be a hook-loop fastener, a button, a zip-lock and a tab-slot fastener. The top panel 11 may comprise the secondary closing element 3.

In particular, the secondary closing element 3 may comprise an adhesive in the form of a double-sided tape. One side of the double-sided tape may be adhered to the package prior to opening, while the other side may be unattached to the package. Different forms of double-sided tapes are known in the art and may be chosen depending on the application and corresponding desired properties such as adhesion strength, humidity resistance etc. The unattached side of the double-sided tape may be covered by a release liner. Alternatively, the secondary closing element 3 may comprise an adhesive, for example in the form of a stripe, having two adhesive surfaces, one of which is adhered to the package 1 and the other is covered by a release liner The release liner may be manually removed by the consumer after first opening of the package 1, first opening of the primary seal 2 respectively, to activate the secondary closing element 3. Alternatively, the release liner may automatically be removed upon first opening of the package 1, first opening of the primary seal respectively, to activate the secondary closing element 3. Generally, the secondary closing element 3 may be activated to become closable, reclosable respectively, upon or after first opening of the primary seal 2. Exemplarily, an adhesive comprised by the secondary closing element 3 may be activated by exposure to the environmental humidity.

In one embodiment, the inner surface of the package 1 opposing the secondary closing element 3 may comprise a receptive area. Respectively, the inner surface of the bag 4 opposing the secondary closing element 3 may comprise a receptive area. Exemplarily, the secondary closing element 3 may comprise an adhesive and the inner surface of the package 1 opposing the secondary closing element 3 may comprise a receptive area. The secondary closing element 3 may adhere to the receptive area, when the package is reclosed after first opening. In particular, secondary closing element 3 may adhere to the receptive area without adhering directly to the packaging material. The receptive area may have a different surface than the rest of the inner surface of the package. In particular, the receptive area may be an area of the inner surface of the package comprising a coating. Coatings may exemplarily be polyolefin based coating, in particular polyethylene coatings, or siliconized coatings.

The package 1 may be sealed by the primary seal such that the secondary closing element 3 is enclosed within the package 1. As such, the secondary closing element 3 is not exposed to environmental insults such as humidity and/or dust. The secondary closing element 3 may be located closer to the one or more absorbent articles 1004 than the primary seal 2. The volume of the interior compartment 1002 when closed via the secondary closing element 3 may be at least 70%, preferably at least 80%, preferably at least 90%, more even preferably at least 95% or even 100% of the volume of the interior compartment 1002 when closed via the primary seal 2.

The secondary closing element 3 may partially or completely be located in between two gussets 11*c* in the top panel 11. In such a configuration, the package favorably retains its original shape after opening such that the package can easily be reclosed via the secondary closing element 3. Due to such a configuration, the width of the secondary closing element 3 can be reduced while still closing a large portion of the opening created by breaking the primary seal 2. Thus, the secondary closing element may be configured to close at least 60%, preferably at least 70%, more preferably at least 80%, even more preferably at least 90%, even more preferably at least 95% or even 100% of the distance between the two gussets 11*b* of the top panel 11. The secondary closing element 3 may have a width of at least 60%, preferably at least 70%, more preferably at least 80%, even more preferably at least 90% or even at least 95% of the distance between the two gussets in the top panel 11. The distance between the two gussets in the top panel is measured in the dimension parallel to the edge between the front panel 14 and top panel 11 and corresponds to the maximum distance between the two edges of the gussets facing each other.

Generally, the dimensions of the secondary closing element 3 may play an important role in the closing performance, represented by the Normalized Average Peel Force, Normalized Peak Load and/or Normalized Peel Energy, but also influence the recyclability, as the materials of the secondary closing element 3 may potentially not be recycled in the same recycling stream as the packaging material. The secondary closing element may have a maximum width from 0.5 cm to 30 cm, preferably from 1 cm to 25 cm, more preferably from 2 cm to 20 cm, even more preferably from 3 cm to 15 cm or even from 5 cm to 10 cm. The secondary closing element may have a maximum height from 0.2 cm to 6 cm, preferably from 0.3 cm to 5 cm, more preferably from 0.5 cm to 4 cm, even more preferably from 0.7 cm to 3 cm or even from 1 cm to 2 cm. The width corresponds to the distance between opposing edges of the secondary closing element 3 in a dimension parallel to the edge between the front panel and the top panel of the package 1, and the height to the distance between opposing edges of the secondary closing element 3 in a dimension perpendicular to the edge between the front panel and the top panel of the package 1. Width and height are measured utilizing a ruler. The secondary closing element 3 may have a total area from 0.1 $cm^2$ to 100 $cm^2$, preferably from 1 $cm^2$ to 80 $cm^2$, more preferably from 2 $cm^2$ to 60 $cm^2$, even more preferably from 5 $cm^2$ to 50 $cm^2$ or even from 10 $cm^2$ to 30 $cm^2$.

The secondary closing element 3 may be smaller in width than the primary seal 2. The secondary closing element 3 may have a width from 20% to 90%, preferably from 30% to 80%, more preferably from 40% to 70% or even from 50% to 60% of the width of the primary seal 2. While the primary seal 2 may completely close the open end 48 of the bag 4 to enclose the absorbent articles 1004 to prevent any contamination during transport and on display on a store shelf, the secondary closing element may only partially close the package after first opening for a sufficient protection from environmental insults due to the reduced duration and typically reduced amount of environmental stress at the consumer. On the other hand, while the primary seal 2 can be precisely generated at the manufacturing line, the secondary closing element 3 has to provide some tolerance for the opposing surfaces being displaced in respect to one another for the consumer to reclose the package via the secondary closing element 3. In addition, parts of the secondary closing element located closer to the opening may get deactivated by environmental insults after opening. The secondary closing element 3 may have a height from 120% to 3000%, preferably from 200% to 2000%, more preferably from 300% to 1000% or even from 400% to 800% of the height of the primary seal 2.

The package 1 may comprise a weakened region disposed in the package material configured to form an opening. Hence, the primary seal 2 does not necessarily have to be broken to open the package. The weakened region may be located between the primary seal 2 and the secondary closing element. By this, reclosability of the package via the secondary closing element 3 is ensured.

The secondary closing element 3 may exhibit a Normalized Average Peel Force at first peel of at most 500 mN/mm, preferably at most 400 mN/mm, more preferably at most 350 mN/mm, even more preferably at most 300 mN/mm or even at most 250 mN/mm according to the Seal Strength Test Method disclosed herein. The secondary closing element may exhibit a Normalized Average Peel Force at first peel of between 50 mN/mm and 500 mN/mm, preferably between 60 mN/mm and 400 mN/mm, more preferably between 80 mN/mm and 350 mN/mm, even more preferably between 90 mN/mm and 300 mN/mm or even between 100 mN/mm and 250 mN/mm according to the Seal Strength Test Method disclosed herein. The secondary closing element 3 may exhibit a Normalized Average Peel Force at fifth peel of from 60% to 100%, preferably 70% to 99%, more preferably from 80% to 95% of the Normalized Average Peel Force at first peel according to the Seal Strength Test Method disclosed herein. The secondary closing element may exhibit a Normalized Average Peel Force at fifth peel between 30 mN/mm and 600 mN/mm, preferably between 40 mN/mm and 500 mN/mm, more preferably between 50 mN/mm and 400 mN/mm, even more preferably between 60 mN/mm and 350 mN/mm or even between 80 mN/mm and 300 mN/mm according to the Seal Strength Test Method disclosed herein. The secondary closing element 3 may exhibit a Normalized Average Peel Force at first peel of from 60% to 500%, preferably 70% to 400%, more preferably from 80% to 300%, or even from 100% to 250% of the Normalized Average Peel Force of the primary seal 2 according to the Seal Strength Test Method disclosed herein.

The secondary closing element 3 may exhibit a Normalized Peak Load at first peel of at most 900 mN/mm, preferably at most 800 mN/mm, more preferably at most 700 mN/mm, even more preferably at most 600 mN/mm or even at most 500 mN/mm according to the Seal Strength Test Method disclosed herein. The secondary closing element may exhibit a Normalized Peak Load at first peel of between 80 mN/mm and 900 mN/mm, preferably between 100 mN/mm and 800 mN/mm, more preferably between 150 mN/mm and 700 mN/mm, even more preferably between 200 mN/mm and 600 mN/mm or even between 250 mN/mm and 500 mN/mm according to the Seal Strength Test Method disclosed herein. The secondary closing element 3 may exhibit a Normalized Peak Load at fifth peel of 60% to 100%, preferably 70% to 99%, more preferably from 80% to 95% of the Normalized Average Peak Load at first peel according to the Seal Strength Test Method disclosed herein. The secondary closing element 3 may exhibit a Normalized Peak Load at fifth peel between 50 mN/mm and 1000 mN/mm, preferably between 60 mN/mm and 900 mN/mm, more preferably between 80 mN/mm and 800 mN/mm, even more preferably between 100 mN/mm and 700 mN/mm or even between 150 mN/mm and 600 mN/mm according to the Seal Strength Test Method disclosed herein. The secondary closing element 3 may exhibit a Normalized Peak Load at fifth peel between 30 mN/mm and 600 mN/mm, preferably between 40 mN/mm and 500 mN/mm, more preferably between 50 mN/mm and 400 mN/mm, even more preferably between 60 mN/mm and 350 mN/mm or even between 80 mN/mm and 300 mN/mm according to the Seal Strength Test Method disclosed herein. The secondary closing element may exhibit a Normalized Peak Load at first peel of from 60% to 400%, preferably 70% to 300%, more preferably from 80% to 200% of the Normalized Average Peak Load of the primary seal 2 according to the Seal Strength Test Method disclosed herein.

The secondary closing element 3 may exhibit a Normalized Peel Energy at first peel of at most 1500 mN/mm, preferably at most 1200 mN/mm, more preferably at most 1000 mN/mm, even more preferably at most 900 mN/mm or even at most 800 mN/mm according to the Seal Strength Test Method disclosed herein. The secondary closing element 3 may exhibit a Normalized Peel Energy at first peel of between 250 mN/mm and 1500 mN/mm, preferably between 300 mN/mm and 1200 mN/mm, more preferably between 400 mN/mm and 1000 mN/mm, even more preferably between 450 mN/mm and 900 mN/mm or even between 500 mN/mm and 800 mN/mm according to the Seal Strength Test Method disclosed herein. The secondary closing element 3 may exhibit a Normalized Peel Energy at fifth peel of from 60% to 100%, preferably 70% to 99%, more preferably from 80% to 95% of the Normalized Peel Energy at first peel according to the Seal Strength Test Method disclosed herein. The secondary closing element 3 may exhibit a Normalized Peel Energy at fifth peel between 150 mN/mm and 1800 mN/mm, preferably between 200 mN/mm and 1500 mN/mm, more preferably between 250 mN/mm and 1200 mN/mm, even more preferably between 300 mN/mm and 1000 mN/mm or even between 400 mN/mm and 900 mN/mm according to the Seal Strength Test Method disclosed herein. The secondary closing element 3 may exhibit a Normalized Peel Energy at first peel of from 50% to 200%, preferably 60% to 150%, more preferably from 70% to 120% or even from 80% to 100% of the Normalized Peel Energy of the primary seal 2 according to the Seal Strength Test Method disclosed herein.

The secondary closing element 3 may exhibit one or more property selected from the group consisting of:

a) a Normalized Average Peel Force at first peel of between 50 mN/mm and 500 mN/mm, preferably between 60 mN/mm and 400 mN/mm, more preferably between 80 mN/mm and 350 mN/mm, even more preferably between 90 mN/mm and 300 mN/mm or even between 100 mN/mm and 250 mN/mm according to the Seal Strength Test Method disclosed herein;

b) a Normalized Average Peel Force at fifth peel between 30 mN/mm and 600 mN/mm, preferably between 40 mN/mm and 500 mN/mm, more preferably between 50 mN/mm and 400 mN/mm, even more preferably between 60 mN/mm and 350 mN/mm or even between 80 mN/mm and 300 mN/mm according to the Seal Strength Test Method disclosed herein;

c) a Normalized Peak Load at first peel of between 80 mN/mm and 900 mN/mm, preferably between 100 mN/mm and 800 mN/mm, more preferably between 150 mN/mm and 700 mN/mm, even more preferably between 200 mN/mm and 600 mN/mm or even between 250 mN/mm and 500 mN/mm according to the Seal Strength Test Method disclosed herein;

d) a Normalized Peak Load at fifth peel between 30 mN/mm and 600 mN/mm, preferably between 40 mN/mm and 500 mN/mm, more preferably between 50 mN/mm and 400 mN/mm, even more preferably between 60 mN/mm and 350 mN/mm or even between 80 mN/mm and 300 mN/mm according to the Seal Strength Test Method disclosed herein c) a Normalized Peel Energy at first peel of between 500 mN/mm and 2000 mN/mm, preferably between 700 mN/mm and 1800 mN/mm, more preferably between 800 mN/mm and 1600 mN/mm, even more preferably between 900 mN/mm and 1500 mN/mm or even between 1000 mN/mm and 1300 mN/mm according to the Seal Strength Test Method disclosed herein; and f) a Normalized Peel Energy at fifth peel between 150 mN/mm and 1800 mN/mm, preferably between 200 mN/mm and 1500 mN/mm, more preferably between 250 mN/mm and 1200 mN/mm, even more preferably between 300 mN/mm and 1000 mN/mm or even between 400 mN/mm and 900 mN/mm according to the Seal Strength Test Method disclosed herein.

By such a Normalized Average Peel Force, Normalized Peak Load and/or Normalized Peel Energy it is assured that the secondary closing element 3 is strong enough to withstand typical forces and not unintentionally be opened during transport, storage etc. while still being readily openable by the user without damaging the package material. The secondary closing element 3 may be chosen to retain its Normalized Average Peel Force, Normalized Peak Load and/or Normalized Peel Energy upon several openings to ensure a good reopening/reclosing performance. A measure for such performance retention is the Normalized Average Peel Force, Normalized Peak Load and/or Normalized Peel Energy at fifth peel.

Package Materials

The package materials of the present disclosure comprise natural fibers. The package materials of the present disclosure may comprise wood fiber and/or pulp fiber. The package materials may comprise at least 50 percent by weight natural fibers, at least 70 percent by weight natural fibers, at least 90 percent by weight natural fibers, between about 50 percent and about 100 percent by weight natural fibers, between about 65 percent and about 99 percent by weight natural fibers, or between about 75 percent and about 95 percent by weight of natural fibers, specifically reciting all values within these ranges and any ranges formed therein or thereby. In one form, the package materials may comprise 99.9% percent by weight natural fibers. By having such content of natural fibers, the package material may exhibit sufficient strength to not collapse upon opening and removal of one or more absorbent articles 1004.

Inks and/or dyes associated with the package art, branding, package information, and/or background color, as well as adhesives associated with the seams and barrier coatings are also considered part of the package materials on a weight percentage basis. Where the weight percentage of natural fibers is less than 100 percent, the difference may be made up by inks, dyes, and/or adhesives. Inks, dyes, coatings, and adhesives may be considered contaminants in a paper recycling process, but may be otherwise recyclable.

While the package materials may comprise many different fibers, inks, dyes, coatings, adhesives, etc., the package material of the present disclosure may be constructed to facilitate and/or encourage recycling of the package material, and may encourage recycling of the package material within a single recycling stream, such as a paper recycling stream. Whether package materials are recyclable may vary from region to region. In order to meet one of the highest standards for recyclability, the total weight percentage of non-recyclable material, including material not recyclable within a particular recycling stream-such as a paper recycling stream—but otherwise recyclable, e.g. inks, dyes, adhesives, and coatings in the package material may be 5 percent by weight of the package material or less, or between 0.1 percent to 5 percent by weight, specifically reciting all values within these ranges and any ranges formed therein. However, other jurisdictions may allow a higher weight percentage of non-recyclable material. For example, in other jurisdictions, the package material of the present disclosure may comprise 50 percent by weight or less, 30 percent by weight or less, or about 15 percent by weight or less of non-recyclable material, specifically including all values within these ranges and any ranges formed therein or thereby. As another example, the package materials of the present disclosure may comprise from between about 0.1 percent to about 50 percent by weight, from about 0.1 percent to about 30 percent by weight, or from about 0.1 percent to about 15 percent by weight of non-recyclable material, specifically including all values within these ranges and any ranges formed therein or thereby. In an example, the amount of inks, dyes, coatings, and adhesives is 5 percent by weight, or less, or between 0.1 percent by weight to 5 percent by weight, specifically reciting all values within these ranges and any ranges formed therein.

The package materials of the present disclosure may be free of a barrier layer. As used herein, the term "barrier layer" refers to a layer of material, including barrier coatings, barrier plastics, and/or barrier foils, that is joined to the package materials comprising natural fibers. Such barrier layers may reduce the recyclability of the package materials within a single recycling stream.

In other instances, in order to at least partially protect absorbent articles disposed within the package, the package materials of the present disclosure may comprise a barrier layer. The barrier layer may at least partially inhibit the migration of water vapor through the package material. The barrier layer may comprise a water soluble material that may not interfere with a recycling process. The barrier layer may be easily separable from the remainder of the package materials through a recycling process, for example by having a different water solubility, density, buoyancy, or other physical features as compared to the remainder of the package materials.

Where a barrier layer is utilized, the barrier material may be selected such that the use of adhesives can be reduced or eliminated. One such barrier material may be polyethylene film coated on an inner surface of the package material. The polyethylene may be utilized to form the seals rather than an adhesive or in conjunction with an adhesive. However, as the polyethylene film may not be recyclable in the same stream as the other package materials, the weight percentage of the polyethylene may be in accordance with the present description regarding percentages of non-recyclable material discussed herein.

The higher the percent yield of natural material, the more likely the material is able to be recycled in a paper recycling stream. In order to accommodate the higher percent yield of natural material, e.g. wood pulp and/or cellulose, the weight percentage of barrier layer compared to that of the natural fiber should be substantially less. The barrier layer may comprise one or more barrier film layers. The one or more barrier film layers may be polyethylene film layers. As an example, one or more barrier film layers can make up about 40 percent by weight or less, about 30 percent by weight or less, about 20 percent by weight or less, about 10 percent by weight or less, about 5 percent by weight or less, or about 5 percent to about 20 percent, of the overall package material. As another example, one or more barrier film layers can make up from 15 between about 3 percent by weight to about 40 percent by weight, from about 3 percent by weight to about 30 percent by weight, or from about 3 percent by weight to about 20 percent by weight. In one specific example, one or more barrier film layers may make up about 5 percent by weight or less of the overall package material weight, about 4 percent or less, or about 3 percent or less. In another specific example, the film may make up from between about 1 percent by weight to 20 about 5 percent by weight, from about 1 percent by weight to about 4 percent by weight, or from about 1 percent by weight to about 3 percent by weight.

The one or more barrier layers or one or more barrier film layers may comprise the natural fibers being coated with clay, hectorite, and/or PET that is not scalable, but does provide a suitable barrier. Another option would be to join metalized paper, or other inorganic barrier material, to the natural fibers, which again provides a suitable barrier. Aluminiumoxide barriers or layers are also contemplated to be joined to or indirectly attached to or deposited on the natural fibers. The Aluminiumoxide barriers are transparent which may be desirable and/or less noticeable to consumers. With all of these options, bonding enhancement agents may be applied to seal and/or scam areas on the inner surface of the package material to allowed seals or seams to be formed when the package is made even though the initial barrier materials are not scalable. An example of a bonding enhancement agent is a heat sealable adhesive, a thermoplastic polymer, a hot melt polymer, water based adhesive, a coextruded polymeric layer, or combinations thereof. Bonding enhancement agents may be flexo-printed, dispersion coated, applied by ink jet printing, or applied using any other specific application technology. In general, the clay, hectorite, PET, metalized paper, inorganic barriers, and/or aluminiumoxide, including the bonding enhancement agents in the seal or seam areas may be less than about 15%, less than about 10%, less than about 5%, about 2% to about 10%, or about 3% to about 8%, by weight of the laminate of these materials and the natural fibers so as to meet recycling requirements.

The basis weight of the one or more barrier layers may be at least about 2 gsm to less than about 25 gsm. It is theorized that below this basis weight, the film may not cover a sufficient enough portion of the bag to provide a suitable barrier property. However, aside from the foregoing, the one or more barrier film layers may be any suitable basis weight so long as the one or more barrier film layers' basis weight is within the weight percentages described herein. It is worth noting that the one or more barrier film layers laminated, coated, or otherwise joined to the natural fiber layer forms a synergistic relationship particularly where the one or more barrier film layers are desired to be a smaller weight percentage of the overall package material. For example, where the one or more barrier film layers is 5 percent by weight or less of the overall package material, this can be a very small basis weight barrier film layer for the basis weight of package materials described heretofore. At this very low basis weight, it is believed that the one or more barrier film layers would not be able to be processed reliably without being coated, laminated, or otherwise joined to the natural material layer. And similarly, without the addition of the one or more barrier film layers, the natural material layer may not be able to 5 provide much, if any, inhibition to the absorption of moisture vapor by the SAP within the absorbent articles in the package.

The effectiveness of the recycling process on the package material of the present disclosure may be determined via recyclable percentage. Package material of the present disclosure may exhibit recyclable percentages of 60 percent or greater, 75 percent or greater, or 90 percent or greater, specifically reciting all values within these ranges and any ranges formed therein or thereby. The packaging material of the present disclosure may have a recyclable percentage of between about 60 percent and about 99.9 percent, between about 75 percent and about 99.9 percent, or between about 90 percent and about 99.9 percent, specifically reciting all values within these ranges and any ranges formed therein or thereby. In a specific example, the package material of the present disclosure may exhibit a recyclable percentage of between about 95 percent and about 99.9 percent, specifically including all values within these ranges and any ranges formed therein. The recyclable percentage of the package material of the present disclosure is determined via test PTS-RH:021/97 (Draft October 2019) under category II, as performed by Papiertechnische Stiftung located at Pirnaer Strasse 37, 01809 Heidenau, Germany.

Along with recyclable percentage, the total reject percentage is determined via the PTS-RH:021/97 (Draft October 2019) under category II Test Method. The total reject percentage of the package material of the present disclosure may be 40 percent or less, 30 percent or less, or 10 percent or less, specifically including all values within these ranges and any ranges formed therein or thereby. For example, the total rejection percentage of the package material of the present disclosure may be from about 0.5 percent to about 40 percent, from about 0.5 percent to about 30 percent, or from about 0.5 percent to about 10 percent, specifically reciting all values within these ranges and any ranges formed therein or thereby.

It is believed that the percent non-recyclable material does not necessarily have a 1:1 correlation to the total reject percentage. For example, dissolvable adhesives and/or coatings are designed to dissolve during the recycling process. It is theorized that these adhesives may not have an impact the total reject percentage; however, they would contribute to the non-recyclable material weight percent.

The PTS-RH:021/97 (Draft October 2019) under category II Test Method also comprises a visual component. Trained screeners inspect one or more handsheets of recycled package material for visual imperfections. If the number of visual imperfections is too great, then the package material is rejected. If the number of visual imperfections is acceptable, in accordance with the PTS-RH:021/97 (Draft October 2019) under category II Test Method, then the package material is approved for additional processing. The package material of the present disclosure may yield an acceptable level of visual imperfections during this step of the method.

The package material of the present disclosure may yield the recyclable percentages mentioned heretofore as well as pass the visual screening method. Thus, the package material of the present disclosure may achieve an overall score or final outcome of "pass" when subjected to the PTS-RH:021/97 (Draft October 2019) under category II Test Method.

It is also worth noting that there is an alternative method for determining the recyclable percentage of the package material of the present disclosure. The Test Method performed by the University of Western Michigan, called the Repulpability Test Method, may provide a percent yield of recyclable material. While there are subtle differences between the Repulpability Test Method performed by Western Michigan and the PTS-RH:021/97 (Draft October 2019) under category II Test Method, it is believed that the percentage yield of the Repulpability Test Method would be similar to the recyclable percentage provided by the PTS Test Method.

It is contemplated that the package material of the present disclosure, while being recyclable, may itself comprise recycled material. Such determination can be made from a visual inspection of the package. For example, manufacturers typically advertise the use of recycled materials in an effort to demonstrate their eco-friendly product approach. To further expand on this example, some manufacturers may utilize a logo, e.g., a leaf, along with wording to indicate the use of recycled material in the package material. Often times, manufacturers may specify the percentage of recycled material utilized as well, e.g., over 50 percent, over 70 percent, etc.

Visual inspection may be as simple as utilizing the human eye to inspect packages for logos of the use of recycled material. Additionally, or alternatively, visual inspection may include microscopy methods such as optical microscopy, scanning electron microscopy or other suitable methods known in the art. For example, package material comprising recycled paper fibers may appear different under a microscope due to the presence of a much wider range of natural fiber types than if the package material comprised of 100% non-recycled paper. As another example, under a microscope, recycled fibers—due to their increased processing—may appear more fibrillated than their virgin fiber counterparts.

In order to withstand the rigors of a high speed manufacturing process where a plurality of absorbent articles are placed within the package, withstand the force of compressed absorbent articles being placed directly into the package without an intermediate package or container, withstand the rigors of being shipped, provide protection from environmental insults during shipping and while on the store shelf, and provide for product protection while in the consumers home, the package materials may have some level of strength, stretch, and/or resilience. The package materials of the present disclosure may be characterized using metrics such as: MD Tensile Strength in kN/m, CD Tensile Strength in kN/m, MD Stretch At Break in percent, CD Stretch At Break in percent, Burst Strength in kPa, Caliper in μm, MD Tensile Energy Absorption in $J/m^2$, CD Tensile Energy Absorption in $J/m^2$, and Basis Weight in grams per square meter. While all of the metrics may be utilized together to characterize the package materials of the present disclosure, it is believed that some of the metrics alone or in conjunction with others may suffice to characterize package materials which are suitable for packaging absorbent articles. As an example, it is believed that the Burst Strength may be utilized alone or in conjunction with other metrics to obtain package materials which are sufficient for packaging of absorbent articles. Similarly, it is believed that the Tensile Energy Absorption (TEA) in the MD and CD may be utilized in conjunction with one another, and if desired, along with any other combination of the above metrics, to obtain package materials which are suitable for packaging of absorbent articles. As yet another example, it is contemplated that MD Stretch At Break and/or CD Stretch At Break may be utilized in conjunction with at least one of MD Tensile Strength or CD Tensile Strength, respectively, to characterize package materials which may be sufficient to package absorbent articles as described herein. Any suitable combination of metrics may be utilized.

The package materials of the present disclosure may have an MD Tensile Strength of at least 5 kN/m, at least 7 kN/m, or at least 8 kN/m, specifically reciting all values within these ranges and any ranges formed therein or thereby. The MD Tensile Strength may be between about 5 kN/m and about 8.5 kN/m, between about 5.2 kN/m and about 8.2 kN/m, or between about 5.5 kN/m and about 8.0 kN/m, specifically reciting all values within these ranges and any ranges formed therein or thereby. The MD Tensile Strength is measured using the Strength Tensile Test Method described herein.

The package materials of the present disclosure may have a CD Tensile Strength of at least 3 kN/m, at least 4 kN/m, or at least 5.5 kN/m, specifically reciting all values within these ranges and any ranges formed therein or thereby. The CD Tensile Strength may be between about 3 kN/m and about 6.5 kN/m, between about 3 kN/m and about 6.2 kN/m, or between about 3 kN/m and about 6 kN/m, specifically reciting all values within these ranges and any ranges formed therein or thereby. The CD tensile strength is measured using the Strength Tensile Test Method.

The package materials of the present disclosure may have a Burst Strength of at least 200 kPa, at least 250 kPa, or at least 550 kPa, specifically reciting all values within these ranges and any ranges formed therein or thereby. The Burst Strength of the package materials of the present disclosure may be between about 200 kPa and about 600 kPa, between about 220 kPa and about 550 kPa, or between about 250 kPa and about 500 kPa, specifically reciting all values within these ranges and any ranges formed therein or thereby. The Burst Strength is measured using the Burst Strength Test Method described herein. It is believed that the Burst Strength, as measured, includes components of strength, flexibility, and resiliency. As such, it is believed that Burst Strength may be used independently from the other metrics mentioned.

The package materials of the present disclosure, in addition to strength, may also exhibit some measure of resiliency. Thus, the package materials of the present disclosure may exhibit an MD Stretch At Break of at least 3 percent, at least 4 percent, or at least 6 percent, specifically reciting all values within these ranges and any ranges formed therein or thereby. The package materials of the present disclosure may exhibit an MD Stretch At Break of between about 3 percent and about 6.5 percent, between about 3.2 percent and about 6.2 percent, or between about 3.5 percent and about 6 percent, specifically reciting all values within these ranges and any ranges formed therein or thereby. The MD Stretch At Break is measured using the Strength Tensile Test Method described herein.

The package materials of the present disclosure may exhibit a CD Stretch At Break of at least 4 percent, at least 6 percent, or at least 9 percent, specifically reciting all values within these ranges and any ranges formed therein or thereby. The package materials of the present disclosure may exhibit a CD Stretch At Break of from about 4 percent and about 10 percent, from about 4.5 percent and about 9.5 percent, or from about 5 percent and about 9 percent, specifically reciting all values within these ranges and any ranges formed therein or thereby. The CD Stretch At Break is measured using the Strength Tensile Test Method described herein.

Regarding Caliper, the package materials of the present disclosure may exhibit a Caliper of at least 50 μm, at least 70 μm, or at least 90 μm, specifically reciting all values within these ranges and any ranges formed therein or thereby. The package materials of the present disclosure may exhibit a Caliper of between about 50 μm and about 110 μm, from about 55 μm and about 105 μm, or from about 60 μm and about 100 μm, specifically reciting all values within these ranges and any ranges formed therein or thereby. Caliper is measured using the Caliper Test Method described herein.

Regarding Tensile Energy Absorption (TEA), the package materials of the present disclosure may exhibit an MD TEA of at least 150 $J/m^2$, greater than 170 $J/m^2$, or at least 180 $J/m^2$, specifically reciting all values within these ranges and any ranges formed therein or thereby. The package materials of the present disclosure may have an MD TEA of between about 100 $J/m^2$ and about 250 $J/m^2$, between about 125 $J/m^2$ and about 225 $J/m^2$, or between about 150 $J/m^2$ and about 200 $J/m^2$, specifically reciting all values within these ranges and any ranges formed therein or thereby.

The package materials of the present disclosure may have a CD TEA of at least 150 $J/m^2$, at least 200 $J/m^2$, or at least 250 $J/m^2$, specifically reciting all values within these ranges and any ranges formed therein or thereby. The package materials of the present disclosure may have a CD TEA of between about 150 $J/m^2$ and about 275 $J/m^2$, from about 175 $J/m^2$ and about 260 $J/m^2$, or between about 200 $J/m^2$ and about 250 $J/m^2$, specifically reciting all values within these ranges and any ranges formed therein or thereby. TEA in the MD and CD are measured according the Strength Tensile Test Method described herein.

The Basis Weight of the package materials may affect the "feel" of the package to the consumer as well as the strength of the package. Too low of a Basis Weight and the package may feel too flimsy. Too high and the package may feel too inflexible. The package materials of the present disclosure have a Basis Weight of between about 50 gsm and about 120 gsm, between about 55 and about 115 gsm, or between about 60 gsm and about 110 gsm, specifically reciting all values within these ranges and any ranges formed therein or thereby. By such Basis Weights it is ensured that the package is flexible but retains its shape after opening and removal of one or more absorbent articles 1004. The Basis Weight, also referred to as "grammage", is determined according to the Basis Weight Test Method described herein.

It is worth noting that for high speed packaging processes, the lower Basis Weight of 50 gsm may provide some quality assurance outages. It is believed that high speed packaging processes may cause strain on the packaging materials that slower packaging processes may not. Therefore, where package materials are processed using a high speed manufacturing process, 60 gsm may be the lowest desirable package material Basis Weight. Where package materials are processed using a hand packing process or lower speed packaging processes, 50 gsm may be sufficient as the lowest package material Basis Weight.

The package materials of the present disclosure are different than carton board and cardboard. For example, carton board is not as flexible as the package materials of the present disclosure. Carton board is inherently stiffer than the package materials of the present disclosure and does not have the processability on high speed converting lines as does the package materials of the present disclosure. Additionally, carton board has a Basis Weight greater than 160 gsm, which is considerably higher than that of the package materials of the present disclosure.

Similarly, cardboard is also different than the package materials of the present disclosure. Cardboard has a much higher Basis Weight (greater than 200 gsm) than those of the package materials of the present disclosure. Additionally, cardboard is much less flexible than the package materials of the present disclosure. Cardboard materials are commonly fluted and comprise three plies of a paper material and, as such, are structurally different than the package materials of the present disclosure.

The package materials of the present disclosure have the advantage of being more flexible as compared to carton board and cardboard. Another advantage is that the package materials of the present disclosure take up less space than the more-bulky carton board and cardboard. A further advantage of the package materials of the present disclosure, attributable at least in part to the strength and resiliency properties discussed herein, is that the package materials allow the packaged absorbent articles to be compressed within the package. This allows for more products to fit within a smaller volume package which may increase manufacturing efficiency. One additional advantage is that a single layer (one ply) of the package materials of the present disclosure may form packages of the present disclosure. The inventors have found that, due at least in part to the flexibility, strength, and resiliency properties of the package materials, packages of the present disclosure may be formed from a single layer (one ply) of package materials of the present disclosure.

Despite having reduced flexibility compared to, for example, plastic packaging, and lower Basis Weight than cardboard and carton board, the inventors have surprisingly found the packaging materials of the present disclosure may withstand the rigors of a high speed manufacturing process—where a plurality of absorbent articles are placed within the package under compression—as well as the rigors of being shipped, provide protection from environmental insults during shipping and while on the store shelf, and provide protection for absorbent articles while in the consumers home.

Table 1 shows a variety of package materials which are able to be successfully utilized in packaging absorbent articles under high speed processing conditions, along with at least one package material which is not successful. The various properties discussed previously are also listed for each of the samples.

Sample 1: Packaging paper produced from pure, white kraft pulp and consisting entirely of virgin fibers, available from BillerudKorsnäs™ under the trade name Axello Tough White.

Sample 2: Packaging paper produced from pure, white kraft pulp and consisting entirely of virgin fibers, available from BillerudKorsnäs™ under the trade name Performance White SE.

Sample 3: Calendered specialty kraft paper consisting entirely of virgin fibers, available from Mondi™ under the trade name Advantage Smooth White Strong.

Sample 4: Packaging paper produced from kraft pulp, made of virgin fibers, and comprising a barrier coating of fluoropolymers, available from BillerudKorsnäs™ under the trade name Basix Glaze.

TABLE 1

| | Sample 1 | Sample 2 | Sample 3 | Sample 4 |
|---|---|---|---|---|
| Basis Weight (gsm) | 80 | 70 | 70 | 50 |
| MD Tensile Strength(kN/m) | 7.6 | 5.7 | 5.9 | 4.7 |
| CD Tensile Strength (kN/m) | 4.7 | 4.1 | 3.0 | 2.7 |
| Burst Strength (kPa) | 480 | — | 256 | 185 |
| MD Stretch At Break (%) | 4.5 | 6.0 | 2.5 | — |
| CD Stretch At Break (%) | 8.0 | 9.5 | 8.0 | — |
| Caliper (μm) | 92.0 | — | 89.0 | 67.0 |
| TEA MD (J/m$^2$) | 185 | 230 | — | — |
| TEA CD (J/m$^2$) | 240 | 200 | — | — |

The package material of Sample 4 is not able to be successfully utilized in the packaging of absorbent articles. During the placement of absorbent article in the package, the package material tore. Without wishing to be bound by theory, it is believed that Sample 4 failed due to a combination of low Basis Weight and a high speed packaging process. While Sample 4 failed under the conditions of the high speed process, it is believed that a sample having the properties of Sample 4 may be successful with the use of a gentler packaging process, such as hand packing.

Absorbent Article Configuration

The packages of the present disclosure may comprise one or more absorbent articles. The absorbent articles may be placed into the package in an unfolded or folded configuration. The articles may be folded laterally and/or longitudinally. The articles may comprise one fold line, and may be disposed within the package in a bi-fold configuration. The articles may comprise two fold lines, and may be disposed within the package in a tri-fold configuration.

Figure 4A:
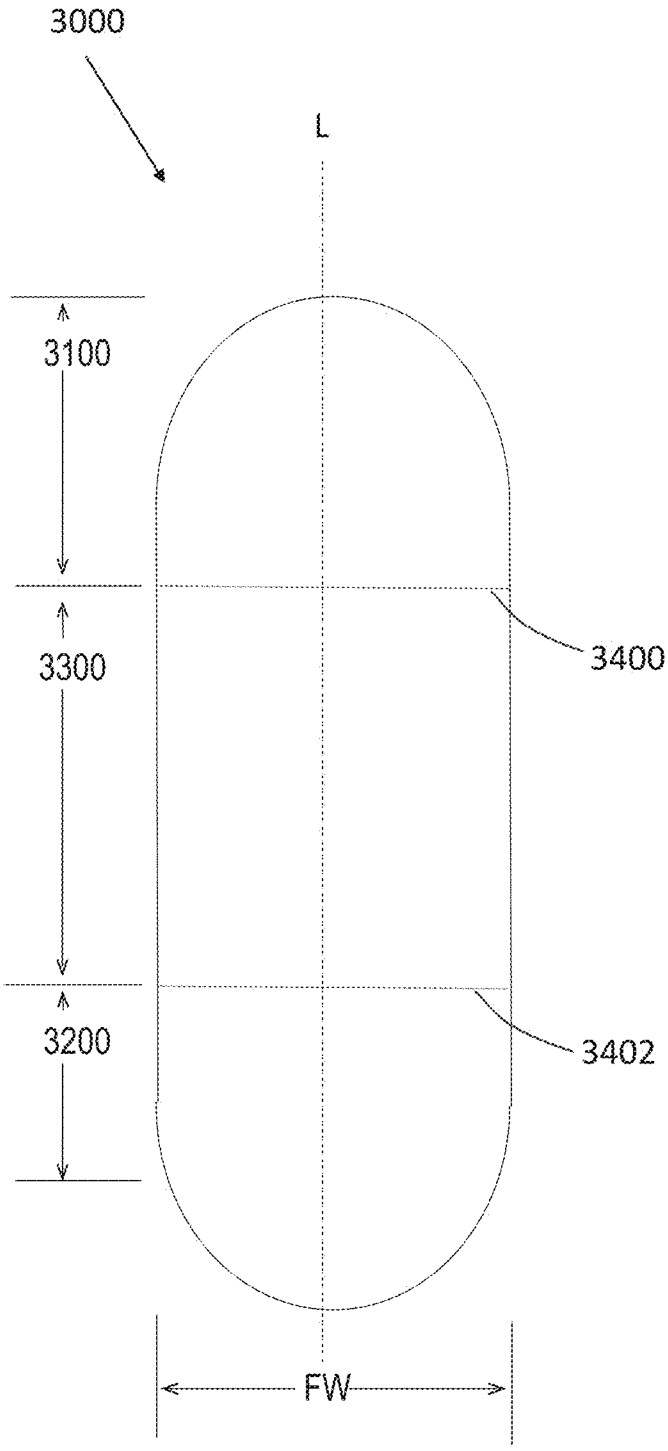
FIG. 4A is a plan view of an example of an absorbent article in the form of a feminine hygiene pad in an unfolded configuration.
Figure 4B:
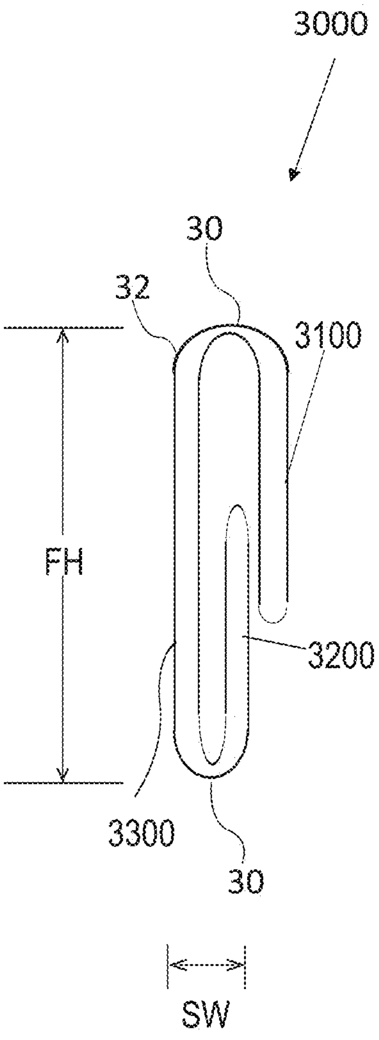
FIG. 4B is an edge side view of the feminine hygiene pad of FIG. 3A, shown folded about lateral fold lines in a tri-fold configuration.

FIG. 4A depicts an example of a feminine hygiene pad in an unfolded configuration. FIG. 4B depicts a side view of the feminine hygiene pad of FIG. 4A in a tri-fold configuration. The feminine hygiene pad depicted in FIGS. 4A and 4B comprises a first fold line 3400 disposed between a first end region of the pad 3100 and a central region of the pad 3300, and a second fold line 3402 disposed between a second end region of the pad 3200 and the central region 3300. Prior to placement within the package, the second end region 3200 may be folded over and longitudinally inward about the second fold line 3402 to overlap at least a portion of the central region 3300, as may be appreciated from a comparison of FIGS. 4A and 4B. The first end region 3100 may then be folded over and longitudinally inward about the first fold line 3400 to overlap at least a portion of the central region 3300 and a portion of the second end region 3200. In some examples a tri-fold configuration may have the article folded approximately in thirds, about the two longitudinally-spaced lateral fold lines.

Figure 5A:
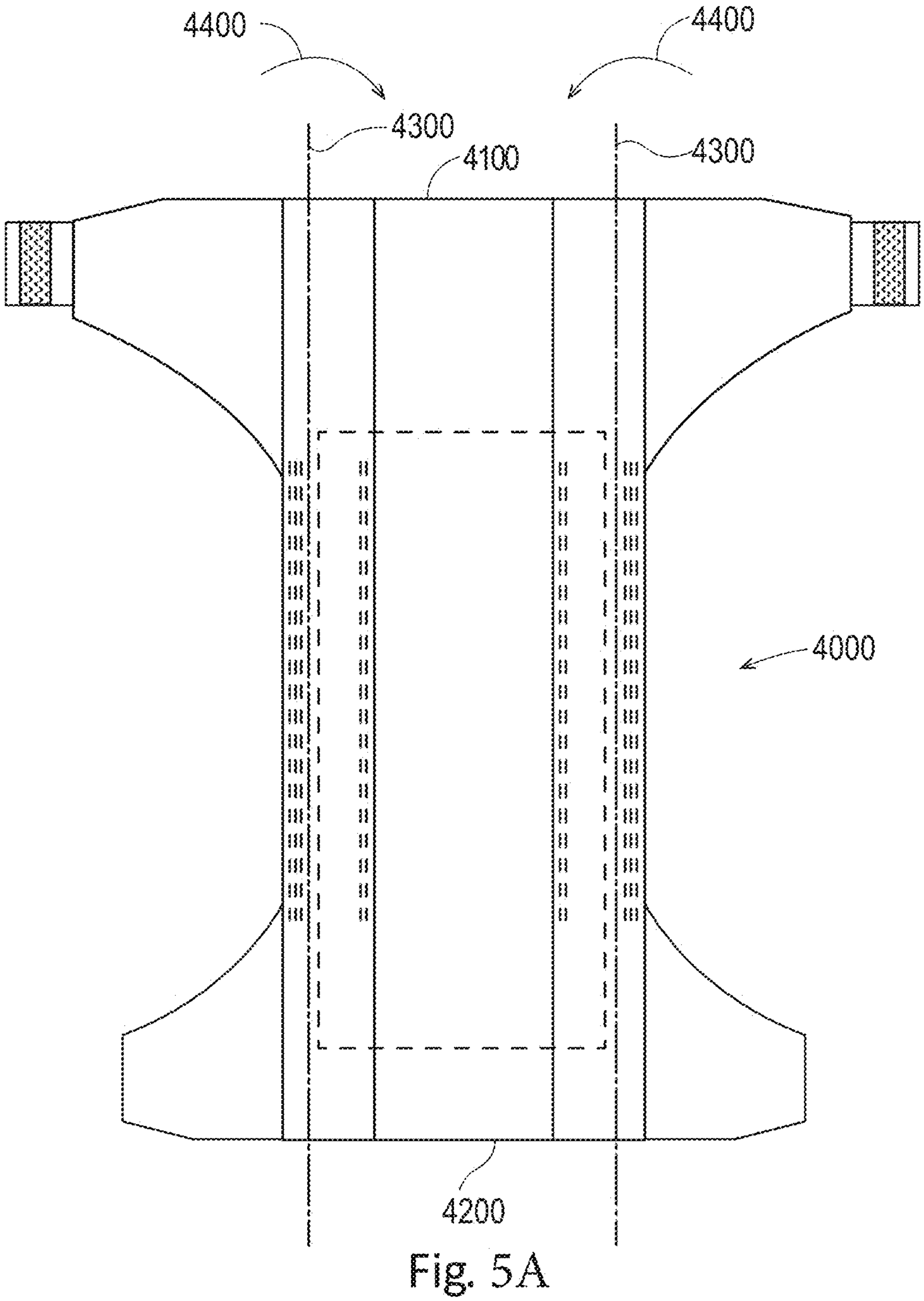
FIG. 5A is a plan view of an example of an absorbent article in the form of a disposable diaper, wearer-facing surfaces facing the viewer.
Figure 5B:
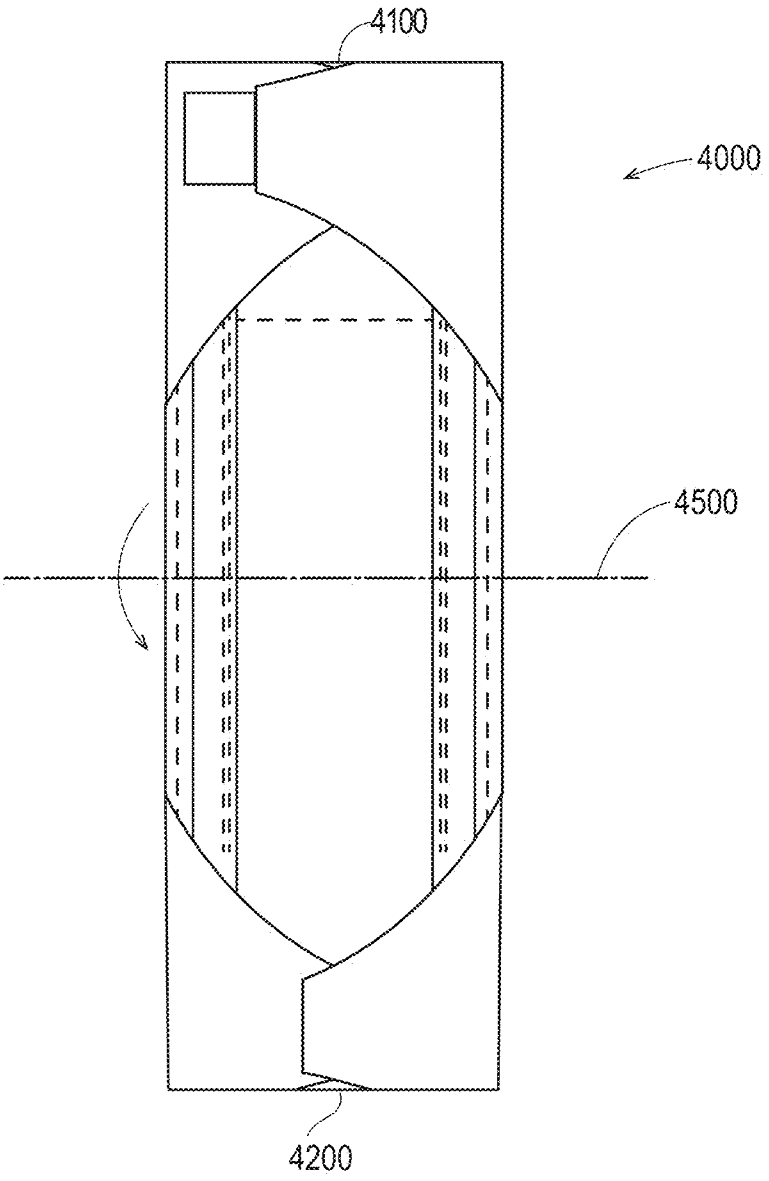
FIG. 5B is a plan view of the diaper of FIG. 5A, shown with side portions folded over and laterally inward about longitudinal side edge fold lines.
Figure 5C:
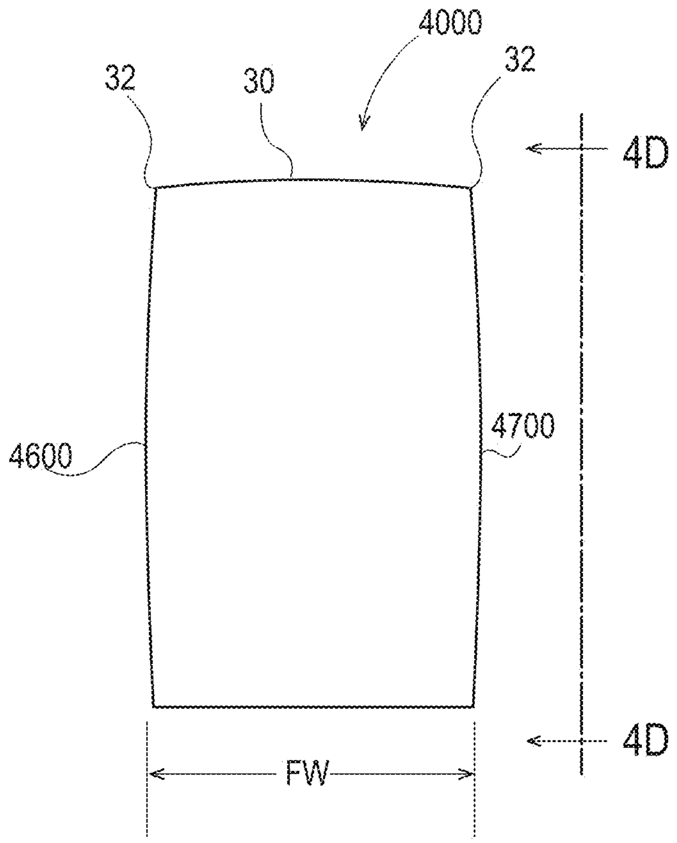
FIG. 5C is a plan view of the diaper of FIG. 5B, shown folded about a lateral fold line, wearer-facing surfaces in and outward-facing surfaces out.
Figure 5D:
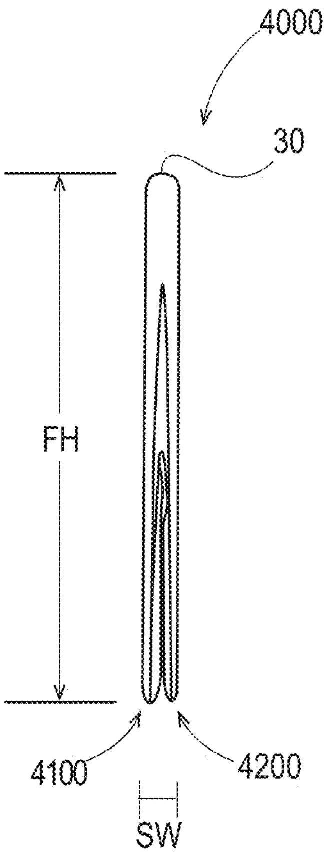
FIG. 5D is a side view of the folded diaper shown in FIG. 5C.

FIGS. 5A-5D depict an absorbent article in the form of a diaper 4000 with front and rear waist edges 4100, 4200, in successively open/unfolded and folded configurations. For packaging in bulk, each of a plurality of diapers such as that shown in FIG. 5A may, in a possible first step, have its longitudinal side portions be folded over and laterally inward about longitudinal side edge fold lines 4300, as may be appreciated from a comparison of FIGS. 5A and 5B. Next, the diaper may, in a second step, be folded longitudinally, about lateral fold line 4400 that passes through the crotch region of the diaper, as may be appreciated from a comparison of FIGS. 5B and 5C. For a bi-fold configuration such as depicted in FIGS. 5C and 5D, the article may be folded longitudinally once, and may in some examples be folded approximately in half about the lateral fold line 4400.

Regardless of whether the article is in a bi-fold or tri-fold configuration, the folded article, such as folded feminine hygiene pad 3000 and/or folded diaper 4000, may have a single fold nose 30 defining at least one end edge of the folded article, fold nose corners 32, and left and right longitudinal peripheral edges 4500, 4600. It will be appreciated that in a tri-fold example, a single fold nose may define each of both end edges of the folded article. In some examples, such as depicted in FIGS. 5C and 5D, fold nose 30 may be proximate the crotch region of the article (the middle region of the article adapted to be located between the wearer's legs during wear). The folded article will have a folded width FW measured as the distance between side edges, a folded height FH measured as the distance between fold nose 30 and the end edges (in the case of a bi-fold configuration) or between the two fold noses 30 (in the case of a tri-fold configuration), and a side width (SW). The folded width (FW) forms the flat, broad face of the folded absorbent article, while the side width (SW) forms the narrow folded side of the absorbent article.

Figure 6:
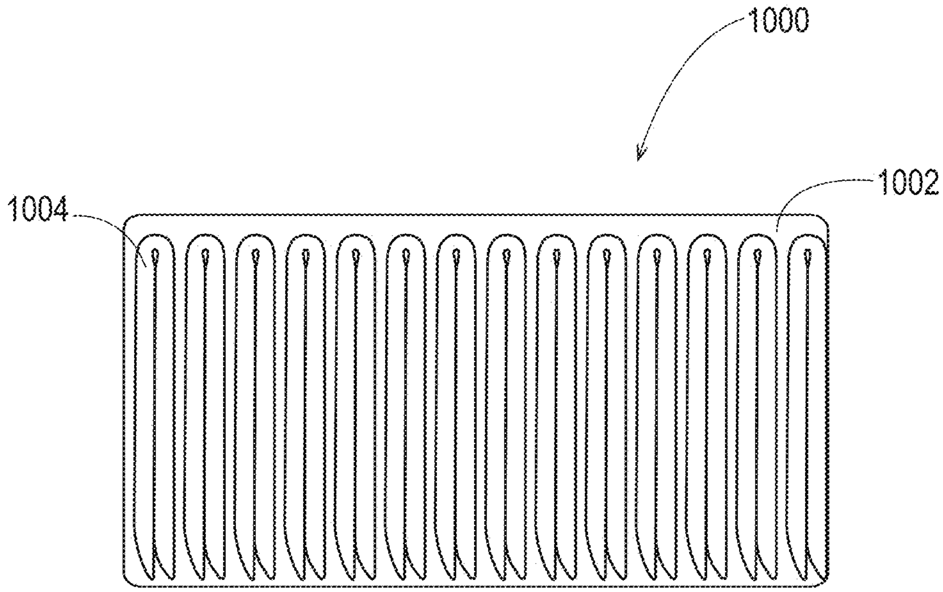
FIG. 6 is a side view of a stack of a plurality of absorbent articles disposed within a package of the present disclosure.

A plurality of folded articles such as depicted in FIGS. 5B and 5C and 5D may be placed in similar orientation within the interior compartment of a package of the present disclosure. FIGS. 6 and 7 depict a plurality of absorbent articles disposed within a package of the present disclosure. As shown in FIGS. 6 and 7, the package 1000 defines an interior compartment 1002 in which a plurality of absorbent articles 1004 are situated. The plurality of absorbent articles 1004 may be arranged in a single horizontal row, as shown in FIG. 6, or in one or more vertical stacks 1006, as shown in FIG. 7. Where the articles are arranged in more than one vertical stack, as shown in FIG. 7, all the articles may be oriented in the same direction. In another example, a first set of the plurality of folded articles may have their fold noses 30 oriented along one side of the stack, and a second set of the plurality of folded articles may be rotated 180 degrees to have their fold noses oriented along the opposite side of the stack. In some examples, the articles in the first set and the articles in the second set may appear in alternating sequence in the stack.

The folded absorbent articles may be disposed within the package of the present disclosure such that the folded width (FW) faces toward the first and second side panels. Such a configuration may be employed where the number of absorbent articles within the package is relatively large, e.g., greater than about ten individual absorbent articles, because the narrower sides (SW) of the articles will form front and back panels. Therefore, a relatively large number of absorbent articles may then be utilized to build up the front and back panels of the package. Such a configuration may be beneficial where the front and/or back panels form the consumer-facing panel.

The folded absorbent articles may be disposed within the package of the present disclosure such that the folded width (FW) faces toward the front and back panels. Such a configuration may be employed where the number of absorbent articles within the package is relatively low, e.g., less than about ten individual absorbent articles, because the wider sides (FW) of the articles will form front and back panels. Such a configuration may be beneficial where the front and/or back panels form the consumer-facing panel, and the number of absorbent articles disposed within the package is less than about ten.

The absorbent articles or articles may be packed under compression so as to reduce the size of the package, while still providing an adequate number of absorbent articles per package. By packaging the absorbent articles under compression, caregivers can easily handle and store the packages, while also providing distribution savings to manufacturers owing to the reduced size of the packages. Despite lacking the stretch properties of conventional plastic packaging material, the inventors have surprisingly found the package materials of the present disclosure are able to withstand the processing and distribution rigors, as mentioned herein, even with absorbent articles which are compressed within the package and without the use of an intermediate container. This is particularly unexpected as the materials of the present disclosure may not display the stretch properties of presently used conventional plastic films.

Packages of absorbent articles of the present disclosure may have an In-Bag Stack Height of less than about 150 mm, less than about 110 mm, less than about 105 mm, less than about 100 mm, less than about 95 mm, less than about 90 mm, less than about 85 mm, less than about 80 mm, less than about 78 mm, less than about 76 mm, less than about 74 mm, less than about 72 mm, or less than about 70 mm, specifically reciting all 0.1 mm increments within the specified ranges and all ranges formed therein or thereby, according to the In-Bag Stack Height Test described herein. Alternatively, packages of the absorbent articles of the present disclosure may have an In-Bag Stack Height of from about 70 mm to about 150 mm, from about 70 mm to about 110 mm, from about 70 mm to about 105 mm, from about 70 mm to about 100 mm, from about 70 mm to about 95 mm, from about 70 mm to about 90 mm, from about 70 mm to about 85 mm, from about 72 mm to about 80 mm, or from about 74 mm to about 78 mm, specifically reciting all 0.1 mm increments within the specified ranges and all ranges formed therein or thereby, according to the In-Back Stack Height Test Method described herein.

Other Products within the Packages of the Present Disclosure

Many suitable products may be placed within the packages and package materials of the present disclosure, such as consumer products. As an example, packages of the present disclosure may comprise or have contained therein, one or more moisture labile products, humidity labile products, moisture sensitive products, or water vapor sensitive products including unit dose products, unit dose pouches, articles meant for single use, pouches, pouches with fibrous wall materials, pouches with soluble film wall materials, pouches comprising a single layer or ply, and combinations thereof. These unit dose or pouch form products are delivery vehicles comprising active agents or additives designed and intended to provide a benefit to something, such as providing a benefit to an environment external to the unit dose or pouch. The active agents may comprise an active agent containing particle, powder, granule, encapsulate, and/or pill comprising one or more active agents. Alternatively, the active agents may comprise active an active agent embodied within or located in the cross section of one or more fibers making up the fibrous wall material of the unit dose or pouch.

One embodiment may comprise a unit dose article or pouch where active agents are contained on the internal volume of the unit dose article or pouch. Another embodiment may comprise a unit dose or pouch comprising a single layer or ply where the active agent is contained within the single layer or ply, coated or embedded on the surface of the layer or ply, or a combination of these two configurations. Yet another embodiment may comprise a unit dose or pouch comprising a plurality of plies wherein the active agent is contained within the single layer or ply, coated or embedded on the surface of the layer or ply, between plies or a combination of these configurations.

Active agents may be any suitable additive that produces an intended effect under intended use conditions of the unit dose article or pouch. The active agents may comprise an active agent containing particle or a plurality of particles. For example, the active agent or active agent contained in a particle or particles may be selected from the group consisting of: personal cleansing and/or conditioning agents, such as hair care agents such as shampoo agents and/or hair colorant agents, hair conditioning agents, skin care agents, sunscreen agents, and skin conditioning agents; laundry care and/or conditioning agents such as fabric care agents, fabric conditioning agents, fabric softening agents, fabric anti-wrinkling agents, fabric care anti-static agents, fabric care stain removal agents, soil release agents, dispersing agents, suds suppressing agents, suds boosting agents, anti-foam agents, and fabric refreshing agents; liquid and/or powder dishwashing agents (for hand dishwashing and/or automatic dishwashing machine applications), hard surface care agents, and/or conditioning agents and/or polishing agents; other cleaning and/or conditioning agents such as antimicrobial agents, antibacterial agents, antifungal agents, fabric hueing agents, perfume, bleaching agents (such as oxygen bleaching agents, hydrogen peroxide, percarbonate bleaching agents, perborate bleaching agents, chlorine bleaching agents), bleach activating agents, chelating agents, builders, lotions, brightening agents, air care agents, carpet care agents, dye transfer-inhibiting agents, clay soil removing agents, anti-redeposition agents, polymeric soil release agents, polymeric dispersing agents, alkoxylated polyamine polymers, alkoxylated polycarboxylate polymers, amphilic graft copolymers, dissolution aids, buffering systems, water-softening agents, water-hardening agents, pH adjusting agents, enzymes, flocculating agents, effervescent agents, preservatives, cosmetic agents, make-up removal agents, lathering agents, deposition aid agents, coacervate-forming agents, clays, thickening agents, latexes, silicas, drying agents, odor control agents, antiperspirant agents, cooling agents, warming agents, absorbent gel agents, anti-inflammatory agents, dyes, pigments, acids, and bases; liquid treatment active agents; agricultural active agents; industrial active agents; ingestible active agents such as medicinal agents, teeth whitening agents, tooth care agents, mouthwash agents, periodontal gum care agents, edible agents, dietary agents, vitamins, minerals; water-treatment agents such as water clarifying and/or water disinfecting agents, surfactants, anionic surfactants, cationic surfactants, nonionic surfactants, zwitterionic surfactants, amphoteric surfactants, one or more silicones, one or more alkali metal or alkaline-earth metal carbonates, alkali metal carbonates (e.g. sodium carbonate, potassium carbonate, etc.), alkali metal hydrogen carbonates (e.g., sodium hydrogen carbonate, potassium hydrogen carbonate, etc.), ammonium carbonate, organic acids (e.g., hydroxy-carboxylic acids [citric acid, tartaric acid, malic acid, lactic acid, gluconic acid, etc.], saturated aliphatic carboxylic acids [acetic acid, succinic acid, etc.], unsaturated aliphatic carboxylic acids [e.g., fumaric acid, etc.]. and mixtures thereof.

Example unit dose articles or pouches of the present disclosure include those described in U.S. Pat. Appl. Pub. No. 2013/0172226, U.S. Pat. Appl. Pub. No. 2015/0071572, U.S. Pat. Appl. Pub. No. 2018/0216285, U.S. Pat. Appl. Pub. No. 2018/0216286, U.S. Pat. Appl. Pub. No. 2018/0216287, U.S. Pat. Appl. Pub. No. 2018/0216288, and PCT publications WO 2022/117853, WO 2022/117854, WO 2022/117855, WO 2022/117856, WO 2022/117858, WO 2022/117859, WO 2022/117860, WO 2022/117861.

Contemplated Examples

A. A package (1) comprising one or more absorbent articles (1004) comprising:
  a package material comprises natural fibers;
  the package material forms a front panel (14), a back panel (15) opposite the front panel (14), a first side panel (12), a second side panel (13) opposite the first side panel (12), a top panel (11), and a bottom panel (10) opposite the top panel (11), wherein the panels define an interior compartment of the package (1), and wherein one or more absorbent articles are disposed in the interior compartment;
  the package (1) comprises a primary seal (2) and the package (1) is sealed by the primary seal (2) such that the one or more absorbent articles (1004) are enclosed within the interior compartment;
  wherein the package (1) comprises a secondary closing element (3) and the secondary closing element (3) is reclosable.

B. The package of example A, wherein the package material has a Basis Weight between about 50 gsm and about 120 gsm, preferably between about 55 gsm and about 115 gsm, more preferably between about 60 gsm and about 110 gsm, according to the Basis Weight Test Method disclosed herein.

C. The package of any one of examples A to B, wherein the primary seal (2) exhibits a Normalized Average Peel Force at first peel of at least 50 mN/mm, preferably at least 60 mN/mm, more preferably at least 80 mN/mm, even more preferably at least 90 mN/mm or even at least 100 mN/mm according to the Seal Strength Test Method disclosed herein.

D. The package of any one of examples A to C, wherein the secondary closing element (3) exhibits a Normalized Average Peel Force at first peel of at most 500 mN/mm, preferably at most 400 mN/mm, more preferably at most 350 mN/mm, even more preferably at most 300 mN/mm or even at most 250 mN/mm according to the Seal Strength Test Method disclosed herein.

E. The package of any one of examples A to D, wherein the secondary closing element (3) exhibits a Normalized Average Peel Force at fifth peel of from 60% to 100%, preferably 70% to 99%, more preferably from 80% to 95% of the Normalized Average Peel Force at first peel according to the Seal Strength Test Method disclosed herein.

F. The package of any one of examples A to E, wherein the secondary closing element (3) comprises a reclosing means selected from the group consisting of an adhesive, a cohesive, and a mechanical fastener.

G. The package of example F, wherein the secondary closing element (3) comprises a double-sided tape.

H. The package of any one of examples A to G, wherein the secondary closing element (3) is activated to become closable upon or after first opening of the primary seal (2).

I. The package of any one of examples A to H, wherein the package (1) is sealed by the primary seal (2) such that the secondary closing element (3) is enclosed within the package (1).

J. The package of any one of examples A to I, wherein the secondary closing element (3) is located closer to the one or more absorbent articles (1004) than the primary seal (2).

K. The package of any one of examples A to J, wherein the secondary closing element (3) is located in between two gussets (11*c*) of the top panel (11).

L. The package of example K, wherein the secondary closing element (3) is configured to close at least 60%, preferably at least 70%, more preferably at least 80%, even more preferably at least 90% or even at least 95% of the distance between the two gussets (11*b*) of the top panel (11).

M. The package of example K or example L, wherein the secondary closing element (3) has a width of at least 60%, preferably at least 70%, more preferably at least 80%, even more preferably at least 90% or even at least 95% of the distance between the two gussets in the top panel (11).

N. The package of any one of examples A to M, wherein the secondary closing element (3) has a maximum width from 0.5 cm to 30 cm, preferably from 1 cm to 25 cm, more preferably from 2 cm to 20 cm, even more preferably from 3 cm to 15 cm or even from 5 cm to 10 cm.

O. The package of any one of examples A to N, wherein the secondary closing element (3) has a maximum height from 0.2 cm to 6 cm, preferably from 0.3 cm to 5 cm, more preferably from 0.5 cm to 4 cm, even more preferably from 0.7 cm to 3 cm or even from 1 cm to 2 cm.

P. The package of any one of examples A to O, wherein the secondary closing element (3) has a total area from 0.1 $cm^2$ to 100 $cm^2$, preferably from 1 $cm^2$ to 80 $cm^2$, more preferably from 2 $cm^2$ to 60 $cm^2$, even more preferably from 5 $cm^2$ to 50 $cm^2$ or even from 10 $cm^2$ to 30 $cm^2$.

Q. The package of any one of examples A to P, wherein the package (1) comprises a weakened region disposed in the package material configured to form an opening.

R. The package of example Q, wherein the weakened region is located between the primary seal (2) and the secondary closing element (3).

S. The package of any one of examples A to R, wherein the package material is a paper-based material.

T. The package of any one of examples A to S, wherein the package material comprises a moisture barrier layer.

U. The package of any one of examples A to T, wherein the package material comprises at least 50 percent by weight natural fibers, preferably at least 70 percent by weight natural fibers, more preferably at least 90 percent by weight natural fibers.

V. The package of any one of examples A to U, wherein the packaging material has a recyclable percentage of between about 60 percent and about 99.9 percent determined via the PTS-RH:021/97 (Draft October 2019) under category II Test Method disclosed herein.

W. The package of any one of examples A to V, wherein the primary seal (2) exhibits a Normalized Average Peel Force of at least 50 mN/mm, preferably at least 60 mN/mm, more preferably at least 80 mN/mm, even more preferably at least 80 mN/mm or even at least 100 mN/mm according to the Seal Strength Test Method disclosed herein.

X. The package of any one of examples A to W, wherein the primary seal (2) exhibits a Normalized Average Peel Force of between 50 mN/mm and 600 mN/mm, preferably between 60 mN/mm and 500 mN/mm, more preferably between 80 mN/mm and 400 mN/mm, even more preferably between 90 mN/mm and 300 mN/mm or even between 100 mN/mm and 250 mN/mm according to the Seal Strength Test Method disclosed herein.

Y. The package of any one of examples A to X, wherein the secondary closing element (3) exhibits a Normalized Average Peel Force at first peel of at most 500 mN/mm, preferably at most 400 mN/mm, more preferably at most 350 mN/mm, even more preferably at most 300 mN/mm or even at most 250 mN/mm according to the Seal Strength Test Method disclosed herein.

Z. The package of any one of examples A to Y, wherein the secondary closing element (3) exhibits a Normalized Average Peel Force at first peel of between 50 mN/mm and 500 mN/mm, preferably between 60 mN/mm and 400 mN/mm, more preferably between 80 mN/mm and 350 mN/mm, even more preferably between 90 mN/mm and 300 mN/mm or even between 100 mN/mm and 250 mN/mm according to the Seal Strength Test Method disclosed herein.

AA. The package of any one of examples A to Z, wherein the secondary closing element (3) exhibits a Normalized Average Peel Force at fifth peel of from 60% to 100%, preferably 70% to 99%, more preferably from 80% to 95% of the Normalized Average Peel Force at first peel according to the Seal Strength Test Method disclosed herein.

BB. The package of any one of examples A to AA, wherein the secondary closing element (3) exhibits a Normalized Average Peel Force at fifth peel between 30 mN/mm and 600 mN/mm, preferably between 40 mN/mm and 500 mN/mm, more preferably between 50 mN/mm and 400 mN/mm, even more preferably between 60 mN/mm and 350 mN/mm or even between 80 mN/mm and 300 mN/mm according to the Seal Strength Test Method disclosed herein.

CC. The package of any one of examples A to BB, wherein the secondary closing element (3) exhibits a Normalized Average Peel Force at first peel of from 60% to 500%, preferably 70% to 400%, more preferably from 80% to 300%, or even from 100% to 250% of the Normalized Average Peel Force of the primary seal (2) according to the Seal Strength Test Method disclosed herein.

DD. The package of any one of examples A to CC, wherein the primary seal (2) exhibits a Normalized Peak Load at first peel of at least 100 mN/mm, preferably at least 150 mN/mm, more preferably at least 200 mN/mm, even more preferably at least 250 mN/mm or even at least 300 mN/mm according to the Seal Strength Test Method disclosed herein.

EE. The package of any one of the any one of examples A to DD, wherein the primary seal (2) exhibits a Normalized Peak Load of between 100 mN/mm and 1000 mN/mm, preferably between 150 mN/mm and 800 mN/mm, more preferably between 200 mN/mm and 600 mN/mm, even more preferably between 250 mN/mm and 500 mN/mm or even between 300 mN/mm and 400 mN/mm according to the Seal Strength Test Method disclosed herein.

FF The package of any one of examples A to EE, wherein the secondary closing element (3) exhibits a Normalized Peak Load at first peel of at most 900 mN/mm, preferably at most 800 mN/mm, more preferably at most 700 mN/mm, even more preferably at most 600 mN/mm or even at most 500 mN/mm according to the Seal Strength Test Method disclosed herein.

GG. The package of any one of examples A to FF, wherein the secondary closing element (3) exhibits a Normalized Peak Load at first peel of between 80 mN/mm and 900 mN/mm, preferably between 100 mN/mm and 800 mN/mm, more preferably between 150 mN/mm and 700 mN/mm, even more preferably between 200 mN/mm and 600 mN/mm or even between 250 mN/mm and 500 mN/mm according to the Seal Strength Test Method disclosed herein.

HH. The package of any one of examples A to GG, wherein the secondary closing element (3) exhibits a Normalized Peak Load at fifth peel of 60% to 100%, preferably 70% to 99%, more preferably from 80% to 95% of the Normalized Average Peak Load at first peel according to the Seal Strength Test Method disclosed herein.

II. The package of any one of examples A to HH, wherein the secondary closing element (3) exhibits a Normalized Peak Load at fifth peel between 50 mN/mm and 1000 mN/mm, preferably between 60 mN/mm and 900 mN/mm, more preferably between 80 mN/mm and 800 mN/mm, even more preferably between 100 mN/mm and 700 mN/mm or even between 150 mN/mm and 600 mN/mm according to the Seal Strength Test Method disclosed herein.

JJ. The package of any one of examples A to II, wherein the secondary closing element (3) exhibits a Normalized Peak Load at fifth peel between 30 mN/mm and 600 mN/mm, preferably between 40 mN/mm and 500 mN/mm, more preferably between 50 mN/mm and 400 mN/mm, even more preferably between 60 mN/mm and 350 mN/mm or even between 80 mN/mm and 300 mN/mm according to the Seal Strength Test Method disclosed herein.

KK. The package of any one of examples A to JJ, wherein the secondary closing element (3) exhibits a Normalized Peak Load at first peel of from 60% to 400%, preferably 70% to 300%, more preferably from 80% to 200% of the Normalized Average Peak Load of the primary seal (2) according to the Seal Strength Test Method disclosed herein.

LL. The package of any one of examples A to KK, wherein the primary seal (2) exhibits a Normalized Peel Energy of at least 500 mN/mm, preferably at least 700 mN/mm, more preferably at least 800 mN/mm, even more preferably at least 900 mN/mm or even at least 1000 mN/mm according to the Seal Strength Test Method disclosed herein.

MM. The package of any one of examples A to LL, wherein the primary seal (2) exhibits a Normalized Peel Energy of between 500 mN/mm and 2000 mN/mm, preferably between 700 mN/mm and 1800 mN/mm, more preferably between 800 mN/mm and 1600 mN/mm, even more preferably between 900 mN/mm and 1500 mN/mm or even between 1000 mN/mm and 1300 mN/mm according to the Seal Strength Test Method disclosed herein.

NN. The package of any one of examples A to MM, wherein the secondary closing element (3) exhibits a Normalized Peel Energy at first peel of at most 1500 mN/mm, preferably at most 1200 mN/mm, more preferably at most 1000 mN/mm, even more preferably at most 900 mN/mm or even at most 800 mN/mm according to the Seal Strength Test Method disclosed herein.

OO. The package of any one of examples A to NN, wherein the secondary closing element (3) exhibits a Normalized Peel Energy at first peel of between 250 mN/mm and 1500 mN/mm, preferably between 300 mN/mm and 1200 mN/mm, more preferably between 400 mN/mm and 1000 mN/mm, even more preferably between 450 mN/mm and 900 mN/mm or even between 500 mN/mm and 800 mN/mm according to the Seal Strength Test Method disclosed herein.

PP. The package of any one of examples A to OO, wherein the secondary closing element (3) exhibits a Normalized Peel Energy at fifth peel of from 60% to 100%, preferably 70% to 99%, more preferably from 80% to 95% of the Normalized Peel Energy at first peel according to the Seal Strength Test Method disclosed herein.

QQ. The package of any one of examples A to PP, wherein the secondary closing element (3) exhibits a Normalized Peel Energy at fifth peel between 150 mN/mm and 1800 mN/mm, preferably between 200 mN/mm and 1500 mN/mm, more preferably between 250 mN/mm and 1200 mN/mm, even more preferably between 300 mN/mm and 1000 mN/mm or even between 400 mN/mm and 900 mN/mm according to the Seal Strength Test Method disclosed herein.

RR. The package of any one of examples A to QQ, wherein the secondary closing element (3) exhibits a Normalized Peel Energy at first peel of from 50% to 200%, preferably 60% to 150%, more preferably from 70% to 120% or even from 80% to 100% of the Normalized Peel Energy of the primary seal (2) according to the Seal Strength Test Method disclosed herein.

SS. The package of any one of examples A to RR, wherein the primary seal (2) exhibits one or more property selected from the group consisting of:

a) a Normalized Average Peel Force of between 50 mN/mm and 600 mN/mm, preferably between 60 mN/mm and 500 mN/mm, more preferably between 80 mN/mm and 400 mN/mm, even more preferably between 90 mN/mm and 300 mN/mm or even between 100 mN/mm and 250 mN/mm;

b) a Normalized Peak Load of between 100 mN/mm and 1000 mN/mm, preferably between 150 mN/mm and 800 mN/mm, more preferably between 200 mN/mm and 600 mN/mm, even more preferably between 250 mN/mm and 500 mN/mm or even between 300 mN/mm and 400 mN/mm according to the Seal Strength Test Method disclosed herein; and c) a Normalized Peel Energy of between 500 mN/mm and 2000 mN/mm, preferably between 700 mN/mm and 1800 mN/mm, more preferably between 800 mN/mm and 1600 mN/mm, even more preferably between 900 mN/mm and 1500 mN/mm or even between 1000 mN/mm and 1300 mN/mm according to the Seal Strength Test Method disclosed herein.

TT. The package of any one of examples A to SS, wherein the secondary closing element (3) exhibits one or more property selected from the group consisting of:

a) a Normalized Average Peel Force at first peel of between 50 mN/mm and 500 mN/mm, preferably between 60 mN/mm and 400 mN/mm, more preferably between 80 mN/mm and 350 mN/mm, even more preferably between 90 mN/mm and 300 mN/mm or even between 100 mN/mm and 250 mN/mm according to the Seal Strength Test Method disclosed herein;

b) a Normalized Average Peel Force at fifth peel between 30 mN/mm and 600 mN/mm, preferably between 40 mN/mm and 500 mN/mm, more preferably between 50 mN/mm and 400 mN/mm, even more preferably between 60 mN/mm and 350 mN/mm or even between 80 mN/mm and 300 mN/mm according to the Seal Strength Test Method disclosed herein;

c) a Normalized Peak Load at first peel of between 80 mN/mm and 900 mN/mm, preferably between 100 mN/mm and 800 mN/mm, more preferably between 150 mN/mm and 700 mN/mm, even more preferably between 200 mN/mm and 600 mN/mm or even between 250 mN/mm and 500 mN/mm according to the Seal Strength Test Method disclosed herein;

d) a Normalized Peak Load at fifth peel between 30 mN/mm and 600 mN/mm, preferably between 40 mN/mm and 500 mN/mm, more preferably between 50 mN/mm and 400 mN/mm, even more preferably between 60 mN/mm and 350 mN/mm or even between 80 mN/mm and 300 mN/mm according to the Seal Strength Test Method disclosed herein e) a Normalized Peel Energy at first peel of between 500 mN/mm and 2000 mN/mm, preferably between 700 mN/mm and 1800 mN/mm, more preferably between 800 mN/mm and 1600 mN/mm, even more preferably between 900 mN/mm and 1500 mN/mm or even between 1000 mN/mm and 1300 mN/mm according to the Seal Strength Test Method disclosed herein; and f) a Normalized Peel Energy at fifth peel between 150 mN/mm and 1800 mN/mm, preferably between 200 mN/mm and 1500 mN/mm, more preferably between 250 mN/mm and 1200 mN/mm, even more preferably between 300 mN/mm and 1000 mN/mm or even between 400 mN/mm and 900 mN/mm according to the Seal Strength Test Method disclosed herein.

UU. The package of any one of examples A to TT, wherein the inner surface of the package (1) opposing the secondary closing element (3) comprises a receptive area.

VV. A bag (4) for forming a package (1) according to any of examples A to UU, wherein the bag comprises a first surface (10), a second surface (12), a third surface (13), a fourth surface (14) and a fifth surface (15), an open end (48) opposing the first surface (10); wherein one surface selected from the group consisting of second surface (12), the third surface (13), the fourth surface (14) and the fifth surface (15) comprises the secondary closing element (3).

WW. The bag of example VV, wherein two or more surfaces selected from the group consisting of second surface (12), the third surface (13), the fourth surface (14) and the fifth surface (15) comprises adhesive to form the primary seal (2).

XX. The bag of example VV or WW, wherein either only one surface selected from the group consisting of second surface (12), the third surface (13), the fourth surface (14) and the fifth surface (15) comprises the secondary closing element or only two opposing surfaces selected from the group consisting of second surface (12), the third surface (13), the fourth surface (14) and the fifth surface (15) comprise the secondary closing element (3).

YY. The bag of any one of examples VV to XX, wherein the surface opposing the surface comprising the secondary closing element (3) comprises a receptive area.

AAA. A bag (4) for forming a package (1) comprising one or more absorbent articles (1004), wherein the bag comprises a package material and a first surface (10), a second surface (12), a third surface (13), a fourth surface (14) and a fifth surface (15), an open end (48) opposing the first surface (10); wherein one surface selected from the group consisting of second surface (12), the third surface (13), the fourth surface (14) and the fifth surface (15) comprises a secondary closing element (3), wherein the secondary closing element (3) is reclosable, and two or more surfaces selected from the group consisting of the second surface (12), the third surface (13), the fourth surface (14) and the fifth surface (15) comprise a primary sealing area to form a primary seal (2).

BBB. The bag of example AAA, wherein the primary sealing area is located closer to the open end (48) then the secondary closing element (3).

CCC. The bag of any one of examples AAA or BBB, wherein the primary sealing area comprises adhesive to form the primary seal (2).

DDD. The bag of any one of examples AAA to CCC, wherein the bag (4) comprises a package material and the package material has a Basis Weight between about 50 gsm and about 120 gsm, preferably between about 55 gsm and about 115 gsm, more preferably between about 60 gsm and about 110 gsm, according to the Basis Weight Test Method disclosed herein.

EEE. The bag of any one of examples AAA to DDD, wherein the secondary closing element (3) comprises a reclosing means selected from the group consisting of an adhesive, a cohesive, and a mechanical fastener.

FFF. The bag of example EEE, wherein the secondary closing element (3) comprises a double-sided tape.

GGG. The bag of examples AAA to FFF, wherein the secondary closing element (3) has a maximum width from 0.5 cm to 30 cm, preferably from 1 cm to 25 cm, more preferably from 2 cm to 20 cm, even more preferably from 3 cm to 15 cm or even from 5 cm to 10 cm.

HHH. The bag of any one of examples AAA to GGG, wherein the secondary closing element (3) has a maximum height from 0.2 cm to 6 cm, preferably from 0.3 cm to 5 cm, more preferably from 0.5 cm to 4 cm, even more preferably from 0.7 cm to 3 cm or even from 1 cm to 2 cm.

III. The bag of any one of examples AAA to HHH, wherein the secondary closing element (3) has a total area from 0.1 $cm^2$ to 100 $cm^2$, preferably from 1 $cm^2$ to 80 $cm^2$, more preferably from 2 $cm^2$ to 60 $cm^2$, even more preferably from 5 $cm^2$ to 50 $cm^2$ or even from 10 $cm^2$ to 30 $cm^2$.

JJJ. The bag of examples AAA to III, wherein the bag (4) comprises a weakened region disposed in the package material configured to form an opening.

KKK. The bag of example JJJ, wherein the weakened region is located between the primary sealing area and the secondary closing element (3).

LLL. The bag of examples AAA to KKK, wherein the package material is a paper-based material.

MMM. The bag of examples AAA to LLL, wherein the package material comprises a moisture barrier layer.

NNN. The bag of any one of examples AAA to MMM, wherein the package material comprises at least 50 percent by weight natural fibers, preferably at least 70 percent by weight natural fibers, more preferably at least 90 percent by weight natural fibers.

OOO. The bag of any one of examples AAA to NNN, wherein the packaging material has a recyclable percentage of between about 60 percent and about 99.9 percent determined via the PTS-RH:021/97 (Draft October 2019) under category II Test Method disclosed herein.

PPP. The bag of any one of examples AAA to OOO, wherein the surface opposing the surface comprising the secondary closing element (3) comprises a receptive area.

Test Methods

Seal Strength Test Method

The seal strength of an absorbent article package is determined by measuring the force required to separate one side of the seal (e.g. front panel of the package) from the opposing side of the seal (e.g. back panel of the package) by executing a typical peel test using a universal constant rate of extension test frame. Seal strength is measured on a test specimen obtained from the primary seal region of the package as it is initially opened (i.e. “first peel”). Additionally, seal strength is measured on a test specimen obtained from the secondary closing element region on the package after it is initially sealed (“activated”) and then opened (i.e. “first peel”), and then again after it is re-sealed and re-opened for a total of five subsequent opening incidents to measure the strength of the re-closable feature. All measurements are performed in a laboratory maintained at 23 °C±2 °C and 50%±2% relative humidity and test specimens are conditioned in this environment for at least 2 hours prior to testing.

A suitable universal constant rate of extension test frame is the MTS Alliance interfaced to a computer running TestSuite control software (available from MTS Systems Corp, Eden Prairie, MN), or equivalent. The universal test frame is equipped with a load cell for which forces measured are within 1% to 99% of the limit of the cell. The fixtures used to grip the test specimen are lightweight (<80 grams), vise action clamps with knife or serrated edge grip faces that are at least 40 mm wide. The fixtures are installed on the universal test frame and mounted such that they are horizontally and vertically aligned with one another.

A small, padded weight is used to ensure adequate and reproducible contact during the initial activation and subsequent re-sealing steps required for the multiple peeling incidents of the secondary closing element. The padded weight consists of a ⅛ inch thick polyurethane foam base (open cell, medium density of 20 lbs/cu ft, 18 psi to compress to 25%, available from McMaster-Carr as part #86375K133, or equivalent) plus additional mass required to impart a pressure of about 1.5 psi. The base of the padded weight that will contact the test specimen will have dimensions that closely match the dimensions of the seal within the test specimen. Sufficient additional mass is then added on top of the prepared base to reach a pressure of 1.5 psi. The additional mass can be in any convenient form, such as a steel cylinder with washers or shot used to reach the exact mass requirement. For example, a secondary closing element that has a seal with a width of 25 mm and a length of 20 mm, the ⅛ inch thick polyurethane foam will be cut to form a base that is 25 mm by 20 mm, and the total mass of the prepared base plus additional mass will equal 527.3 g to impart a pressure of 1.5 psi.

Prepare a test specimen from the primary seal region of an absorbent article package as follows. So as not to disturb the location where the primary seal is located at or near the top panel 11 of the package, the package is opened at the bottom panel 10 such that all other sides (front, back, top, first side, second side) remain intact, and the absorbent articles are removed and discarded. The empty package is then flattened in a front to back manner such that any creases imparted to form any gussets are maintained. Now locate the primary seal at or near the top panel. The flattened package is then cut, from the uppermost edge of the top panel to the lowermost edge of the bottom panel, to form a 30 mm wide strip whose width is centered over the lateral midpoint of the package. The cut strip will contain the front panel, the back panel, and the primary seal. With the aid of a lightbox, if needed, the width (lateral direction) and height (longitudinal direction) of the seal within the prepared strip is measured using a steel ruler (NIST certified), and recorded as width and height, respectively, to the nearest 0.1 mm. Calculate the seal area by multiplying the width by the height and record as area to the nearest 0.1 $mm^2$. In like fashion, a total of five replicate test specimen strips are prepared from the primary seal of five separate absorbent article packages.

Prepare a test specimen from the secondary closing element region of an absorbent article package as follows. So as not to initially disturb the location where the primary seal is located at or near the top panel 11 of the package, the package is opened at the bottom panel 10 such that all other sides (front, back, top, first side, second side) remain intact, and the absorbent articles are removed and discarded. The empty package is then flattened in a front to back manner such that any creases imparted to form any gussets are maintained. Now locate the primary seal at or near the top panel, and then locate the position of the secondary closing element. If needed, one package can be sacrificed to identify the location of the secondary closing element. The flattened package is then cut, from the uppermost edge of the top panel to the lowermost edge of the bottom panel, to form a 30 mm wide strip whose width is centered over the lateral midpoint of the secondary closing element on the package. The cut strip will contain the front panel, the back panel, the primary seal, and the secondary closing element. With the aid of a lightbox, if needed, the width (lateral direction) and height (longitudinal direction) of the secondary closing element within the prepared strip is measured using a steel ruler (NIST certified), and recorded as width and height, respectively, to the nearest 0.1 mm. Calculate the seal area by multiplying the width by the height and record as area to the nearest 0.1 $mm^2$. Now open the primary seal by separating the front panel for the back panel, using care so as not to disturb the region where the secondary closing element is located. With the front and back panels separated, remove any protective covering, if present, from the secondary closing element. Now activate the secondary closing element as follows. Place the strip from the back panel onto a rigid horizontal surface, with the side containing the secondary closing element facing upwards. Position the strip from the front panel such that it is vertically and horizontally aligned over the strip from the back panel, with the sides containing the secondary closing element facing each other such that both sides of the secondary closing element are aligned. Now place the front panel onto the back panel, and then place the prepared padded weight on top of the aligned strips such that the weight is centered over and aligned with the secondary closing element. Start a 30 second timer. After 30 seconds have elapsed, the padded weight is removed and set aside. In like fashion, a total of five replicate test specimen strips are prepared and activated from the secondary closing element region of five separate absorbent article packages.

Program the CRE test frame as follows. Set the grip-to-grip separation to a gauge length of 60 mm. To note, this gauge length can be adjusted to accommodate smaller or larger test specimens. Zero the crosshead. Program the test frame to move the grips closer together by an intentional slack of 1.0 mm to ensure no pretension force exists on the test specimen at the onset of the test. (During this motion, the specimen will become slack between the grips.) The grips are then programmed to move apart at a slack speed of 1.0 mm/s for the initial slack distance of 1.0 mm, then continue to move apart at a speed of 5.0 mm/s until the opposing sides of the seal (i.e. front and back panels) are fully separated.

For test specimens of the primary seal, the test is executed as follows. Insert each leg of the test specimen in the grips such that the test specimen is centered laterally in the grips, the sealed area is located approximately equidistant between the grips and the seal line is perpendicular to the pull direction of the crosshead, avoiding any stress on the seal prior to the initiation of the test. Trim the legs of the test specimen, as needed, such that the specimen fits within the grips and is positioned as previously specified. If needed to accommodate a smaller or larger test specimen, adjust the gauge length and re-zero the crosshead. Start the test and continuously collect force ("load") and displacement data at a data acquisition rate of 100 Hz. Return the crosshead to its zero position. Remove the legs of the test specimen from the grips and discard. In like fashion, repeat the process until all five test specimen replicates of the primary seal have been tested.

For test specimens of the secondary closing element, the test is executed as follows. Insert each leg of the prepared, activated test specimen in the grips such that the test specimen is centered laterally in the grips, the sealed area is located approximately equidistant between the grips and the seal line is perpendicular to the pull direction of the crosshead, avoiding any stress on the seal prior to the initiation of the test. Trim the legs of the test specimen, as needed, such that the specimen fits within the grips and is positioned as previously specified. If needed to accommodate a smaller or larger test specimen, adjust the gauge length and re-zero the crosshead, adjust the gauge length and re-zero the crosshead. Start the first peel test and continuously collect force ("load") and displacement data at a data acquisition rate of 100 Hz. Return the crosshead to its zero position. Now remove the test specimen from the grips such that the sealable regions of the specimen are not contaminated in the process. Now realign the legs of the test specimen to their original position (same as that used for the first peel), then re-activate the secondary closing element using the padded weight as previously described (i.e. padded weight in place over scalable region on a rigid horizontal surface for 30 seconds). Immediately after 30 seconds have elapsed, follow the same procedure as previously described to insert the test specimen in the grips and start the second peel test. In like fashion, execute a third, fourth and fifth peel test for the test specimen, re-activating the secondary closing element after each peel test, as previously described. After the fifth peel test is complete, the test specimen is removed from the grips and discarded. In like fashion, repeat the entire process until five peels have been executed on all five test specimen replicates of the secondary closing element.

Construct a graph of load (N) versus displacement (mm) for the first peel (i.e. the only peel for test specimens obtained from the primary seal). From the graph, determine the peak force and record as peak load to the nearest mN. Now divide the peak load (mN) by the width of the seal (mm) and record as normalized peak load at first peel to the nearest mN/mm. Calculate the average peel force along the path length that includes the central 80% of the curve to the nearest mN. The central 80% of the curve is determined from the portion of the curve that begins with the first load value greater than 0.01 N and ends with the last load value that is greater than 0.01 N. Now divide the average peel force (mN) by the width of the seal (mm) and record as normalized average peel force at first peel to the nearest mN/mm. Calculate the area under the curve for the central 80% of the curve to the nearest mN-mm, then divide by the area of the seal ($mm^2$) and record as normalized peel energy at first peel to the nearest mN/mm. In like fashion, repeat this entire process for the second, third, fourth and fifth peels for the secondary closing element test specimen, labeling the parameters with the respective second peel, third peel, fourth peel and fifth peel distinctions.

In like fashion, the entire procedure is repeated for a total of five replicate test specimens of the primary seal and five replicate test specimens from the secondary closing element.

The arithmetic mean among the five replicate test specimens of the primary seal is calculated for each of the parameters, and reported as Normalized Peak Load at first peel to the nearest 0.1 mN/mm, Normalized Average Peel Force at first peel to the nearest 0.1 mN/mm and Normalized Peel Energy at first peel to the nearest 0.1 mN/mm.

The arithmetic mean among the five replicate test specimens of the secondary closing element is calculated for each of the parameters for the first peel and fifth peel, as follows. Report Normalized Peak Load at first peel and Normalized Peak Load at fifth peel, both to the nearest 0.1 mN/mm; report Normalized Average Peel Force at first peel and Normalized Average Peel Force at fifth peel, both to the nearest 0.1 mN/mm; and report Normalized Peel Energy at first peel and Normalized Peel Energy at fifth peel, both to the nearest 0.1 mN/mm. Additionally for the secondary closing element, the strength of the first peel can be compared to the strength of the fifth peel by dividing the parameter value at the fifth peel by the parameter value at the first peel, then multiplying by 100 and reporting to the nearest %, noting which parameter is being compared.

Strength Tensile Test Method

The Strength Tensile Test Method is run according to ASTM D828-16 "Standard Test Method for Tensile Properties of Paper and Paperboard Using Constant-Rate-of-Elongation Apparatus" with the following specifications and/or modifications: Two sets of test specimens are cut from package materials containing a weakened region. The first set of test specimens contain the weakened region, such that the weakened region is disposed the entire way across the width test sample and is centered along and perpendicular to the length of the test specimen. The second set of test specimens are cut from the same package materials and are oriented in the same direction as the first set but do not include a weakened region. The specimen length is about 101.6 mm (4 in.) to allow sufficient specimen for clamping in the instrument grips with a distance between the grips of 50.8 mm (2 in.). The rate of grip separation during the test is 300 mm/min. When placing the test specimens containing the weakened region into the grips for testing, the path of the weakened region is to be centered between the grips and perpendicular to the pull axis of the tensile tester. The average tensile strength of the first specimen set containing the weakened region is reported as the Weakened Region Tensile Strength (WRTS) to the nearest 0.01 kN/m. The average tensile strength of the second specimen set without the weakened region is reported as the Package Tensile Strength (MD or CD) to the nearest 0.01 kN/m.

Weakened Region Performance (WRP) Factor—The Weakened Region Performance Factor is calculated by taking the ratio of the Weakened Region Tensile Strength (WRTS) of a package versus the Tensile Strength of the package measured in the same direction (MD or CD). The factor is calculated according to the following equation and reported to the nearest 0.01 units:

$$WRP\text{ Factor} = \frac{\text{Weakened Region Tensile Strength}\left(\frac{kN}{m}\right)}{\text{Package Tensile Strength}\left(\frac{kN}{m}\right)}$$

Tear Tensile Test Method

The Tear Tensile Test Method is run according to ASTM D2261-13 "Tearing Strength of Fabrics by the Tongue (Single Rip) Procedure (Constant-Rate-of-Extension Tensile Testing Machine), which has been adapted for testing package materials comprising natural materials and a weakened region, with the following specifications and/or modifications: Test specimens are cut from package materials containing a weakened region, such that the path of the weakened region is oriented along the center of the specimen width. The specimen width is 50.4 mm (2 in.), with 25.4 mm (1 in.) on either side of the line of weakened regions. The 75 mm (3 in.) preliminary cut made along the center of the width should not partially cut a land region within the weakened region, such that only whole land regions are torn during the test. A total of five replicate test specimens are prepared. The distance between the clamps is set at 50.4 mm (2 in.) at the start of the test, and a testing speed of 300 mm/min is used. Preconditioning, conditioning, and testing of dry test specimens is performed as specified in ASTM D685-17 "Standard Practice of Conditioning Paper and Paper Products for Testing". Calculation Option 1, Average of Five Highest Peaks, is used to measure the average tear strength (peak force) of each of the first five land areas torn during the test and recorded to the nearest 0.01 N. This procedure is repeated for all five test specimens and the arithmetic mean of the five recorded values is calculated and reported as the Absolute Tear Strength value to the nearest 0.01 N. The Absolute Tear strength value is divided by the average width of all the land areas, which were torn, and peak forces measured during testing, and is reported as the Relative Tear Strength value to the nearest 0.01 N/mm.

Tear Performance Factor (TP Factor)—The Tear Performance Factor is calculated by taking the ratio of the package Weakened Region Tensile Strength (WRTS), according to the Strength Tensile Test Method described herein, versus the Absolute Tear Tensile of the weakened region of the package, according to the Tear Tensile Test Method described herein. The factor is calculated according to the following equation and reported to the nearest 0.01 units:

$$TP\ \text{Factor} = \frac{\text{Weakened Region Tensile Strength}\left(\frac{kN}{m}\right)}{\text{Absolute Tear Tensile}\,(N)}$$

Stretch At Break—Stretch At break is calculated by dividing the Mean Elongation at Break (mm) by the initial test length (test span) of 50.8 mm, and then multiplying by 100. Calculate the stretch at break for the MD replicates and then the CD replicates and report respectively as MD Stretch at Break and CD Stretch at Break to the nearest percent.

Tensile Energy Absorption (TEA)—Tensile Energy Absorption (TEA) is calculated using the following equation:

$$TEA = (1000 * \text{Mean Area Under Curve, } mJ) / (\text{width of test sample} * \text{initial test length})$$

where the width of the test sample is 25.4 mm, and the initial test length (test span) is 50.8 mm. Calculate the TEA for the MD replicates and then CD replicates and report respectively as MD TEA and CD TEA to the nearest $J/m^2$.

Tensile Energy Absorption (TEA) Index—Tensile Energy Absorption (TEA) Index is calculated using the following equation:

$$TEA\ \text{Index} = (TEA)/\text{Basis Weight}$$

where TEA is in units of $J/m^2$, and Basis Weight is in units of $g/m^2$. Calculate the TEA Index for the MD replicates and then the CD replicates and report respectively as MD TEA Index and CD TEA Index to the nearest J/g.

Burst Strength Test Method

Burst strength is the maximum uniformly distributed pressure that a test sample can withstand. Burst strength is measured in accordance with compendial method ISO 2758: 2014 using a test apparatus as described within the method. A suitable instrument is the 13-60 Burst Tester for Paper and Foils available from Testing Machines, Inc (New Castle, DE), or equivalent. The instrument is calibrated and operated as per the manufacturer's instructions. All measurements are performed in a laboratory maintained at 23 °C+/−2 °C and 50%+/−2% relative humidity, and test samples are conditioned in this environment for at least 2 hours prior to testing.

Measurements are made on test samples taken from rolls or sheets of the raw material, or test specimens obtained from a finished package. When excising a test sample from a finished package, use care to not impart any contamination or distortion to the test sample during the process. The test sample must be larger than the clamps used to hold the test sample in the instrument. The test sample should be taken from an area free of folds, wrinkles, or seams.

Measure the burst strength (using a clamping pressure sufficient to prevent slippage during the test, and a pumping rate of 95±15 mL/min) for a total of 10 replicate test samples. For samples that are sided, the side of the test sample that is meant to face the inside of the package faces the pressure when placed into the clamps, and 10 replicates are tested in this orientation. For samples that are balanced (not sided), 5 replicates are tested with the inside of the package facing the pressure and 5 replicates are tested with the outside of the package facing the pressure, and the results are averaged together. Record the pressure at which each test sample bursts to the nearest 0.001 kPa. If the burst pressure is less than 70 kPa, multiple layers of the test material must be used. To obtain the burst strength, divide the burst pressure by the number of layers tested. Calculate the arithmetic mean burst pressure for all replicates and report as Burst Strength to the nearest 0.001 kPa.

Caliper Test Method

The caliper, or thickness, of a single-layer test sample is measured under a static load by a micrometer, in accordance with compendial method ISO 534:2001, with modifications noted herein. All measurements are performed in a laboratory maintained at 23 °C±2 °C and 50%±2% relative humidity and test samples are conditioned in this environment for at least 2 hours prior to testing.

Caliper is measured with a micrometer equipped with a pressure foot capable of exerting a steady pressure of 70 kPa±0.05 kPa onto the test sample. The micrometer is a dead-weight type instrument with readings accurate to 0.1 micron. A suitable instrument is the TMI Digital Micrometer Model 49-56, available from Testing Machines Inc., New Castle, DE, or equivalent. The pressure foot is a flat ground circular movable face with a diameter that is smaller than the test specimen and capable of exerting the required pressure. A suitable pressure foot has a diameter of 16.0 mm. The test sample is supported by a horizontal flat reference platform that is larger than and parallel to the surface of the pressure foot. The system is calibrated and operated per the manufacturer's instructions.

Measurements are made on single-layer test samples taken from rolls or sheets of the raw material, or test samples obtained from a finished package. When excising the test sample from a finished package, use care to not impart any contamination or distortion to the sample during the process. The excised sample should be free from residual adhesive and taken from an area of the package that is free from any seams or folds. The test sample is ideally 200 $mm^2$ and must be larger than the pressure foot.

To measure caliper, first zero the micrometer against the horizontal flat reference platform. Place the test sample on the platform with the test location centered below the pressure foot. Gently lower the pressure foot with a descent rate of 3.0 mm per second until the full pressure is exerted onto the test sample. Wait 5 seconds and then record the caliper of the test sample to the nearest 0.1 micron. In like fashion, repeat for a total of ten replicate test samples. Calculate the arithmetic mean for all caliper measurements and report the value as Caliper to the nearest 0.1 micron.

Basis Weight Test Method

The basis weight of a test sample is the mass (in grams) per unit area (in square meters) of a single layer of material and is measured in accordance with compendial method ISO 536:2019. The mass of the test sample is cut to a known area, and the mass of the sample is determined using an analytical balance accurate to 0.0001 grams. All measurements are performed in a laboratory maintained at 23 °C±2 °C and 50%±2% relative humidity and test samples are conditioned in this environment for at least 2 hours prior to testing.

Measurements are made on test samples taken from rolls or sheets of the raw material, or test samples obtained from a finished package. When excising the test sample from a finished package, use care to not impart any contamination or distortion to the sample during the process. The excised sample should be free from residual adhesive and taken from an area of the package that is free from any seams or folds. The test sample must be as large as possible so that any inherent material variability is accounted for.

Measure the dimensions of the single layer test sample using a calibrated steel metal ruler traceable to NIST, or equivalent. Calculate the Area of the test sample and record to the nearest 0.0001 square meter. Use an analytical balance to obtain the Mass of the test sample and record to the nearest 0.0001 gram. Calculate Basis Weight by dividing Mass (in grams) by Area (in square meters) and record to the nearest 0.01 grams per square meter (gsm). In like fashion, repeat for a total of ten replicate test samples. Calculate the arithmetic mean for Basis Weight and report to the nearest 0.01 grams/square meter.

In-Bag Stack Height Test Method

The in-bag stack height of a package of absorbent articles is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e., each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Test Procedure

Absorbent article packages are equilibrated at 23±2 °C and 50±5% relative humidity prior to measurement.

The horizontal sliding plate is raised, and an absorbent article package is placed centrally under the horizontal sliding plate in such a way that the absorbent articles within the package are in a horizontal orientation (see FIG. 6). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured, and the arithmetic mean is reported as the package width. The "In-Bag Stack Height"=(package width/absorbent article count per stack)×10 is calculated and reported to within ±0.5 mm.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A package comprising one or more absorbent articles comprising:

a package material comprises natural fibers;

the package material forms a front panel, a back panel opposite the front panel, a first side panel, a second side panel opposite the first side panel, a top panel, and a bottom panel opposite the top panel, wherein the panels define an interior compartment of the package, and wherein the one or more absorbent articles are disposed in the interior compartment, the package comprises a primary seal and the package is sealed by the primary seal such that the one or more absorbent articles are enclosed within the interior compartment, wherein the package comprises a secondary closing element and the secondary closing element is reclosable, wherein the secondary closing element comprises an adhesive having two adhesive surfaces, one of which is adhered to the package and the other is covered by a release liner, wherein the release liner is removed manually or automatically upon or after first opening of the primary seal to activate the secondary closing element, wherein the package is sealed by the primary seal such that the secondary closing element is enclosed within the package, and wherein the secondary closing element is located in between two gussets of the top panel.

2. The package of claim 1, wherein the package material has a Basis Weight between about 50 gsm and about 120 gsm, according to the Basis Weight Test Method disclosed herein.

3. The package of claim 1, wherein the primary seal exhibits a Normalized Average Peel Force at first peel of at least 50 mN/mm, according to the Seal Strength Test Method disclosed herein.

4. The package of claim 1, wherein the secondary closing element exhibits a Normalized Average Peel Force at first peel of at most 500 mN/mm, according to the Seal Strength Test Method disclosed herein.

5. The package of claim 1, wherein the secondary closing element exhibits a Normalized Average Peel Force at fifth peel of from 60% to 100% of the Normalized Average Peel Force at first peel according to the Seal Strength Test Method disclosed herein.

6. The package of claim 1, wherein the secondary closing element comprises a double-sided tape.

7. The package of claim 6, wherein one side of the double-sided tape is adhered to the package prior to opening and the other side is unattached to the package, the unattached side being covered by the release liner.

8. The package of claim 1, wherein the secondary closing element is located closer to the one or more absorbent articles than the primary seal.

9. The package of claim 1, wherein the secondary closing element has a width of at least 60% of the distance between the two gussets in the top panel.

10. The package of claim 1, wherein the package comprises a weakened region disposed in the package material configured to form an opening.

11. The package of claim 10, wherein the weakened region is located between the primary seal and the secondary closing element.

12. The package of claim 1, wherein the package material comprises at least 50 percent by weight natural fibers.

13. The package of claim 1, wherein the package material has a recyclable percentage of between about 60 percent and about 99.9 percent determined via the PTS-RH:021/97 (Draft October 2019) under category II Test Method disclosed herein.

14. A bag for forming the package of claim 1, wherein the bag comprises a first surface, a second surface, a third surface, a fourth surface and a fifth surface, an open end opposing the first surface; wherein one surface selected from the group consisting of the second surface, the third surface, the fourth surface and the fifth surface comprises the secondary closing element, wherein the secondary closing element comprises an adhesive having two adhesive surfaces, one of which is adhered to the one surface and the other is covered by a release liner.

15. The bag of claim 14, wherein two or more surfaces selected from the group consisting of the second surface, the third surface, the fourth surface and the fifth surface comprises adhesive to form the primary seal.

16. The bag of claim 14, wherein another one surface selected from the second surface, the third surface, the fourth surface and the fifth surface not comprising the secondary closing element and opposing the one surface comprises a receptive area.

17. The package of claim 1, wherein the secondary closing element has a width of from 20% to 90% of a width of the primary seal.

18. The package of claim 1, wherein the secondary closing element has a height of from 120% to 3000% of a height of the primary seal.

19. A bag for forming a package comprising one or more absorbent articles, wherein the bag comprises a package material and a first surface, a second surface, a third surface, a fourth surface and a fifth surface, an open end opposing the first surface; wherein one surface selected from the group consisting of the second surface, the third surface, the fourth surface and the fifth surface comprises a secondary closing element, wherein the secondary closing element is reclosable, wherein the secondary closing element comprises an adhesive having two adhesive surfaces, one of which is adhered to the one surface and the other is covered by a release liner, and two or more surfaces selected from the group consisting of the second surface, the third surface, the fourth surface and the fifth surface comprise a primary sealing area to form a primary seal.

* * * * *